US008119775B2

(12) United States Patent
Moretta et al.

(10) Patent No.: US 8,119,775 B2
(45) Date of Patent: Feb. 21, 2012

(54) HUMAN ANTI-KIR ANTIBODIES

(75) Inventors: Alessandro Moretta, Genoa (IT); Mariella Della Chiesa, Genoa (IT); Pascale Andre, Marseilles (FR); Laurent Gauthier, Marseilles (FR); Francois Romagné, La Ciotat (FR); Peter Andreas Nicolai Reumert Wagtmann, Rungsted Kyst (DK); Ivan Svendsen, Smørum (DK); Stefan Zahn, Ballerup (DK); Anders Svensson, Malmö (SE); Matthias Thórólfsson, Charlottenlund (DK); Søren Berg Padkær, Værløse (DK); Kristian Kjaergaard, Ballerup (DK); Pieter Spee, Allerød (DK); Michael Wilken, Hundested (DK)

(73) Assignees: University of Genoa, Genoa (IT); Innate Pharma S.A.S., Marseilles (FR); Novo Nordisk A/S, Bagsvaerd (DK)

( * ) Notice: Subject to any disclaimer, the term of this patent is extended or adjusted under 35 U.S.C. 154(b) by 480 days.

(21) Appl. No.: 12/244,170

(22) Filed: Oct. 2, 2008

(65) Prior Publication Data

US 2009/0081240 A1    Mar. 26, 2009

Related U.S. Application Data

(63) Continuation of application No. 11/630,176, filed as application No. PCT/EP2005/053122 on Jul. 1, 2005, now abandoned.

(60) Provisional application No. 60/642,808, filed on Jan. 11, 2005.

(30) Foreign Application Priority Data

Jul. 1, 2004   (WO) ................ PCT/DK2004/000470
Jul. 1, 2004   (WO) ................ PCT/IB2004/002464
Jan. 6, 2005   (DK) ................................ 2005 00025

(51) Int. Cl.
*C12P 21/08*     (2006.01)
*C07K 16/00*     (2006.01)

(52) U.S. Cl. .............................. 530/388.73; 530/388.15
(58) Field of Classification Search ........................ None
See application file for complete search history.

(56) References Cited

U.S. PATENT DOCUMENTS

| 4,816,567 | A | 3/1989 | Cabilly et al. |
| 5,539,094 | A | 7/1996 | Reed et al. |
| 5,583,034 | A | 12/1996 | Green et al. |
| 5,650,491 | A | 7/1997 | Reed et al. |
| 5,660,827 | A | 8/1997 | Thorpe et al. |
| 5,808,028 | A | 9/1998 | Long et al. |
| 6,524,583 | B1 | 2/2003 | Thorpe et al. |
| 2002/0061581 | A1 | 5/2002 | Lee et al. |
| 2005/0037002 | A1* | 2/2005 | Velardi et al. ............. 424/143.1 |

FOREIGN PATENT DOCUMENTS

| EP | 0 799 836 | 10/1997 |
| WO | WO 9816551 | 4/1998 |
| WO | WO 00/26671 | 5/2000 |
| WO | WO2005/003168 | 1/2005 |
| WO | WO2005/009465 | 2/2005 |

OTHER PUBLICATIONS

Klimka et al., 2000, Br. J> canc. vol. 83: 252-260.*
Benjamin et al., 1991, Intern. Rev. Immunol. pp. 149-164.*
Moesta, 2008, J. Immunol. vol. 180: 3969-3979.*
MOrretta et al., 1995, J. Exp. Med. vol. 182: 875-884.*
Moesta et al., 2009, J. Immunol. vol. 182: 3628-3637.*
Spaggiari, G.M. et al., Soluble HLA class I induces NK cell apoptosis upon the engagement of killer-activating HLA class I receptors through FasL-Fas interaction, Blood, 2002, vol. 100, No. 12, pp. 4098-4107.
Shin, J-S et al., Monoclonal Antibodies with Various Reactivity to p58 Killer Inhibitory Receptors, Hybridoma, 1999, vol. 18, No. 6, pp. 521-527.
Warren, H.S. et al., Functional Analysis of CD158b monoclonal antibodies recognizing the killer 1g-like receptors KIR2DS2, KIR2DL2 and KIR2DL3, Tissue Antigens, 2000, vol. 55, No. 1, pp. 80-81.
Koh, C.Y. et al., NK Inhibitory-Receptor Blockade for Purging of Leukemia: Effects on Hematopoietic Reconstitution, Biology of Blood and Marrow Transplantation, 2002, vol. 8, No. 1, pp. 17-25.
Farag, S.S. et al., "Natural killer cell receptors: new biology and insights into the graft-versus-leukemia effect", Blood, 2002, vol. 100, No. 6, pp. 1935-1947.
Barten, R. et al., "Divergent and convergent evolution of NK-cell receptors", Trends in Immunology, 2001, vol. 22, No. 1, pp. 52-57.
Moretta, A. et al., "Activating Receptors and Coreceptors Involved in Human Natural Killer Cell-Mediated Cytolysis", Annu. Rev. Immunol., 2001, vol. 19, pp. 197-223.
Moretta, A. et al., "Receptors for HLA Class-I Molecules in Human Natural Killer Cells", Annu. Rev. Immunol., 1996, vol. 14, pp. 619-648.
Poggi, A. et al., "p40, a novel surface molecule involved in the regulation of the non-major histocompatibility complex-restricted cytolytic activity in humans", Eur. J. Immunol., 1995, vol. 25, No. 2, pp. 369-376.

(Continued)

*Primary Examiner* — Amy Juedes
(74) *Attorney, Agent, or Firm* — Hunton & Williams LLP

(57) ABSTRACT

Compositions and methods for regulating an immune response in a subject are described. More particularly, described are human antibodies that regulate the activity of NK cells and allow a potentiation of NK cell cytotoxicity in mammalian subjects, and antibodies having antigen-binding properties similar to those of human monoclonal antibody 1-7F9 or 1-4F1. Described also are also fragments and derivatives of such antibodies, as well as pharmaceutical compositions comprising the same and their uses, particularly for use in therapy, to increase NK cell activity or cytotoxicity in subjects.

20 Claims, 20 Drawing Sheets

OTHER PUBLICATIONS

Vitale, M. et al., Isolation of a novel KIR2DL3-specific mAb: comparative analysis of the surface distribution and function of KIR2DL2, KIR2DL3 and KIR2DS2, International Immunology, 2004, vol. 16, No. 10, pp. 1459-1466.

Spaggiari, G.M. et al., "Soluble HLA class I molecules induce natural killer cell apoptosis through the engagement of CD8: evidence for a negative regulation exerted by members of the inhibitory receptor superfamily", Blood, 2002, vol. 99, No. 5, pp. 1706-1714.

Lanier, L.L., NK Cell Recognition, Annu. Rev. Immunol., 2005, vol. 23, pp. 225-274.

Karre, K. et al., "Selective rejection of H-2-deficient lymphoma variants suggests alternative immune defence strategy", Nature, 1986, vol. 319, pp. 675-678.

Lanier, L.L., "NK Cell Receptors", Annu. Rev. Immunol., 1998, vol. 16, pp. 359-393.

Ruggeri, L. et al., "Effectiveness of Donor Natural Killer Cell Alloreactivity in Mismatched Hematopoietic Transplants", Science, 2002, vol. 295, pp. 2097-2100.

Moretta, A. et al., "P58 Molecules as Putative Receptors for Major Histocompatibility Complex (MHC) Class I Molecules in Human Natural Killer (NK) Cells. Anti-p58 Antibodies Reconstitute Lysis of MHC Class I-protected Cells in NK Clones Displaying Different Specificities", J. Exp. Med., 1993, vol. 178, pp. 597-604.

Watzl, C. et al., "Homogenous expression of killer cell immunoglobulin-like receptors (KIR) on polyclonal natural killer cells detected by a monoclonal antibody to KIR2D", Tissue Antigens, 2000, vol. 56, pp. 240-247.

Valiante, N.M. et al., "Killer cell receptors: keeping pace with MHC class I evolution", Immunological Reviews, 1997, vol. 155, pp. 155-164.

Moretta, A. et al., "Function and Specificity of Human Natural Killer Cell Receptors", European Journal of Immunogenetics, 1997, vol. 24, pp. 455-468.

Moretta, A. et al., "Identification of Four Subsets of Human CD3⁻CD16⁺ Natural Killer (NK) Cells by the Expression of Clonally Distributed Functional Surface Molecules: Correlation between Subset Assignment of NK Clones and Ability to Mediate Specific Alloantigen Recognition", J. Exp. Med., 1990, vol. 172, pp. 1589-1598.

Ohlen, C. et al., "Studies of Sublines Selected for Loss of HLA Expression From an EBV-Transformed Lymphoblastoid Cell Line", J. Immunol., 1989, vol. 142, No. 9, pp. 3336-3341.

Wagtmann, N. et al., "Killer Cell Inhibitory Receptors Specific for HLA-C and HLA-B Identified by Direct Binding and by Functional Transfer", Immunity, 1995, vol. 3, pp. 801-809.

Wagtmann, N. et al., "Molecular Clones of the p58 NK Cell Receptor Reveal Immunoglobulin-Related Molecules with Diversity in Both the Extra- and Intracellular Domains", Immunity, 1995, vol. 2, pp. 439-449.

Moretta, A. et al., "A Novel Surface Antigen Expressed by a Subset of Human CD3⁻CD16⁺ Natural Killer Cells", Journal of Experimental Medicine, 1990, vol. 171, No. 3, pp. 695-714.

Fan, Q.R. et al., "Cobalt-mediated Dimerization of the Human Natural Killer Cell Inhibitory Receptor", J. Biol. Chem., 2000, vol. 275, No. 31, pp. 23700-23706.

Biassoni, R., "Human CD3⁻CD16⁺ Natural Killer Cells Express the hGATA-3 T Cell Transcription Factor and an Unrearranged 2.3-kb TcR δ Transcript", Eur. J. Immunol., 1993, vol. 23, pp. 1083-1087.

Boyington, J.C. et al., "Crystal Structure of an NK Cell Immunoglobulin-like Receptor in Complex with its Class I MHC Ligand", Nature, 2000, vol. 405, pp. 537-543.

Fan, Q.R. et al., "Crystal Structure of the Human Natural Killer Cell Inhibitory Receptor KIR2DL1-HLA-Cw4 Complex", Nat. Immunol., 2001, vol. 2, No. 5, pp. 452-460.

Gauthier, L. et al., "μ-Surrogate Light Chain Physicochemical Interactions of the Human PreB Cell Receptor: Implications for $V_H$ Repertoire Selection and Cell Signaling at the PreB Cell Stage", J. Immunol., 1999, vol. 162, pp. 41-50.

Colonna, M. et al., "Cloning of Immunoglobulin-Superfamily members Associated with HLA-C and HLA-B Recognition by Human Natural Killer Cells", Science, 1995, vol. 268, pp. 405-408.

Maenaka, K. et al., "Crystal Structure of the Human p58 Killer Cell Inhibitory Receptor (KIR2DL3) Specific for HLA-Cw3-related MHC Class I", Structure, 1999, vol. 7, No. 4, pp. 391-398.

Pende, D. et al., "Identification and Molecular Characterization of NKp30, a Novel Triggering Receptor Involved in Natural Cytotoxicity Mediated by Human Natural Killer Cells", J. Exp. Med., 1999, vol. 190, No. 10, pp. 1505-1516.

Saulquin, X. et al., Crystal Structure of the Human Natural Killer Cell Activating Receptor KIR2DS2 (CD158j), J. Exp. Med., 2003, vol. 197, No. 7, pp. 933-938.

Saunal, H. et al., "Mapping of Viral Conformational Epitopes Using Biosensor Measurements", J. Immunol. Methods, 1995, vol. 1983, pp. 33-41.

Sun et al., "Chimeric antibody with human constant regions and mouse variable regions directed against carcinoma-associated antigen 17-1A," Proc. Natl. Acad. Sci. USA, Jan. 1987, pp. 214-218, vol. 84.

Database Geneseq 'Online!, Accession No. ABG74248, "Mouse antibody 3E11 light chain variable region" Apr. 23, 2003, pp. 1-2, XP-002309299.

EMBL, Accession No. AAW01153, "MAb 10.1 light chain CDR (MAb binds type II phospholipase A2)" Feb. 10, 1997, p. 1, XP-002309300.

EMBL, Accession No. AAE17798, "E. coli monoclonal antibody heavy chain variable region CDR #2" May 7, 2002, p. 1, XP-002309301.

* cited by examiner

FIGURE 4
A
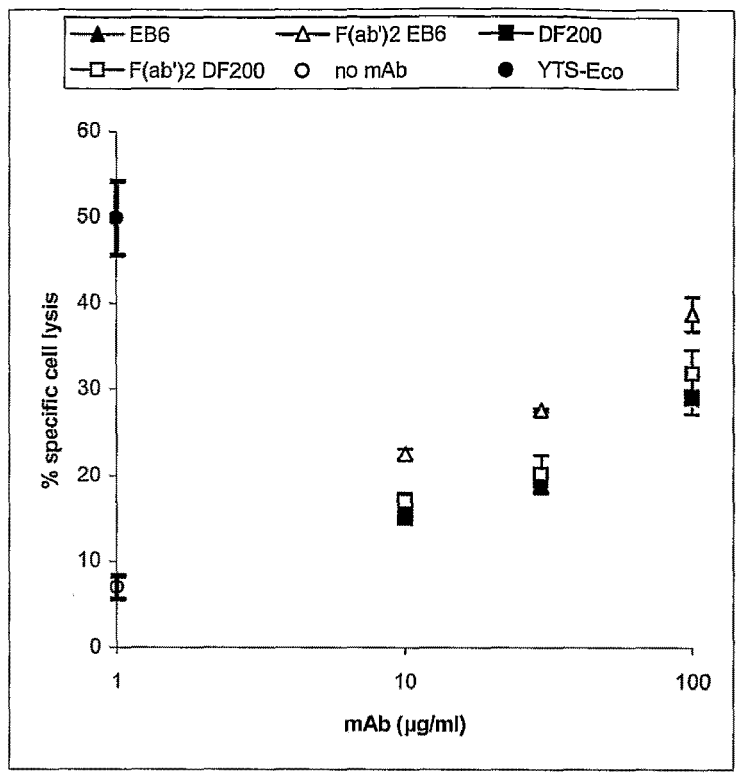
B
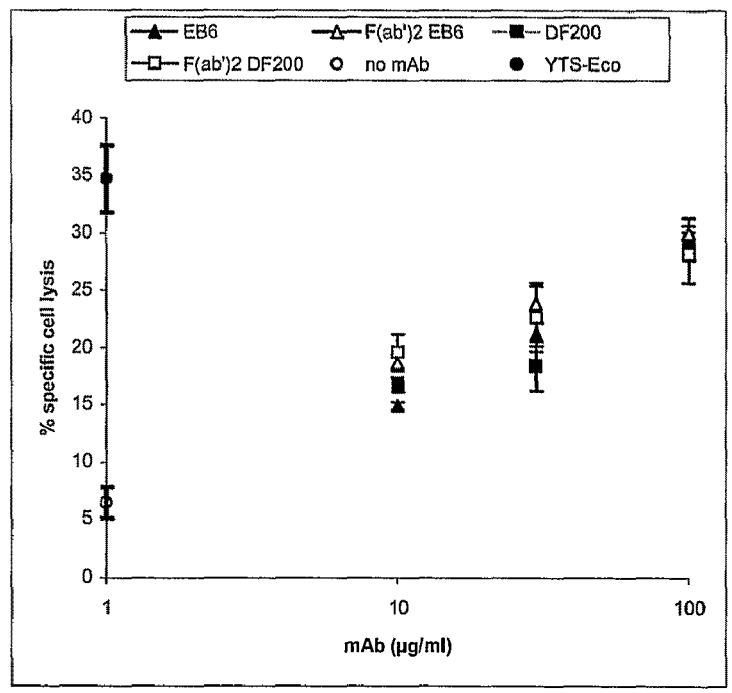

FIGURE 5
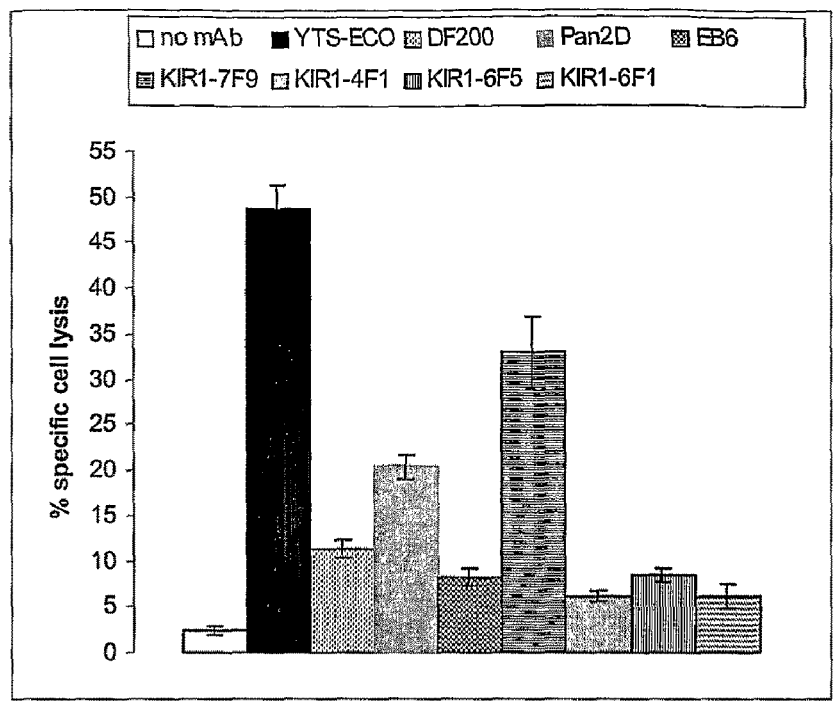
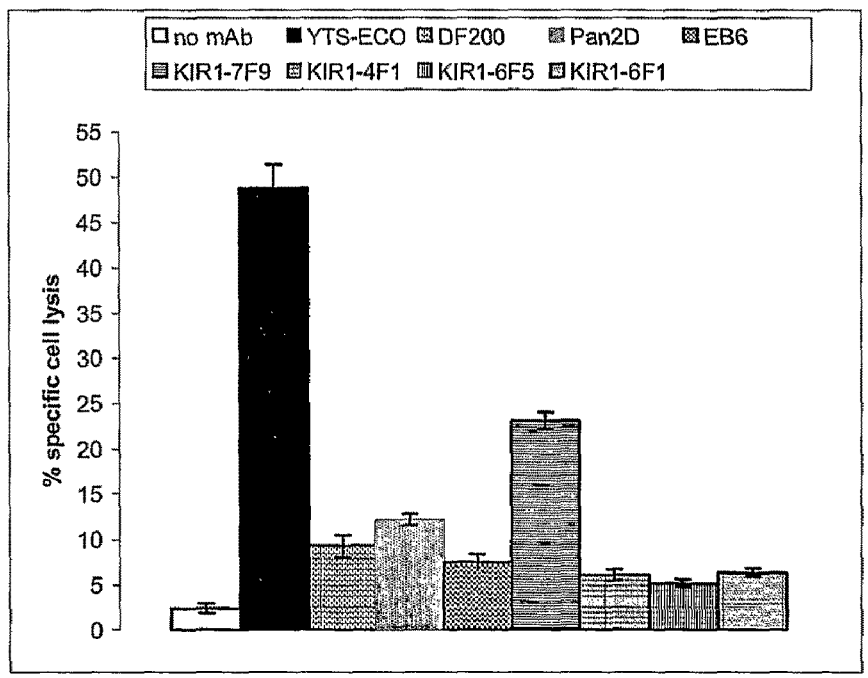

FIGURE 6
A
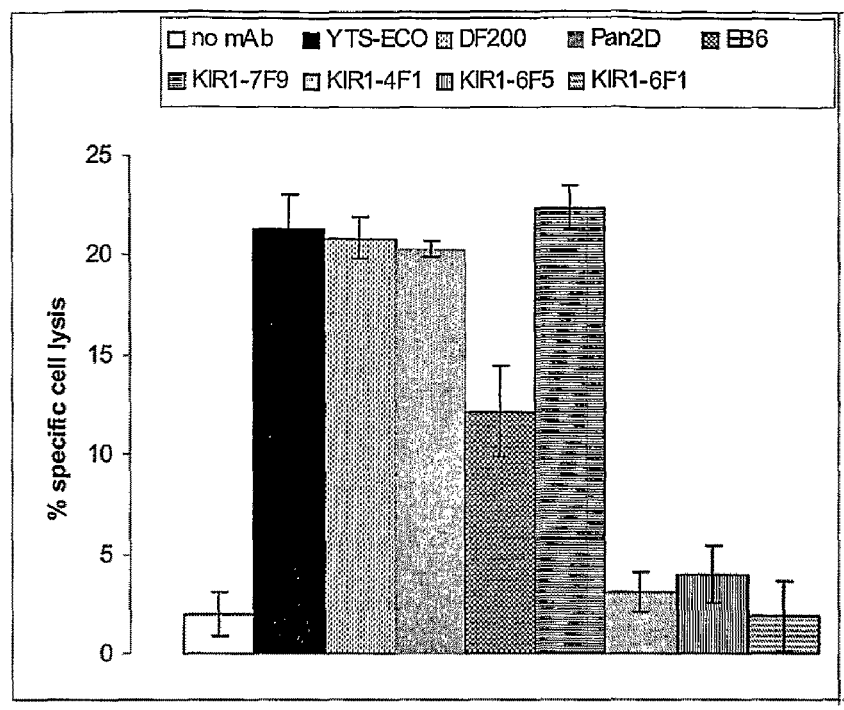
B
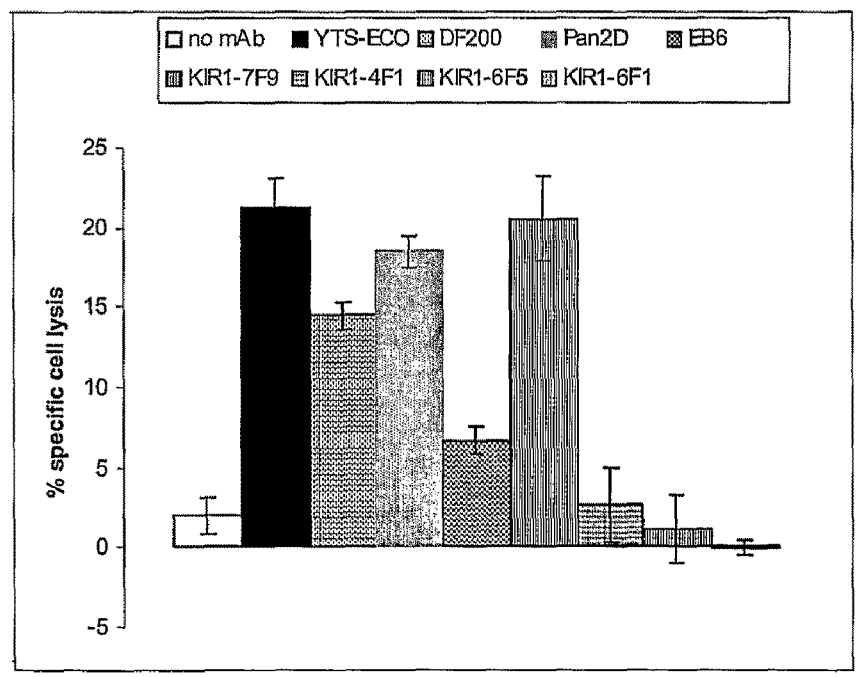

FIGURE 11
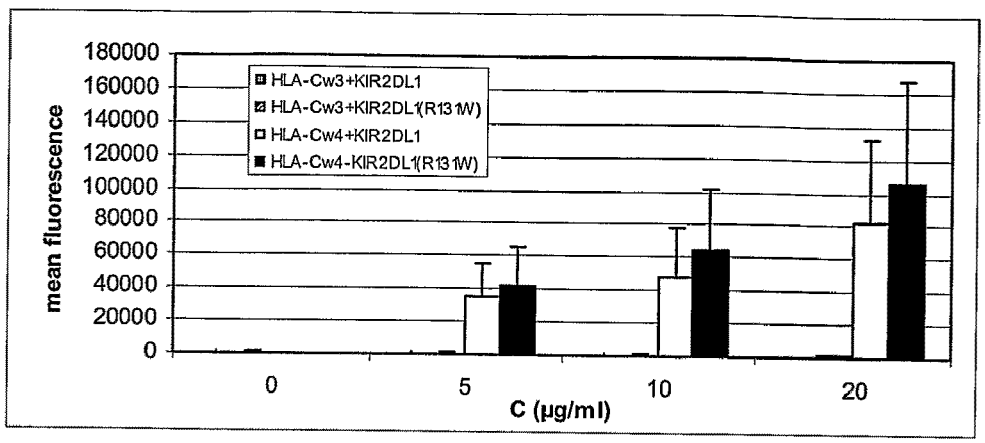
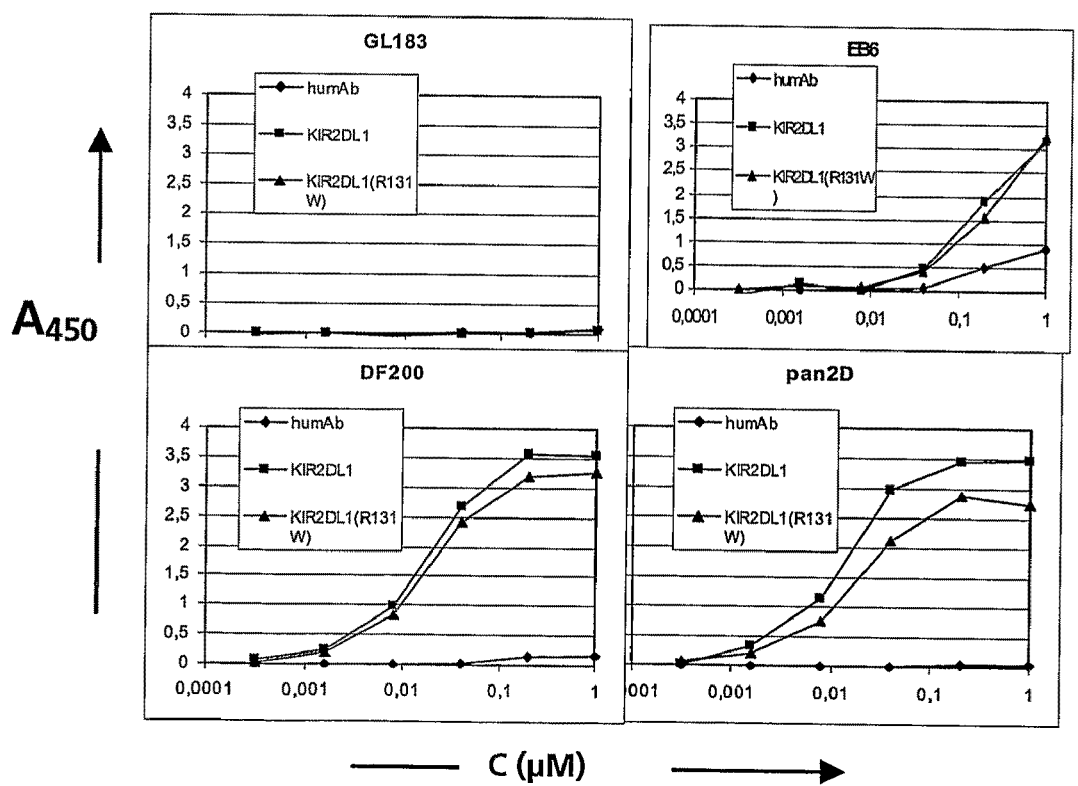

```
                              1                                                50
DF-200 light variable     (1) M--ESQTLVFISILLWIYGADGNIVMTQSPKSMSMSVGERVTITCKASEN
PAN2D-Light-variable      (1) MDFQVQIFSFLLISASVIMSRGQIVLTQSPASMSASLGERVTMTCTASSS
            Consensus     (1)       Q  FI I    L  A GNIVLTQSP SMS SLGERVTLTC AS
                              51                                               100
DF-200 light variable    (49) VVI-YVSWYQQKPEQSPKLLIYGASNRYIGVPDRFTGSGSATDFLTISS
PAN2D-Light-variable     (51) VSSSYLYWYQQKPGSSPKLWIYSTSNLASGVPARFSGSGSGTSVSLTISS
            Consensus    (51) V S YL WYQQKP  SPKL IY  SN  SGVP RFSGSGSAT FSLTISS
                              101                     131
DF-200 light variable    (98) VQAEDLADYHCGQGVSYPYTFGGGTKLEIKR
PAN2D-Light-variable    (101) MEAEDAATYYCHQYHRSPPTFGGGTKLEIKR
            Consensus   (101) M AED A YHC Q H  P TFGGGTKLEIKR
```

B

```
DF-200 light variable   (44) KASENVVI-YVS  (SEQ ID NO.3)
PAN2D-Light-variable    (46) TASSSVSSSYLY  (SEQ ID NO.4)
           Consensus         AS     V S YL
```

C

```
DF-200 light variable   (70) GASNRYI  (SEQ ID NO.5)
PAN2D-Light-variable    (73) STSNLAS  (SEQ ID NO.6)
           Consensus          SN  S
```

D

```
DF-200 light variable  (109) GQGVSYPYT  (SEQ ID NO.7)
PAN2D-Light-variable   (112) HQYHRSPPT  (SEQ ID NO.8)
           Consensus          Q H  P T
```

MAVLGLLFCLVTFPSCVLS

QVQLEQSGPGLVQPSQSLSITCTVS<u>GFSFTPYGVH</u>WVRQSPGKGLEWLG<u>VIWSGGNTDY NAAFIS</u>RLSINKDNSKSQVFFKMNSLQVNDTAIYYCAR<u>NPRPGNYPYGMDY</u>WGQGTSVT VSS (SEQ ID NO:9)

B

GFSFTPYGVH (SEQ ID NO:10)

C

VIWSGGNTDYNAAFIS (SEQ ID NO:11)

D

NPRPGNYPYGMDY (SEQ ID NO:12)

FIGURE 14

1-7F9 VL and VH

A

EIVLTQSPVTLSLSPGERATLSCRASQSVSSYLAWYQQKPGQAPRLLIYDASNRATGIPARFSGSGSG
TDFTLTISSLEPEDFAVYYCQQRSNWMYTFGQGTKLEIKRT (SEQ ID NO:15)

B gaaattgtgttgacacagtctccagtcaccctgtctttgtctccaggggaaagagccaccctctcctg
cagggccagtcagagtgttagcagctacttagcctggtaccaacagaaacctggccaggctcccaggc
tcctcatctatgatgcatccaacagggccactggcatcccagccaggttcagtggcagtgggtctggg
acagacttcactctcaccatcagcagcctagagcctgaagatttgcagtttattattgtcagcagcg
tagcaactggatgtacacttttggccaggggaccaagctggagatcaaacgaact (SEQ ID NO:16)

C

QVQLVQSGAEVKKPGSSVKVSCKASGGTFSFYAISWVRQAPGQGLEWMGGFIPIFGAANYAQKFQGRV
TITADESTSTAYMELSSLRSDDTAVYYCARIPSGSYYYDYDMDVWGQGTTVTVSS (SEQ ID NO:17)

D caggtccagctggtgcagtctggggctgaggtgaagaagcctgggtcctcggtgaaggtctcctgcaa
ggcttctggaggcaccttcagtttctatgctatcagctgggtgcgacaggcccctggacaagggcttg
agtggatgggagggttcatccctatctttggtgcagcaaactacgcacagaagttccagggcagagtc
acgattaccgcggacgaatccacgagcacagcctacatggaactgagcagcctgagatctgacgacac
ggccgtgtattactgtgcgagaatccctagtgggagctactactacgactacgatatggacgtctggg
gccaagggaccacggtcaccgtctcctca (SEQ ID NO:18)

FIGURE 18
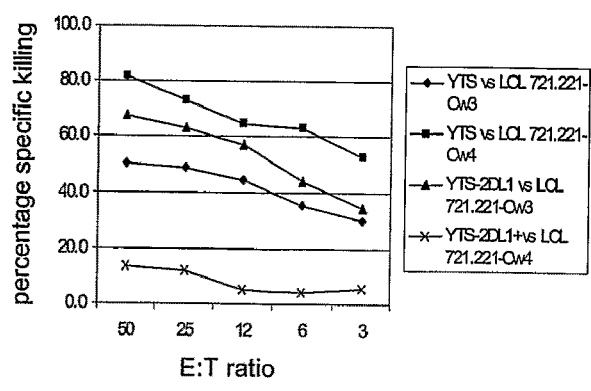
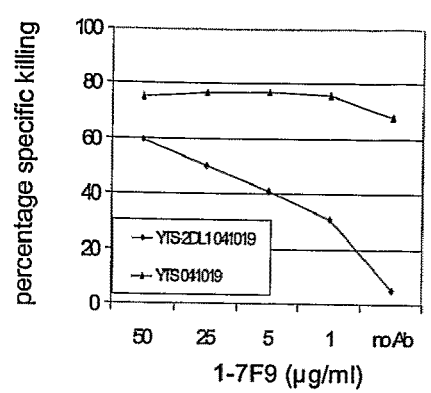

FIGURE 20

```
  1    HEGVHRKPSL LAHPGRLVKS EETVILQCWS DVMFEHF LH REGM NDT R
 51    L GEHHDGVS KAN SISRMT Q LAGTYRC  GSVTHS YQV SAPSDPLDIV
101    IIGLYEKPSL SAQLGPTVLA GENVTLSCSS RSSYDMYHLS REGEAHERRL
151    PAGPKVNGTF QADFPLGPAT HGGTYRCFGS FHDSPYEWSK SSDPLLVSVT
201    GNPSNSWPSP TEPSSKTGNP RHLH
```

HUMAN ANTI-KIR ANTIBODIES

CROSS REFERENCE TO RELATED APPLICATIONS

This application is a continuation of U.S. patent application Ser. No. 11/630,176, filed Dec. 19, 2006 (the "parent application"), which is the US national stage (under 35 U.S.C. §371) of International Patent Application PCT/EP2005/053122 (published as WO 2006/003179), filed Jul. 1, 2005, which designates the US, which claims the benefit of priority, under 35 USC §365(b), of International Patent Application Nos. PCT/DK2004/000470 (published as WO 2005/003168) and PCT/IB2004/002464 (published as WO 2005/003172), both filed Jul. 1, 2004, and Danish Patent Application No. PA 2005 00025, filed Jan. 6, 2005, and claims the benefit (under 35 U.S.C. §119(e)) of U.S. Provisional Patent Application No. 60/642,808, filed Jan. 11, 2005.

FIELD OF THE INVENTION

The present invention relates to human antibodies, as well as fragments and derivatives thereof, which cross-react with and/or block two or more inhibitory KIR receptors present on the surface of NK cells, and potentiate NK cell cytotoxicity in mammalian subjects or in a biological sample. The invention also relates to methods of making such antibodies, fragments, variants, and derivatives; pharmaceutical compositions comprising the same; and the use of such molecules and compositions, particularly in therapy, to increase NK cell activity or cytotoxicity in subjects.

BACKGROUND OF THE INVENTION

Natural killer (NK) cells are a sub-population of lymphocytes, involved in immunity and in the host immune surveillance system.

NK cells are mononuclear cell that develop in the bone marrow from lymphoid progenitors, and morphological features and biological properties typically include the expression of the cluster determinants (CDs) CD16, CD56, and/or CD57; the absence of the alpha/beta or gamma/delta TCR complex on the cell surface; the ability to bind to and kill target cells that fail to express "self" major histocompatibility complex (MHC)/human leukocyte antigen (HLA) proteins; and the ability to kill tumor cells or other diseased cells that express ligands for activating NK receptors. NK cells are characterized by their ability to bind and kill several types of tumor cell lines without the need for prior immunization or activation. NK cells can also release soluble proteins and cytokines that exert a regulatory effect on the immune system; and can undergo multiple rounds of cell division and produce daughter cells with similar biologic properties as the parent cell. Upon activation by interferons and/or cytokines, NK cells mediate the lysis of tumor cells and of cells infected with intracellular pathogens by mechanisms that require direct, physical contacts between the NK cell and the target cell. Lysis of target cells involves the release of cytotoxic granules from the NK cell onto the surface of the bound target, and effector proteins such as perforin and granzyme B that penetrate the target plasma membrane and induce apoptosis or programmed cell death. Normal, healthy cells are protected from lysis by NK cells.

Based on their biological properties, various therapeutic and vaccine strategies have been proposed in the art that rely on a modulation of NK cells. However, NK cell activity is regulated by a complex mechanism that involves both stimulating and inhibitory signals.

Briefly, the lytic activity of NK cells is regulated by various cell surface receptors that transduce either positive or negative intracellular signals upon interaction with ligands on the target cell. The balance between positive and negative signals transmitted via these receptors determines whether or not a target cell is lysed (killed) by a NK cell. NK cell stimulatory signals can be mediated by Natural Cytotoxicity Receptors (NCR) such as NKp30, NKp44, and NKp46; as well as NKG2C receptors, NKG2D receptors, certain activating Killer Ig-like Receptors (KIRs), and other activating NK receptors (Lanier, Annual Review of Immunology 2005; 23:225-74). NK cell inhibitory signals can be mediated by receptors like Ly49, CD94/NKG2A, as well as certain inhibitory KIRs, which recognize major histocompatibility complex (MHC) class I-molecules (Kärre et al., Nature 1986; 319:675-8; Öhlén et al, Science 1989; 246:666-8). These inhibitory receptors bind to polymorphic determinants of MHC class I molecules (including HLA class I) present on other cells and inhibit NK cell-mediated lysis.

KIRs, sometimes also referred to as Killer Inhibitory Receptors, have been characterized in humans and non-human primates, and are polymorphic type 1 trans-membrane molecules present on certain subsets of lymphocytes, including NK cells and some T cells. KIRs interact with determinants in the alpha 1 and 2 domains of the MHC class I molecules and, as described above, distinct KIRs are either stimulatory or inhibitory for NK cells.

The nomenclature for KIRs is based upon the number of extracellular domains (KIR2D and KIR3D having two and three extracellular Ig-domains, respectively) and whether the cytoplasmic tail is long (KIR2DL or KIR3DL) or short (KIR2DS or KIR3DS). The presence or absence of a given KIR is variable from one NK cell to another within the NK population present in a single individual. Among humans, there is also a relatively high level of polymorphism of KIR genes, with certain KIR genes being present in some, but not all individuals. The expression of KIR alleles on NK cells is stochastically regulated, meaning that, in a given individual, a given lymphocyte may express one, two, or more different KIRs, depending on the genotype of the individual. The NK cells of a single individual typically express different combinations of KIRs, providing a repertoire of NK cells with different specificities for MHC class I molecules.

Certain KIR gene products cause stimulation of lymphocyte activity when bound to an appropriate ligand. The activating KIRs all have a short cytoplasmic tail with a charged trans-membrane residue that associates with an adapter molecule having an Immunoreceptor Tyrosine-based Activation Motifs (ITAMs) which transduce stimulatory signals to the NK cell. By contrast, inhibitory KIRs have a long cytoplasmic tail containing Immunoreceptor Tyrosine-based Inhibitory Motif (ITIM), which transduce inhibitory signals to the NK cell upon engagement of their MHC class I ligands. The known inhibitory KIRs include members of the KIR2DL and KIR3DL subfamilies. Inhibitory KIRs having two Ig domains (KIR2DL) recognize HLA-C allotypes: KIR2DL2 (formerly designated p58.2) and the closely related, allelic gene product KIR2DL3 both recognize "group 1" HLA-C allotypes (including HLA-Cw1, -3, -7, and -8), whereas KIR2DL1 (p58.1) recognizes "group 2" HLA-C allotypes (such as HLA-Cw2, -4, -5, and -6). The recognition by KIR2DL1 is dictated by the presence of a Lys residue at position 80 of HLA-C alleles. KIR2DL2 and KIR2DL3 recognition is dictated by the presence of an Asn residue at position 80 in HLA-C. Importantly, the great majority of HLA-C alleles have either an Asn or a Lys residue at position 80. Therefore, KIR2DL1, -2, and -3 collectively recognize essentially all HLA-C allotypes found in humans. One KIR with three Ig domains, KIR3DL1 (p70), recognizes an epitope shared by HLA-Bw4 alleles. Finally, KIR3DL2 (p140), a homodimer of molecules with three Ig domains, recognizes HLA-A3 and -A11.

Although multiple inhibitory KIRs and/or other MHC class I-specific inhibitory receptors (Moretta et al, Eur J Immunogenet. 1997; 24(6):455-68; Valiante et al, Immunol Rev 1997; 155:155-64; Lanier, Annu Rev Immunol 1998; 16:359-93) may be co-expressed by NK cells, in any given individual's NK repertoire there are cells that express only a single KIR, and thus are inhibited only by specific MHC class I alleles (or alleles belonging to the same group of MHC class I allotypes). Human MHC class I molecules often are referred to as Human Histocompatibility Antigen (HLA) class I.

NK cell populations or clones that are KIR-ligand mismatched with respect to their targets, i.e., that express KIRs which do not recognize any HLA molecule of a host, have been shown to mediate potent, life-saving anti-tumor responses after allogeneic bone-marrow transplantation in leukemia patients (Ruggeri et al., Science 2002, 295:2097-2100). The underlying mechanism is believed to be that HLA mismatched hematopoietic transplantation leads to the expansion of donor-derived NK cells expressing KIR which do not recognize any HLA ligands in the recipient, and thus are not inhibited via KIR. These allogeneic NK clones exert potent anti-tumor activity. This response is very strong in patients diagnosed with acute myeloid leukaemia (AML), and treated with KIR-MHC mismatched haplo-identical transplants. One way of reproducing this effect by pharmacological treatment of a patient would be to administer reagents that block the KIR/HLA interaction to activate the patient's endogenous NK cells.

Certain monoclonal antibodies specific for KIR2DL1 have been shown to block the interaction of KIR2DL1 with "group 2" HLA-C allotypes, such as HLA-Cw4 (Moretta et al., J Exp Med 1993; 178:597-604), and to promote NK-mediated lysis of target cells that express those HLA-C allotypes. Monoclonal antibodies against KIR2DL2/3 that block the interaction of KIR2DL2/3 with HLA-Cw3 or similar allotypes have also been described (Moretta et al., J Exp Med 1993; 178: 597-604). Such antibodies are not ideal for use in clinical situations, as the development of two therapeutic monoclonal antibodies (mAbs) and administration of both of such antibodies or a selection of one of such antibodies (after appropriate diagnosis) would be required to treat all potential patients, depending on whether any given patient was expressing group 1 or group 2 HLA-C allotypes.

Watzl et al. (Tissue Antigens 2000; 56:240-247) produced cross-reacting murine antibodies recognizing multiple isotypes of KIRs, but those antibodies did not potentiate the lytic activity of NK cells. Further, Spaggiari et al. (Blood 2002; 99:1706-1714 and Blood 2002; 100:4098-4107) carried out experiments utilizing numerous murine monoclonal antibodies against various KIRs. One of those antibodies, NKVSF1 (also known as Pan2D), was reported to recognize a common epitope of KIR2DL1 (CD158a), KIR2DL2 (CD158b) and KIR2DS4 (p50.3). Shin et al. (Hybridoma 1999; 18:521-7) also reported the production of two monoclonal antibodies, denoted A210 and A803g, capable of binding to all of KIR2DL1, KIR2DL3, and KIR2DS4. However, for therapeutic use of an antibody in blocking the inhibitory KIRs of a patient's NK cells, the fewer activating KIR molecules an antibody cross-reacts with, the better, since blockade of activating receptors could impair the stimulation of NK cells.

Thus, an antibody having the antigen-binding characteristics of NKVSF1, A210, or A803g would not be optimal in a clinical setting. Additionally, the use of murine monoclonal antibodies in the treatment of a human patient may result in a host immune-response against the antibodies, thus compromising the efficacy of the treatment.

Accordingly, practical and effective approaches for the therapeutic modulation of inhibitory KIRs have not been made available so far in the art.

SUMMARY OF THE INVENTION

This invention provides novel and useful human antibodies that specifically bind to KIR2DL1 and at least one of KIR2DL2 and KIR2DL3, or to all three of these KIRs, and/or human antibodies which potentiate NK-cell lytic activity by blocking the interactions between one or more such KIRs and HLA-C. Fragments and derivatives of such antibodies are also provided. The invention also pertains to novel and useful antibodies, antibody fragments, and derivatives of antibodies, which comprise VH and VL sequences substantially identical to those of human antibodies 1-7F9 and 1-4F1, as described herein. The invention also provides nucleic acids comprising nucleotide sequences encoding such antibodies; vectors comprising such nucleic acids; host cells and organisms comprising such nucleic acids and/or vectors; and compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The invention further provides various new and useful methods making and using such antibodies, nucleic acids, vectors, cells, organisms, and/or compositions, such as in the modulation of KIR-mediated biological activities, for example in the treatment of diseases related thereto.

In one aspect, the invention provides a human or humanized antibody that binds to each one of KIR2DL1, KIR2DL2, and KIR2DL3, but which does not bind to KIR2DS4. In one embodiment, the antibody further does not bind to KIR2DS3. In another embodiment, the human or humanized antibody blocks the binding of at least one of KIR2DL1, KIR2DL2, and KIR2DL3 to an HLA-C class I molecule. In a further embodiment, the antibody may block the binding of an HLA-Cw4 molecule to KIR2DL1, and the binding of an HLA-Cw3 molecule to at least one of KIR2DL2 or KIR2DL3. For example, the antibody may block the binding of an HLA-Cw4 molecule to residues M44, F45 and D72 of the extracellular portion of KIR2DL1 (SEQ ID NO:23). In yet another embodiment, the antibody potentiates the lytic activity of an NK cell against a human target cell expressing an HLA-C class I molecule.

In another aspect, the invention provides a human or humanized antibody that competes with an antibody comprising a light chain variable region comprising the amino acid sequence of SEQ ID NO:15, and a heavy chain variable region comprising the amino acid sequence of SEQ ID NO:17, in the binding to at least one of KIR2DL1, KIR2DL2, and KIR2DL3. In one embodiment, the antibody competes with an antibody comprising a light chain variable region comprising the amino acid sequence of SEQ ID NO:15, and a heavy chain variable region comprising the amino acid sequence of SEQ ID NO:17, in the binding to each of KIR2DL1, KIR2DL2, and KIR2DL3. In another embodiment, the antibody comprises a light chain variable region comprising the amino acid sequence of SEQ ID NO:15. In yet another embodiment, the antibody comprises (a) a heavy chain CDR1 amino acid sequence corresponding to residues 31-35 of SEQ ID NO:17; (b) a heavy chain CDR2 amino acid sequence corresponding to residues 50-65 of SEQ ID NO:17; and (c) a heavy chain CDR3 amino acid sequence corresponding to residues 99-112 of SEQ ID NO:17. For example, the antibody may comprise a heavy chain variable region comprising the amino acid sequence of SEQ ID NO:17.

In another aspect, the invention provides an isolated human or humanized antibody that binds to a KIR2DL1 epitope substantially comprising the amino acid residues L38, R41, M44, F45, N46, D47, T48, L49, R50, I52, F64, D72, Y80, P87, and Y88.

In another aspect, the invention provides an isolated human or humanized antibody that has a dissociation constant ($K_d$) for KIR2DL1 of no more than about 0.45 nM and/or a $K_d$ for KIR2DL3 of no more than about 0.025 nM.

The invention also provides a human or humanized antibody or antibody fragment, or a derivative thereof, which has any of the foregoing properties, alone or in any suitable combination. In one embodiment, the antibody is a monoclonal antibody. In another embodiment, the antibody is an IgG1, IgG2, IgG3, or IgG4 antibody. For example, the antibody may be an IgG4 antibody.

The invention also provides a nucleic acid encoding the human or humanized antibody or antibody fragment having any of the foregoing properties, a vector comprising such a nucleic acid, a cell comprising such a vector, and a method of producing a human anti-KIR antibody, comprising culturing such a cell under conditions suitable for expression of the anti-KIR antibody.

The invention also provides a pharmaceutical composition comprising a human or humanized antibody or antibody fragment having one or more of the foregoing properties or produced by any method, in an amount effective to detectably potentiate NK cell cytotoxicity in a patient, together with a pharmaceutically acceptable carrier or excipient. The composition may, for example, comprise Polysorbate 80, sucrose, or both Polysorbate 80 and sucrose.

The invention also provides a method of potentiating NK cell activity in a subject in need thereof, which method comprises administering to the subject an effective amount of any of the foregoing compositions. In one embodiment, the subject is a patient suffering from cancer. For example, the patient may be suffering from a cancer selected from acute myeloid leukaemia, chronic myeloid leukaemia, multiple myeloma, and non-Hodgkin's lymphoma. Alternatively, the patient may be suffering from a cancer selected from colorectal cancer, renal cancer, ovarian cancer, lung cancer, breast cancer, and malignant melanoma. In another embodiment, the subject is a patient suffering from an infectious disease. In yet another embodiment, the method further comprises administering a therapeutic agent selected from an immunomodulatory agent, a hormonal agent, a chemotherapeutic agent, an anti-angiogenic agent, an apoptotic agent, a second antibody that binds to an inhibitory KIR, an anti-infective agent, a targeting agent, and an adjunct compound.

It should be understood that description of antibodies "provided" by the invention or antibodies to which the invention "relates", etc., also, by implication, refers to antibodies that may be useful in practice of the inventive methods described herein, unless otherwise stated or clearly contradicted by context.

These and other aspects and features of the invention are described in further detail herein.

BRIEF DESCRIPTION OF THE DRAWINGS

FIG. 4 depicts reconstitution of cell lysis by NK cells that express KIR2DL1 against HLA-Cw4 positive target cells in the presence of F(ab')2 fragments of the DF200 and EB6 antibodies. (A) Target cells 721.221-Cw4; E/T ratio=1. (B) Target cells B-EBV cells expressing Cw4, E/T ratio=2.

FIG. 5 depicts induction of NK-mediated killing by cross-reactive murine (DF200 and NKVSF1 (Pan2D)) and human (1-7F9, 1-4F1, 1-6F5 and 1-6F1) mAbs, and a murine conventional KIR2DL1-specific mAb (EB6). The mAbs induce (reconstitute) killing by KIR2DL1-expressing NK cells (YTS-KIR2DL1) of 721.221 target cells transfected with HLA-Cw4. E/T ratio=1. (A) 30 µg/ml mAb. (B) 10 µg/ml mAb.

FIG. 6 depicts induction of NK-mediated killing by the same antibodies as in FIG. 5. The mAbs induce (reconstitute) killing by KIR2DL1-expressing NK cells (YTS-KIR2DL1) of B-EBV cells expressing endogenous HLA-Cw4. E/T ratio=2. (A) 30 µg/ml mAb. (B) 10 µg/ml mAb.

FIG. 11 shows the binding of soluble KIR2DL1 and KIR2DL1(R131W) mutant to cells. (A) Binding of increasing concentrations of soluble KIR2DL1-Fc, and a KIR2DL1 (R131W)-hFc mutant, to cells expressing HLA-Cw3 or -Cw4. The bound KIR-Fc proteins were detected using a secondary fluorochrome-conjugated antibody, and revealed by flow-cytometry. Mean fluorescence is shown on the y-axis. (B) Binding of the indicated anti-KIR mAbs (GL183, EB6, DF200, and Pan2D (NKVSF1)) to KIR2DL1-Fc and the 2DL1(R131W) mutant protein, using human Ig as control. The figure shows that DF200 and Pan2D (NKVSF1) bind less well to the mutant than the wild-type KIR2DL1-Fc, indicating that both mAbs are affected by the R131W mutation. Therefore, R131 is one of the residues constituting the epitope for DF200 and Pan2D on KIR2DL1.

FIG. 12 provides a comparative alignment of the amino acid sequences of the light chain variable regions, and light chain CDRs of antibodies DF200 and Pan2D (NKVSF1). (A) Alignment of anti-KIR variable light (VL) regions of DF200 (SEQ ID NO:1) and Pan-2D (SEQ ID NO:2). Numbers above amino acid sequences indicate position respective to initiation of translation Met (+1) in the immature (non-secreted) immunoglobulin. (B) Alignment of CDR-L1 sequences. Residue before: Normally Cys. Residues after: Trp. Typically Trp-Tyr-Leu.Length: 10-17 aa. (C) Alignment of CDR-L2 sequences. Residues before: Generally Ile-Tyr. Length: 7 aa. Start: approximately 16 aa after the end of CDR-L1. Start: approximately 24 aa from the beginning of secreted protein. (D) Alignment of CDR-L3 sequences. Residues before: Cys. Residues after: Phe-Gly-XXX-Gly. Length: 7-11 aa. Start: approximately 33 aa after the end of CDR-L2.

FIG. 13 provides the heavy chain variable region, and the heavy-chain CDRs of antibody DF200. (A) DF-200 VH region, immature protein. The secreted, mature VH starts at position 20: residue Q. The VH region ends with residue S and thereafter the constant region (not shown) continues. (B) CDR-H1. Residues before: Cys-XXX-XXX-XXX. Residues after: Trp. Generally Trp-Val or Trp-Ile. Length: 10-14 aa. Start: Approximately 22-26 aa from the beginning of the secreted protein. (C) CDR-H2. Residues before: Leu-Glu-Trp-Ile-Gly but other variations possible. Residues after: Lys or Arg/Leu or Ile or Val or Phe or Thr or Ala/Thr or Ser or Ile or Ala. Length: 16-20 aa. Start: Approximately 15 aa after the end of CDR-H1. (D) CDR-H3. Residues before: Cys-XXX-XXX (Typically Cys-Ala-Arg). Residues after: Trp-Gly-XXX-Gly. Length: 3-25 aa. Start: Approximately 33 after the end of CDR-H2.

FIG. 14 depicts the nucleotide and amino acid sequences of the VH and VL sequence of human antibody 1-7F9. (A) Translation of HuKIR 1-7F9 mature variable light chain. (B) Nucleotide sequence encoding HuKIR 1-7F9 mature variable light chain. (C) Translation of HuKIR 1-7F9 mature variable heavy chain. (D) Nucleotide sequence encoding HuKIR 1-7F9 mature heavy chain.

FIG. 18 depicts results of $^{51}$Cr-release cytotoxicity assays. (A) LCL 721.221-Cw3 cells are efficiently killed by both YTS cells (diamonds) and YTS-2DL1 cells (triangles) at various E:T ratios. In contrast, LCL 721.221-Cw4 cells are efficiently killed by YTS cells (squares), but can not be killed by YTS-2DL1 cells (crosses) due to KIR-restrictions. (B) In the absence of antibody, YTS-2DL1 cells cannot kill LCL-721.221-Cw4 (E:T ratio 12:1). 1-7F9 induces killing of LCL 721.221-Cw4 cells by YTS-2DL1 cells in a dose-dependent fashion.

FIG. 20 shows the binding epitope of 1-7F9 on KIR2DL1, as indicated in the KIR2DL1 sequence (SEQ ID NO: 23). Amino acids within 4.0 Å distance from 1-7F9 are highlighted in grey and black background. Amino acids highlighted by a black background are involved in hydrogen-bonding to 1-7F9.

DEFINITIONS

Figure 1:
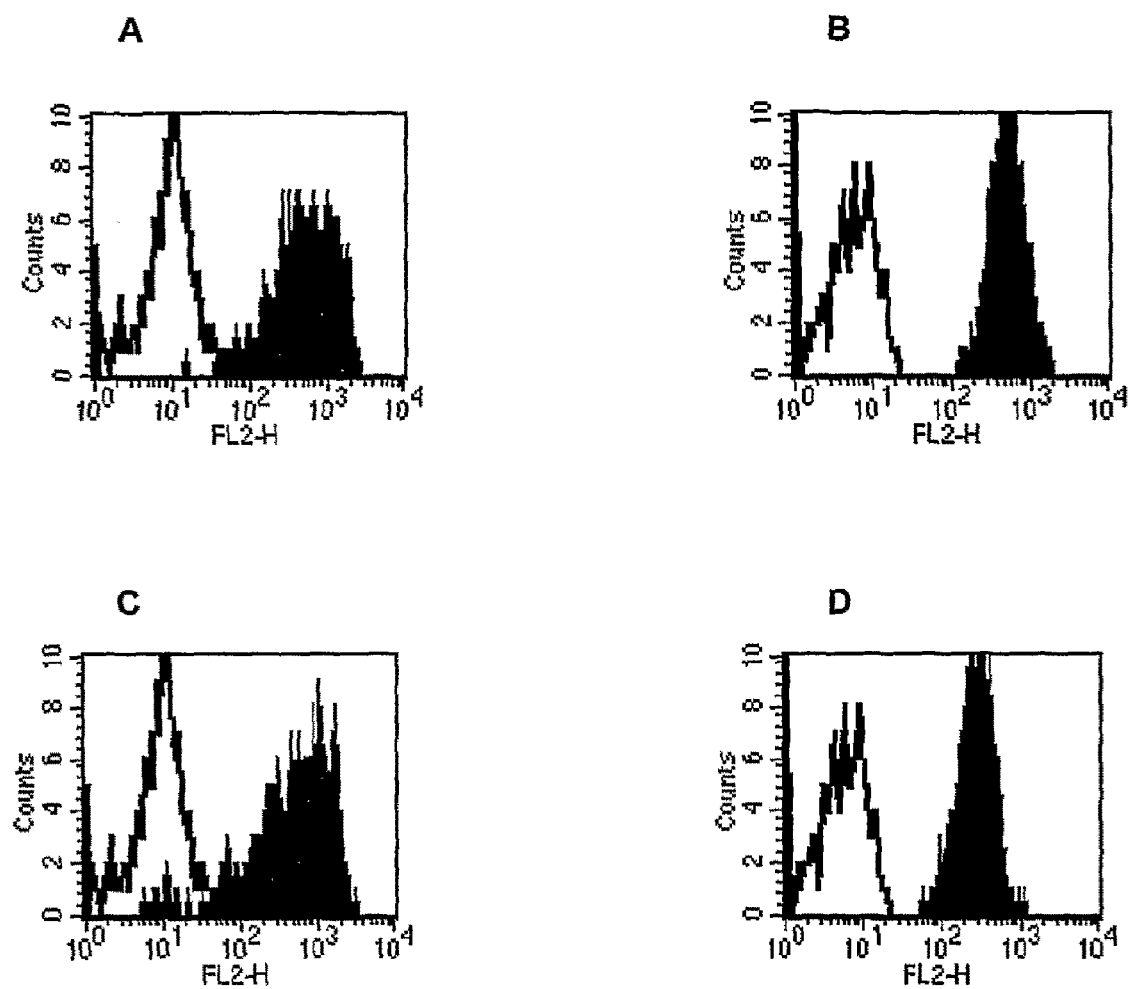
FIG. 1 depicts the murine monoclonal antibody DF200 binding to a common determinant of various human KIR2DL receptors. (A) Clone CP11, KIR2DL1+, DF200. (B) Clone CP502, KIR2DL3+. (C) Clone CP11, KIR2DL1+, Anti-KIR2DL1. (D) Clone CP502, KIR2DL3+, Anti-KIR2DL2/3.

For convenience, several terms are defined here. However, the list of defined terms provided here is not exclusive. Other terms may be defined throughout the description of the invention.

Within the context of this invention "active" NK cells designate biologically active NK cells, including NK cells having the capacity of lysing target cells or enhancing the immune function of other cells. For instance, an "active" NK cell can be able to kill cells that express a ligand for an activating NK receptor and/or fail to express MHC/HLA antigens recognized by a KIR on the NK cell. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

As used herein, a "Killer Ig-like Receptor", "Killer Inhibitory Receptor", or "KIR", refers to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is "The KIR Gene Cluster" by M. Carrington and P. Norman, available at the NCBI web-site called "Bookshelf" (accessible via the World-Wide Web (WWW) address ncbi.nlm.nih.gov/books). The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS1: Genbank accession number X89892; KIR2DS2: Genbank accession number L76667; KIR2DS3: Genbank accession number NM_012312 or L76670 (splice variant); KIR3DL1: Genbank accession number L41269; and KIR2DS4: Genbank accession number AAR26325. A KIR may comprise from 1 to 3 extracellular domains, and may have a long (i.e., more than 40 amino acids) or short (i.e., less than 40 amino acids) cytoplasmic tail. As previously described herein, these features determine the nomenclature of a KIR. Exemplary KIR2DL1, KIR2DL2, KIR2DL3, and KIR2DS4 molecules comprise the following respective amino acid sequences:

KIR2DL1 extracellular domain:
HEGVHRKPSLLAHPGXLVK-SEETVILQCWSDVMFEHFLLHREGM-FNDTLRLIGEHHD GVSKANFSISRMTQDLAGTYR-CYGSVTHSPYQVSAPSDPLDIVIIGLYEKPSLSAQXG-PTVLAG ENVTLSCSSRSSYDMYHLSREGEAHER-RLPAGPKVNGTFQADFPLGPATHGGTYRCFGSFHD SPYEWSKSSDPLLVSVTGNPSN-SWPSPTEPSSKTGNPRHLH (SEQ ID NO:23), where "X" at position 16 is P or R, and where "X" at position 114 is P or L, representing allelic variants.

```
KIR2DL2 extracellular domain:
    HEGVHRKPSLLAHPGRLVKSEETVILQCWSDVRFEHFLLHREGKFKDTLHLIGEHHDG    (SEQ ID NO: 24)

VSKANFSIGPMMQDLAGTYRCYGSVTHSPYQLSAPSDPLDIVITGLYEKPSLSAQPGPTVLAGE

SVTLSCSSRSSYDMYHLSREGEAHECRFSAGPKVNGTFQADFPLGPATHGGTYRCFGSFRDS

PYEWSNSSDPLLVSVIGNPSNSWPSPTEPSSKTGNPRHLH

KIR2DL3 extracellular domain:
    HEGVHRKPSLLAHPGPLVKSEETVILQCWSDVRFQHFLLHREGKFKDTLHLIGEHHDG    (SEQ ID NO: 25)

VSKANFSIGPMMQDLAGTYRCYGSVTHSPYQLSAPSDPLDIVITGLYEKPSLSAQPGPTVLAGE

SVTLSCSSRSSYDMYHLSREGEAHERRFSAGPKVNGTFQADFPLGPATHGGTYRCFGSFRDS

PYEWSNSSDPLLVSVTGNPSNSWPSPTEPSSETGNPRHLH.

KIR2DS4 extracellular domain:
    QEGVHRKPSFLALPGHLVKSEETVILQCWSDVMFEHFLLHREGKFNNTLHLIGEHHDG    (SEQ ID NO: 38)

VSKANFSIGPMMPVLAGTYRCYGSVPHSPYQLSAPSDPLDMV.
```

The term "KIR2DL2/3" refers to either or both of the KIR2DL2 and KIR2DL3 receptors. These two receptors have a very high homology, they are allelic forms of the same gene, and are considered by the art to be functionally similar.

Unless otherwise specified, term "MHC" encompasses MHC molecules in all mammals, whereas an "HLA" molecule refers to a human MHC molecule.

Within the context of this invention, stating that an antibody "binds" a determinant (i.e., the word "bind" in the context of antibody:determinant interaction) designates that the antibody binds the determinant with specificity_and/or affinity. For example, GL183 is a conventional monoclonal antibody that binds to KIR2DL2/3. EB6 is a conventional monoclonal antibody that binds to KIR2DL1. EB6 and GL183 are both commercially available (Beckman Coulter Inc., Fullerton, Calif.).

A "cross-reactive" anti-KIR antibody is an antibody that binds more than one KIR molecule with specificity and/or affinity. For example, DF200 and 1-7F9 are monoclonal antibodies cross-reactive with KIR2DL1, -2, and -3. The hybridoma producing antibody DF200 has been deposited at the CNCM culture collection, under identification no. "DF200", registration no. CNCM I-3224, registered 10 Jun. 2004, Collection Nationale de Cultures de Microorganismes, Institut Pasteur, 25, Rue du Docteur Roux, F-75724 Paris Cedex 15, France. NKVSF1, also referred to as "Pan2D" herein, is cross-reactive with KIR2DL1, -2, and -3 and KIR2DS4. This antibody is commercially available from Serotec (Cergy Sainte-Christophe, France), Catalog ref no. MCA2243.

"Specific binding" or "specificity" refers to the ability of an antibody or other agent to detectably bind an epitope presented on an antigen, such as a KIR, while having relatively little detectable reactivity with other proteins or structures (such as other proteins presented on NK cells, or on other cell types). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a KIR). A KIR-binding antibody, specific for a KIR presented on the NK cells of a particular organism, such as a human, can sometimes exhibit binding to similar KIRs of other species (i.e., a KIR-binding antibody, or other KIR-binding agent, may cross-react with KIRs of various species).

"Selectivity" refers to the preferential binding of a protein to a particular region, target, or peptide as opposed to one or more other biological molecules, structures, cells, tissues, etc. A KIR-binding antibody can also be selective for a KIR produced in a particular organism (e.g., in a human as opposed to in a primate), and/or for a particular type of KIR (e.g., a KIR with a long cytoplasmic tail), particularly where the antibody cross-reacts with more than one type of KIR produced in a particular organism, and/or a particular portion of a KIR (such as a particular epitope or antigenic determinant region). For example, selectivity can be determined by competitive ELISA or Biacore assays. The difference in affinity/avidity that marks selectivity can be any detectable preference (e.g., a ratio of more than 1:1.1, or more than about 1:5, if detectable, would be suitable, including 1:10, 1:100, 1:1000 or more). Unless otherwise specified, any quantitative data on "affinity" presented herein refers to measurements of bivalent (as opposed to monovalent) binding.

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the "footprint" of the specifically antigen binding peptide). The term epitope herein includes both types of amino acid binding sites in any particular region of a KIR that specifically binds to an anti-KIR antibody, or another KIR-specific agent according to the invention, unless otherwise stated (e.g., in some contexts the invention relates to antibodies that bind directly to particular amino acid residues). KIRs may comprise a number of different epitopes, which may include, without limitation, (1) linear peptide antigenic determinants, (2) conformational antigenic determinants which consist of one or more non-contiguous amino acids located near each other in a mature KIR conformation; and (3) post-translational antigenic determinants which consist, either in whole or part, of molecular structures covalently attached to a KIR, such as carbohydrate groups.

The phrase that a first antibody binds "substantially" or "at least partially" the same epitope as a second antibody means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same epitope as a second antibody means that the first and second antibodies compete in binding to the antigen, as described above. Thus, the term "binds to substantially the same epitope or determinant as" the monoclonal antibody 1-7F9 means that an antibody "competes" with 1-7F9. Generally, an antibody that "binds to substantially the same epitope or determinant as" the monoclonal antibody of interest (e.g. DF200, NKVSF1, 1-7F9) means that the antibody "competes" with said antibody of interest for binding to one or more KIR molecules, preferably a KIR molecule selected from the group consisting of KIR2DL1 and KIR2DL2/3. In other examples, an antibody that binds to substantially the same epitope or determinant on a KIR2DL1 molecule as the antibody of interest "competes" with the antibody of interest for binding to KIR2DL1. An antibody that binds to substantially the same epitope or determinant on a KIR2DL2/3 molecule as the antibody of interest "competes" with the antibody of interest for binding to KIR2DL2/3.

The phrase "binds to essentially the same epitope or determinant as" an antibody of interest means that an antibody "competes" with said antibody of interest for at least one, or for any and all KIR molecules to which said antibody of interest specifically binds. The phrase "binds to essentially the same epitope or determinant as" the monoclonal antibody 1-7F9 means that an antibody "competes" with 1-7F9 for at least one, preferably any and all KIR molecules, to which 1-7F9 specifically binds. For example, an antibody that binds to essentially the same epitope or determinant as the monoclonal antibodies 1-7F9 or NKVSF1 can "compete" with said 1-7F9 or NKVSF1 respectively for binding to KIR2DL1, KIR2DL2/3, KIR2DS1 and KIR2DS2.

The ability of an anti-KIR antibody to "block" the binding of a KIR molecule and an HLA molecule means that the antibody, in an assay using soluble or cell-surface associated KIR and HLA molecules, can detectably reduce the binding of a KIR-molecule to an HLA molecule in a dose-dependent fashion, where the KIR molecule detectably binds to the HLA molecule in the absence of the antibody. An exemplary assay for determining whether an anti-KIR antibody is capable of such blocking is provided in Example 8.

The ability of an anti-KIR antibody to "reduce the inhibitory activity of a KIR", "facilitate NK cell activity," "facilitate NK cell cytotoxicity," "facilitate NK cells," "potentiate NK cell activity," "potentiate NK cell cytotoxicity," or "potentiate NK cells" means that an NK cell expressing a KIR, when contacted with the antibody, is capable of lysing target cells that express on their surface a particular MHC or HLA class I which is a ligand for said KIR. For example, the term "potentiation in NK cytotoxicity" means any substantial potentiation, or at least 5%, 10%, 20%, 30% or greater potentiation in NK cytotoxicity, e.g. at least about 50% potentiation of NK cytotoxicity (e.g., at least about 60%, at least about 70%, at least about 80%, at least about 85%, at least about 90%, or at least about 95% as compared to a control. This includes, for example, about 55-100%, about 65-100%, about 75-100%, about 80-100%, or about 90-100% potentiation of NK cell cytotoxicity, as compared to a control. It also includes more than about 100%, more than about 500%, more than about 1000%, more than about 2000%, or higher increase in the cytotoxicity. This can be measured in, e.g., an assay, such as a standard cytotoxicity assay, where a higher number, amounting to a higher percentage, of target cells are lysed by NK cells in the presence of an NK potentiator (such as an anti-KIR mAb) than in the absence of the potentiator (i.e., the control).

The term "neutralize KIR-mediated inhibition of NK cell cytotoxicity" or "neutralize the inhibitory activity of a KIR," as used herein means the ability to increase specific lysis to more than about 20%, preferably with at least about 30%, at least about 40%, at least about 50%, at least about 100%, or more of the specific lysis obtained at the same effector:target cell ratio with NK cells or NK cell lines that are not blocked by their KIR, as measured by a classical chromium release test of cytotoxicity. "Neutralize KIR mediated inhibition" can also mean that in a chromium-release assay, or other cytotoxicity assay, using an NK cell clone or transfectant expressing one or several inhibitory KIRs and a target cell expressing at least one HLA class I allele that is recognized by one of the KIRs on the NK cell, the specific lysis obtained with the antibody is more than about 100%, preferably at least about 101%, at least about 150%, at least about 200%, or more (e.g., about 101-150%, about 120-150%, about 120-200%, about 150-200%, or about 200-1000%), or more of the specific lysis obtained with the same concentration of NKVSF1 (commercially available from Serotec), using the same NK cells and target cells, at the same effector:target cell ratio.

The term "human antibody", as used herein, is intended to include antibodies having variable and constant regions identical to, essentially identical to, or derived from human germline immunoglobulin sequences. Such human antibodies can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

In the context of the present invention, unless otherwise stated, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive therapy, whereas "treatment" of a patient in whom symptoms or clinically relevant manifestations of a disease or disorder have been identified generally does not constitute preventive therapy. Nonetheless, it should be understood that the various therapeutic and prophylactic method and use facets of the invention are distinct from one in many respects (e.g., dosage of compound(s) to be delivered to a subject, timing of application, impetus for application, etc.) and may each be considered a unique facet of the invention.

In the context of the present invention "cancer" refers to any neoplastic disorder, including, but not limited to, such cellular disorders as sarcoma, carcinoma, melanoma, leukaemia, and lymphoma, which may include cancers in the breast, head and neck, ovaries, bladder, lung, pharynx, larynx, oesophagus, stomach, small intestines, liver, pancreas, colon, female reproductive tract, male reproductive tract, prostate, kidneys and central nervous system.

The term "biological sample" as used herein includes but is not limited to a biological fluid (for example serum, lymph, and blood), cell sample or tissue sample (for example bone marrow or tumor tissue) derived from a human or non-human mammal.

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions (further described elsewhere herein). Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA, applying default or recommended parameters. A program in GCG Version 6.1, FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, using default parameters.

A "1-7F9-like" or "1-4F1-like" antibody as used herein means (1) an antibody that binds substantially the same epitope as an antibody comprising the VH and VL sequences of 1-7F9 or 1-4F1, respectively, such as, e.g., monoclonal antibody 1-7F9 or 1-4F1, respectively, and/or (2) an antibody comprising VH and VL sequences identical or substantially identical to the VH and VL sequences of 1-7F9 or 1-4F1, respectively.

A "conservative" amino acid substitution is one in which an amino acid residue is substituted by another amino acid residue having a side chain ("R-group") with similar chemical properties (e.g., charge or hydrophobicity). In general, a conservative amino acid substitution will not substantially change the functional properties of a protein. In cases where amino acid sequences differ from each other by conservative substitutions, the percent sequence identity may be adjusted upwards to correct for the conservative nature of the substitution. Means for making this adjustment are well-known to those of skill in the art. See, e.g., Pearson, Methods Mol. Biol. 1994; 243:307-31. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Exemplary conservative amino acids substitution groups include: valine-leucine-isoleucine, phenylalanine-tyrosine, lysine-arginine, alanine-valine, glutamate-aspartate, and asparagine-glutamine.

DESCRIPTION OF THE INVENTION

This invention is based on the generation of novel cross-reactive and neutralizing antibodies binding to inhibitory KIRs, the antibodies allowing effective activation of NK cells in most or all individuals in human populations.

Described herein are, for example, antibodies that bind to all of KIR2DL1, KIR2DL2, and KIR2DL3 and potentiate NK-cell lytic activity by blocking the interactions between these KIRs and HLA-C. Such antibodies are referred to herein as "cross-reactive and neutralizing anti-KIR mAbs".

In a particular aspect, the present invention relates to novel cross-reactive, neutralizing, or both crossreacting and neutralizing, fully human anti-KIR antibodies, as well as compositions comprising such antibodies and methods of using such antibodies or compositions. These antibodies include human antibodies 1-7F9 and 1-4F1, described in PCT/DK2004/000470, filed on Jul. 1, 2004, which is hereby incorporated by reference in its entirety.

Antibodies, compositions, and methods described herein may, among other things, overcome current limitations associated with therapeutic modulation of KIR, and with therapeutic NK cell activation, and provide additional advantageous features and benefits. For example, the antibodies can cross-react with multiple inhibitory KIRs and reduce or neutralize their inhibitory signals, resulting in potentiation of NK cell cytotoxicity by NK cells expressing such inhibitory KIR receptors. The ability to cross-react with multiple KIR gene products can allow the antibodies of the invention to be effectively used to increase NK cell activity in most or all human subjects, without the burden or expense of pre-determining the KIR or HLA type of the subject. In one embodiment, the antibodies do not bind KIR2DS4, thus avoiding the reduction in stimulatory potential that would be associated with neutralization of the activating KIR2DS4 receptor. Additionally or alternatively, the antibodies do not bind KIR2DS3.

From such antibodies, various antibody fragments and derivatives can also be generated and used for the same or similar purposes as are described herein with respect to the antibodies of the invention, and aspects of the invention described with respect to antibodies apply equally to antibody fragments and derivatives, unless otherwise stated or clearly contradicted by context. In other words, a feature of the invention described herein with respect to an antibody should, unless otherwise indicated, also implicitly be understood to describe a similar feature with respect to an antibody fragment or derivative having similar functionality in terms of specificity. It should be recognized, however, that "full-length" antibodies and antibody "fragments" can be characterized as distinct aspects of the invention, inasmuch as their biological and physiochemical properties may differ significantly.

the antibody once administered to a subject. Furthermore, both 1-7F9 and 1-4F1 are of suitable isotypes for therapeutic anti-KIR antibodies (IgG4 and IgG2, respectively), as described below. 1-7F9 is also more effective at inducing killing by NK cells that express either KIR2DL1, -2, and/or -3 than murine mAbs EB6, GL183, DF200, and NKVSF1 (Pan2D). For example, as shown in FIGS. 5 and 6, 1-7F9 induced higher levels of specific lysis by KIR2DL1-expressing NK cells of target cells that expressed HLA-Cw4 than did EB6, DF200 or NKVSF1 (Pan2D). 1-7F9 further has a higher affinity for KIR compared to previously known anti-KIR mAbs. For example, 1-7F9 binds to KIR2DL1 and KIR2DL3 with dissociation constants ($K_d$'s) of 0.43 nM and 0.025 nM, respectively, representing a higher affinity for both antigens than, for example, DF200 (see Examples 3 and 8). As opposed to the murine antibodies NKVSH (Pan2D), A210, and A208g, none of 1-7F9 and 1-4F1 binds to KIR2DS4, making them better suited for therapeutic purposes. Like NKVSF1 (Pan2D) and DF200, 1-7F9 and 1-4F1 also bind to KIR2DS1 and KIR2DS2, but KIR2DS1 and KIR2DS2 are not believed to be important in anti-leukemia efficacy. Particular antibodies according to the invention therefore have the same or similar antigen-specificities as 1-7F9 and/or 1-4F1. For example, antibodies comprising the same or similar VH and VL regions as 1-7F9 can have the same or similar antigen-binding and/or NK-stimulatory properties as 1-7F9; and antibodies comprising the same or similar VH and VL regions as 1-4F1 can have the same or similar antigen-binding properties as 1-4F1.

As shown in FIG. 14, the amino acid sequences of the VL and VH regions of 1-7F9 have been determined:

```
1-7F9 VL region (SEQ ID NO: 15):
    EIVLTQSPVTLSLSPGERATLSCRASQSVSSYLAWYQQKPGQAPRLLIYDASNRATGI

PARFSGSGSGTDFTLTISSLEPEDFAVYYCQQRSNWMYTFGQGTKLEIKRT 1-7F9 VH region (SEQ ID NO: 17):
    QVQLVQSGAEVKKPGSSVKVSCKASGGTFSFYAISWVRQAPGQGLEWMGGFIPIFG

AANYAQKFQGRVTITADESTSTAYMELSSLRSDDTAVYYCARIPSGSYYYDYDMDVWGQGTT

VTVSS
```

Some antibodies of the invention can be characterized as "human", which are typically associated with a lower risk for an immune response against the antibodies by a human subject to whom they are administered. In one exemplary aspect, an isolated antibody that facilitates the activation of human NK cells in virtually all humans is described. In an exemplary embodiment, the antibody is human antibody 1-7F9 or a human 1-7F9-like antibody.

Antibodies, fragments, or derivatives of either thereof can cross-react with at least two inhibitory KIR receptors at the surface of NK cells, reduce or neutralize the inhibitory signals of the NK cells, and potentiate the activity of the NK cells. For example, an antibody, antibody fragment, or derivative may bind a common determinant of human KIR2DL receptors, so that the antibody, antibody fragment, or derivative binds at least KIR2DL1, KIR2DL2, and KIR2DL3 receptors. For the purposes of this invention, the term "KIR2DL2/3" refers to either or both of the KIR2DL2 and KIR2DL3 receptors.

As described herein, the anti-KIR mAbs 1-7F9 and 1-4F1 have several advantages over previously produced anti-KIR antibodies. For example, 1-7F9 and 1-4F1 are fully human, thus reducing or minimizing any immune response against The amino acid sequences of the 1-4F1 VL and VH regions are provided in SEQ ID NOS: 39 and 41, respectively, and the nucleotide sequences encoding the 1-4F1 VL and VH regions are provided in SEQ ID NOS:40 and 42, respectively. In a particular embodiment, residues 3, 4, 9, 24, 32, 41, 47, 50, 55, 71, and 74 of SEQ ID NO:39 are Q, L, S, R, A, G, L, D, E, F, and A, respectively. In another particular embodiment, residues 3, 4, 9, 24, 32, 41, 47, 50, 55, 71, and 74 of SEQ ID NO:39 are R, M, F, W, Y, A, F, Y, Q, Y, and T, respectively.

Figure 15:
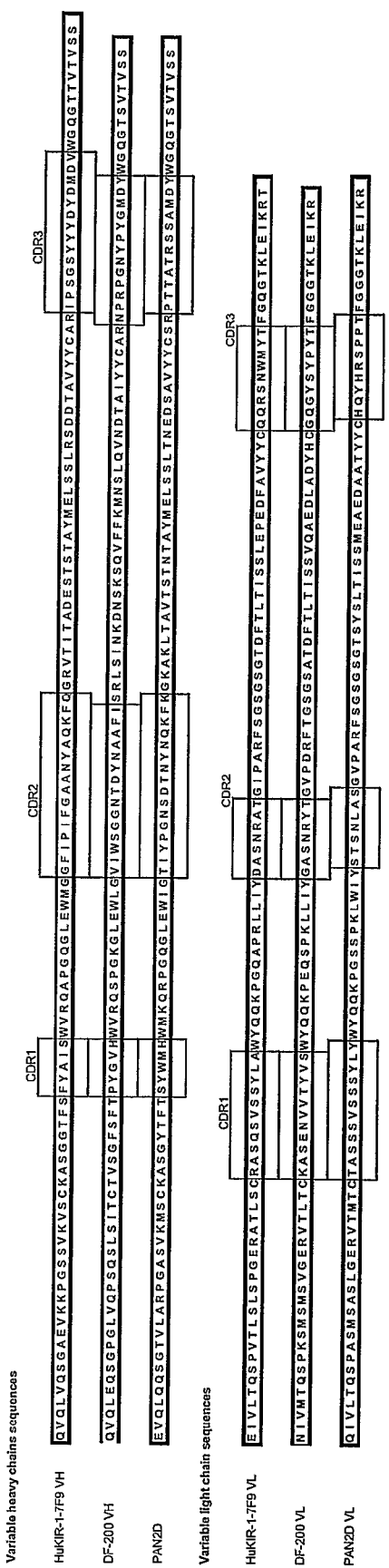
FIG. 15 shows the amino acid sequences of the VH and VL sequences of monoclonal antibodies 1-7F9, DF200 (VH sequence: SEQ ID NO:19; VL sequence: SEQ ID NO:21), and Pan2D (NKVSF1; VH sequence: SEQ ID NO:20; VL sequence: SEQ ID NO:22). The CDRs are boxed.

As shown in FIG. 15, the amino acid sequences of the 1-7F9 CDRs have been identified as follows: the light chain CDR1 amino acid sequence corresponds to residues 24-34 of SEQ ID NO:15; the light chain CDR2 amino acid sequence corresponds to residues 50-56 of SEQ ID NO:15; the light chain CDR3 amino acid sequence corresponds to residues 89-97 of SEQ ID NO:15; the heavy chain CDR1 amino acid sequence corresponds to residues 31-35 of SEQ ID NO:17; the heavy chain CDR2 amino acid sequence corresponds to residues 50-65 of SEQ ID NO:17; and the heavy chain CDR3 amino acid sequence corresponds to residues 99-112 of SEQ ID NO:17. The amino acid sequences of the 1-4F1 CDRs have been identified as follows: the light chain CDR1 amino acid sequence corresponds to residues 24-34 of SEQ ID NO:39; the light chain CDR2 amino acid sequence corresponds to residues 50-56 of SEQ ID NO:39; the light chain CDR3 amino acid sequence corresponds to residues 89-97 of SEQ ID NO:39; the heavy chain CDR1 amino acid sequence corresponds to residues 31-35 of SEQ ID NO:41; the heavy chain CDR2 amino acid sequence corresponds to residues 50-66 of SEQ ID NO:41; and the heavy chain CDR3 amino acid sequence corresponds to residues 99-113 of SEQ ID NO:41.

Amino acid sequences for the entire 1-7F9 light and heavy chains are provided in SEQ ID NOS:36 and 37, respectively.

Accordingly, additional antibodies of, for example, various human antibody subclasses; antibody fragments, antibody derivatives, and other KIR-binding peptides, can be readily produced by, e.g., recombinant techniques, based upon this information. For example, in one aspect, the invention provides an antibody having a VL and a VH sequence consisting essentially of SEQ ID NO:15 and SEQ ID NO:17, respectively, and/or an antibody having a VL and a VH sequence consisting essentially of SEQ ID NO:39 and SEQ ID NO:41, respectively. In another aspect, the invention provides an antibody comprising CDR regions consisting essentially of the 1-7F9 or 1-4F1 VH CDR1-3 and VL CDR1-3 described above. In another aspect, the invention provides an antibody comprising CDR regions as follows: a light chain CDR1 amino acid sequence corresponding to about residues 24-34 of SEQ ID NO:15; the light chain CDR2 amino acid sequence corresponding to about residues 50-56 of SEQ ID NO:15; the light chain CDR3 amino acid sequence corresponding to about residues 89-97 of SEQ ID NO:15; the heavy chain CDR1 amino acid sequence corresponding to about residues 31-35 of SEQ ID NO:17; the heavy chain CDR2 amino acid sequence corresponding to about to residues 50-65 of SEQ ID NO:17; and the heavy chain CDR3 amino acid sequence corresponding to about residues 99-112 of SEQ ID NO:17. In another aspect, the invention provides an antibody comprising CDR regions as follows: a light chain CDR1 amino acid sequence corresponding to about residues 24-34 of SEQ ID NO:39; a light chain CDR2 amino acid sequence corresponding to about residues 50-56 of SEQ ID NO:39; a light chain CDR3 amino acid sequence corresponding to about residues 89-97 of SEQ ID NO:39; a heavy chain CDR1 amino acid sequence corresponding to about residues 31-35 of SEQ ID NO:41; a heavy chain CDR2 amino acid sequence corresponding to about residues 50-66 of SEQ ID NO:41; and a heavy chain CDR3 amino acid sequence corresponding to about residues 99-113 of SEQ ID NO:41. In another aspect, the invention provides an antibody comprising a light chain CDR1 amino acid sequence consisting essentially of residues 24-34 of SEQ ID NO:15; a light chain CDR2 amino acid sequence consisting essentially of residues 50-56 of SEQ ID NO:15; a light chain CDR3 amino acid sequence consisting essentially of residues 89-97 of SEQ ID NO:15; a heavy chain CDR1 amino acid sequence consisting essentially of residues 31-35 of SEQ ID NO:17; a heavy chain CDR2 amino acid sequence consisting essentially of residues 50-65 of SEQ ID NO:17; and a heavy chain CDR3 amino acid sequence consisting essentially of residues 99-112 of SEQ ID NO:17. In another aspect, the invention provides an antibody comprising CDR regions as follows: a light chain CDR1 amino acid sequence consisting essentially of residues 24-34 of SEQ ID NO:39; a light chain CDR2 amino acid sequence consisting essentially of residues 50-56 of SEQ ID NO:39; a light chain CDR3 amino acid sequence consisting essentially of residues 89-97 of SEQ ID NO:39; a heavy chain CDR1 amino acid sequence consisting essentially of residues 31-35 of SEQ ID NO:41; a heavy chain CDR2 amino acid sequence consisting essentially of residues 50-66 of SEQ ID NO:41; and a heavy chain CDR3 amino acid sequence consisting essentially of residues 99-113 of SEQ ID NO:41.

The invention also encompasses an anti-KIR antibody, antibody fragment, or antibody derivative, or a KIR-binding polypeptide, comprising at least one variant amino acid sequence substantially identical to the 1-7F9 or 1-4F1 VH or VL sequence, or to a CDR-region therein. A variant amino acid sequence can comprise or consist essentially of an amino acid sequence that is at least about 50, 80, 90, 95, 98, or 99 (e.g., about 50-99, about 65-99, about 75-99, or about 85-99) percent identical to a 1-7F9 or 1-4F1 CDR, VH, or VL region. A variant amino acid sequence can also or alternatively comprise 1, 2, or 3 CDRs that comprise or consist of amino acid sequences that are at least about 80%, at least about 90%, or at least about 95% identical to 1-7F9 or 1-4F1 CDRs. Thus, in one aspect, the invention provides a human antibody comprising a light chain CDR1 amino acid sequence at least about 80%, at least about 90%, or at least about 95% identical to residues 24-34 of SEQ ID NO:15 or SEQ ID NO:39; a light chain CDR2 amino acid sequence at least about 80%, at least about 90%, or at least about 95% identical to residues 50-56 of SEQ ID NO:15 or SEQ ID NO:39; a light chain CDR3 amino acid sequence at least about 80%, at least about 90%, or at least about 95% identical to residues 89-97 of SEQ ID NO:15 or SEQ ID NO:39; a heavy chain CDR1 amino acid sequence at least about 80%, at least about 90%, or at least about 95% identical to residues 31-35 of SEQ ID NO:17 or SEQ ID NO:41; a heavy chain CDR2 amino acid sequence at least about 80%, at least about 90%, or at least about 95% identical to residues 50-65 of SEQ ID NO:17 or to residues 50 to 66 of SEQ ID NO:41; and a heavy chain CDR3 amino acid sequence at least about 80%, at least about 90%, or at least about 95% identical to residues 99-112 of SEQ ID NO:17 or to residues 99 to 113 of SEQ ID NO:41. The basic properties of 1-7F9- or 1-4F1-derived KIR-binding amino acid sequences that are retained in such variant amino acid sequences desirably include the specificity and/or avidity of the 1-7F9 or 1-4F1 sequence for one or more KIRs, and may also or alternatively include the capability of 1-7F9 in blocking KIR/HLA-C interaction and potentiating the lytic activity of NK cells.

In another aspect, the invention provides an anti-KIR antibody, antibody fragment, or antibody derivative, or a KIR-binding polypeptide, that comprises a KIR-binding amino acid sequence that differs from a 1-7F9 or 1-4F1 KIR-binding sequence in one or more amino acid residues (e.g., at least 2, 3, 5, at least about 10, at least about 15, at least about 20, at least about 25, at least about 30, at least about 35, at least about 40, at least about 50, or more amino acid residues) by way of one or more residue insertions, deletions, and/or substitutions. In one embodiment, such a variant KIR-binding sequence confers greater affinity; greater or different specificity; less immunogenicity (in terms of host response to the sequence); greater in vivo stability; and/or other beneficial properties to the variant sequence over an essentially identical amino acid sequence comprising the native 1-7F9 or 1-4F1 sequence. Suitable sequence variations are further described elsewhere herein. A KIR-binding portion of an anti-KIR antibody, antibody fragment, or antibody derivative, or a KIR-binding polypeptide, can also comprise any suitable number of non-amino acid components or substituents, such as non-amino acid organic moieties, that facilitate KIR binding and/or provide other advantageous physiochemical or immunological properties.

Some antibodies of the invention can also or alternatively be characterized by their binding affinity to one or more KIRs. For example, as shown in Examples 3 and 8, in terms of bivalent binding, DF200 has a $K_d$ for KIR2DL1 of about 11 nM, and a $K_d$ for KIR2DL3 of about 2.0 nM, and 1-7F9 has a $K_d$ for KIR2DL1 of about 0.43 nM, and a $K_d$ for KIR2DL3 of about 0.025 nM. Accordingly, in one aspect, the invention provides human or non-human (e.g., murine, chimeric, or humanized) antibodies having a $K_d$ in bivalent binding to KIR2DL1 of no more than about 20 nM, no more than about 11 nM, no more than about 5 nM, no more than about 1 nM, no more than about 0.5 nM, or no more than about 0.43 nM. Additionally or alternatively, human or non-human (e.g., murine, chimeric, or humanized) antibodies of the invention may have a $K_d$ for KIR2DL3 of no more than about 20 nM, no more than about 2 nM, no more than about 1 nM, no more than about 0.1 nM, or no more than about 0.05 nM, or no more than about 0.025 nM. In a particular aspect, the antibodies have about the same $K_d$ values for bivalent binding to KIR2DL1 and KIR2DL3 as 1-7F9. As shown in Example 13, in terms of monovalent binding, 1-7F9 and 1-4F1 have $K_d$-values for KIR2DL3 of about 3.5 and 7 nM, respectively. Accordingly, in one aspect, the invention provides human or non-human (e.g., murine, chimeric, or humanized) antibodies having a $K_d$ in monovalent binding to KIR2DL3 of no more than about 20 nM, no more than about 10 nM, no more than about 7 nM, or no more than about 3.5 nM.

An anti-KIR antibody, antibody fragment, or antibody derivative, or a KIR-binding polypeptide selectively and/or specifically (typically specifically) binds at least one KIR, and more particularly an antigenic determinant region or epitope of at least one KIR, under appropriate conditions (e.g., with respect to temperature, pH, etc., which typically will reflect human physiological conditions in a normal or NK cell-associated disease state, and in the context of a suitable protein comprising the sequence or combination). For example, in one aspect, the invention relates to antibodies that can be characterized in (among other things) the ability to compete with 1-7F9, 1-4F1 or a 1-7F9- or 1-4F1-like antibody, and various methods involving the same. Other antibodies of the invention (and/or that are useful in the practice of inventive methods described herein) also or alternatively can be characterized on having the ability to compete with one or more of antibody DF200, antibody NKVSF1, antibody EB6, and antibody GL183.

The cross-reactive and neutralizing anti-KIR antibodies, antibody fragments, or derivatives of the invention reduce or neutralize the inhibitory activity of KIR by specifically inhibiting binding of MHC and/or HLA molecules to at least two inhibitory KIR receptors and facilitating NK cell activity, meaning that such antibodies, fragments or derivatives permit NK cells expressing an inhibitory KIR receptor on their surface to be capable of lysing cells that express a corresponding HLA ligand for that particular inhibitory KIR receptor (e.g., a particular HLA antigen). In one aspect, the invention provides antibodies that specifically inhibit the binding of HLA-C molecules to KIR2DL1 and KIR2DL2/3 receptors. In another aspect, the invention provides antibodies that inhibit the binding of KIR2DL1 and/or KIR2DL2/3 to HLA-C. In yet another aspect, the invention provides antibodies that facilitate NK cell activity in vivo, and/or in vitro.

At least one of KIR2DL1 or KID2DL2/3 is present in at least about 90% or more of the human population, and the more preferred antibodies of this invention are capable of potentiating the activity of NK cells expressing either or both of these KIR. Therefore, compositions of this invention may be used to effectively activate or potentiate NK cells in most human individuals, typically in about 90% of human individuals or more. Accordingly, a single antibody composition according to the invention may be used to treat most human subjects, and there is seldom need to determine KIR- or HLA-allelic groups or to use mixtures or cocktails of two or more anti-KIR mAbs.

In one aspect, the antibody specifically binds both KIR2DL1 and KIR2DL2/3 human receptors and reverses inhibition of NK cell cytotoxicity mediated by these KIRs. The antibody may also be human and compete with monoclonal antibody 1-7F9 and/or 1-4F1. The term "competes with" when referring to a particular pair of antibodies (e.g., one or more antibodies selected from DF200, NKVSF1 (Pan2D), 1-7F9, EB6, and GL183), means that a first antibody detectably competes with a second antibody (or other molecule) in a binding assay using either recombinant KIR molecules or cell-surface expressed KIR molecules. For example, in one aspect, where the percentages of inhibition for a certain antibody pair are above about 20%, above about 30%, above about 40%, above about 50%, regardless of which antibody is used as first antibody, the antibodies compete. Alternatively, if the percentages of inhibition for a certain antibody pair average at least about 29%, at least about 30%, at least about 40%, or at least about 50%, the antibodies compete. The percentage of inhibition of a second antibody binding to KIR2D protein by a first antibody can be calculated as: 100*(1−(detected binding second antibody)/(detected binding of first antibody)). The same applies to antibody fragments and antibody derivatives. Unless otherwise specified, an antibody that "competes" with 1-7F9, 1-4F1 or a 1-7F9- or 1-4F1-like antibody may compete with 1-7F9, 1-4F1 or the 1-7F9- or 1-4F1-like antibody for binding to human KIR2DL1, human KIR2DL2/3, or both human KIR2DL1 and KIR2DL2/3. For example, the antibody DF200 competes with 1-7F9 and 1-4F1 for binding to KIR2DL3.

Optionally, an antibody which competes with 1-7F9 or 1-4F1 is not 1-7F9 or 1-4F1 themselves, respectively (i.e., the invention provides antibodies other than 1-7F9 and 1-4F1 that are characterized by, among other things, the ability to compete with 1-7F9 and/or 1-4F1 in binding to one or both of these KIRs).

In another aspect, the antibody binds both KIR2DL1 and KIR2DL2/3 human receptors, reduces or neutralizes or reverses inhibition of NK cell cytotoxicity mediated by these KIRs, and competes with 1-7F9 for binding to the KIR2DL1 human receptor, the KIR2DL2/3 human receptor, or both KIR2DL1 and KIR2DL2/3 human receptors. Optionally, said antibody is a chimeric, human, or humanized antibody.

In another aspect, the antibody binds both KIR2DL1 and KIR2DL2/3 human receptors, reduces, neutralizes or reverses inhibition of NK cell cytotoxicity mediated by these KIRs, and competes with EB6 for binding to the KIR2DL1 human receptor, or competes with GL183 and/or DF200 for binding to the KIR2DL2/3 human receptor; or it competes with both EB6 for binding to the KIR2DL1 human receptor and GL183 and/or DF200 for binding to the KIR2DL2/3 human receptor. In one embodiment, the antibody is not NKVSF1 (Pan2D), not A210, not A803g, and/or not DF200. The antibody can be, e.g., a murine, chimeric, human, or humanized antibody.

In another aspect, the antibody comprises VH, VL, or both VH and VL regions that are at least substantially identical to the VH and/or VL regions of 1-7F9 or 1-4F1. The antibody can be of any subclass, including IgG1, IgG2, IgG3, and IgG4. In a particular aspect, the antibody is a human IgG4 antibody. In another particular aspect, the antibody is a human IgG2 antibody. The antibody can be a chimeric, human, or humanized antibody.

In another aspect, the antibody is human, competes with 1-7F9 or 1-4F1, and recognizes, binds to, or has immunospecificity for at least partially the same, or the same, epitope or "epitopic site" on a KIR molecule as the monoclonal antibody 1-7F9 or 1-4F1. Preferably, said KIR molecule is a human KIR2DL1 or KIR2DL2/3 receptor.

In another aspect, the antibody binds a common determinant present in both KIR2DL1 and KIR2DL2/3 human receptors and reduces, neutralizes or reverses inhibition of NK cell cytotoxicity mediated by these KIRs. The antibody more specifically can bind at least partially the same, substantially the same, or the same epitope on KIR as monoclonal antibody 1-7F9.

In a particular aspect, the antibody is a monoclonal antibody that exhibits one or more of the above-described characteristics.

In another aspect, functional fragments and derivatives of the antibodies described herein can be prepared which have substantially similar antigen binding, specificity and/or activity, including, without limitation, Fab fragments, Fab'2 fragments, immunoadhesins, diabodies, camelized antibodies, Janusins, minibodies, CDRs, and ScFv fragments.

Unless otherwise specified, antibodies or bivalent fragments or derivatives thereof are monospecific, i.e., both "arms" of the antibodies, fragments, or derivatives bind the same antigen(s).

In yet another aspect, antibody derivatives comprising an antibody of the invention conjugated or covalently bound to a toxin, a radionuclide, a detectable moiety (e.g., a fluor), or a solid support, can be prepared.

The invention also encompasses pharmaceutical compositions comprising an antibody as disclosed above, a fragment thereof, or a derivative of either thereof. Accordingly, the invention also relates to use of an antibody as disclosed herein in a method for the manufacture of a medicament. In preferred embodiments, the medicament or pharmaceutical composition is for the treatment of a cancer or other proliferative disorder, an infection, or for use in transplantation.

In one aspect, the invention relates to a composition (e.g., a composition formulated for pharmaceutical administration, a kit for preparing such a composition, an assay kit or media, purification media, etc.) that comprises an antibody that binds at least two different human inhibitory KIR receptor gene products and is capable of neutralizing KIR-mediated inhibition cytotoxicity by NK cells expressing at least one of said two different human inhibitory KIR receptors, wherein the antibody is incorporated into a liposome. The liposome may also comprise an additional substance such as, e.g., a nucleic acid molecule for the delivery of genes for gene therapy; a nucleic acid molecule for the delivery of antisense RNA, RNAi, or siRNA for suppressing a gene in an NK cell; or a toxin or a drug for the targeted killing of NK cells.

Described herein are also methods of regulating human NK cell activity in vitro, ex vivo, or in vivo, comprising contacting human NK cells with an effective amount of an antibody of the invention, a fragment of such an antibody, a derivative of either thereof, or a pharmaceutical composition comprising at least one of any thereof. Preferred methods comprise administration of an effective amount of a pharmaceutical compositions of this invention and are directed at increasing the cytotoxic activity of human NK cells, most preferably ex vivo or in vivo, in a subject having a cancer, an infectious disease, or an immune disease. For example, administration can be effected by intravenous infusion of the antibody in a suitable buffer to a patient with cancer or an infectious disease (such as a viral disease).

The invention also provides a composition comprising an antibody that binds at least two different human inhibitory KIR receptor gene products, wherein the antibody is capable of neutralizing KIR-mediated inhibition of NK cell cytotoxicity in NK cells expressing at least one of the two different human inhibitory KIR receptors, the antibody being present in an amount effective to detectably potentiate NK cell cytotoxicity in a patient or in a biological sample comprising NK cells; and a pharmaceutically acceptable carrier or excipient. Preferably the antibody binds a common determinant present on KIR2DL1 and KIR2DL2/3. Compositions comprising an antibody of the invention may optionally further comprise a second therapeutic agent (an agent that induces, promotes, and/or enhances a therapeutic effect in a host that is related to a condition or disorder for which the antibody is administered—e.g., a condition related to a cancer, transplantation, an infectious disease, a viral infection, etc.). In one aspect, a second therapeutic agent that can be co-administered with an antibody of the invention in such a combination composition may be selected from, for example, an immunomodulatory agent, a hormonal agent, a chemotherapeutic agent, an anti-angiogenic agent, an apoptotic agent, a second antibody specific for a non-KIR antigen, optionally a second antibody that binds to and inhibits and neutralizes an inhibitory KIR, or reduces the signalling from an inhibitory KIR, an anti-infective agent, a targeting agent, or an adjunct compound. Advantageous immunomodulatory agents may be selected from IL-1alpha, IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, or IFN-gamma. Examples of the chemotherapeutic agents include alkylating agents, antimetabolites, cytotoxic antibiotics, adriamycin, dactinomycin, mitomycin, caminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s), other vinca alkyloids and derivatives or prodrugs thereof. Examples of hormonal agents include leuprorelin, goserelin, triptorelin, buserelin, tamoxifen, toremifene, flutamide, nilutamide, cyproterone bicalutamid anastrozole, exemestane, letrozole, fadrozole medroxy, chlormadinone, megestrol, other LHRH agonists, other anti-estrogens, other anti-androgens, other aromatase inhibitors, and other progestagens. Preferably, the second antibody that binds to and inhibits an inhibitory KIR receptor is an antibody or a derivative or fragment thereof that binds to an epitope of an inhibitory KIR receptor that differs from the epitope bound by the antibody that binds a common determinant present on at least two different human inhibitory KIR receptor gene products. In another aspect, a second antibody may be directed to a target associated with the disease state that is at least partially treatable by administration of the antibody of the invention (e.g., a cancer-associated antigen, a viral infection-associated antigen, etc.).

The invention further provides a method of detectably potentiating NK cell activity in a patient in need thereof, comprising the step of administering to the patient a composition according to the invention. A patient in need of NK cell activity potentiation can be any patient diagnosed as having a disease or disorder wherein such potentiation may promote, enhance, and/or induce a therapeutic effect (or promotes, enhances, and/or induces such an effect in at least a substantial proportion of patients with the disease or disorder and substantially similar characteristics as the patient—as may determined by, e.g., clinical trials). A patient in need of such treatment may be suffering from, e.g., cancer, another proliferative disorder, an infectious disease or an immune disorder. Preferably, the method comprises the additional step of administering to the patient an appropriate additional therapeutic agent selected from an immunomodulatory agent, a hormonal agent, a chemotherapeutic agent, an anti-angiogenic agent, an apoptotic agent, a second antibody specific for an antigen distinct from KIR, optionally a second antibody that binds to and inhibits and neutralizes an inhibitory KIR receptor, or reduces the signalling from an inhibitory KIR, an anti-infective agent, a targeting agent or an adjunct compound wherein said additional therapeutic agent is administered to said patient as a single dosage form together with said antibody, or as separate dosage form. The dosage of the antibody (or antibody fragment/derivative) and the dosage of the additional therapeutic agent collectively are sufficient to detectably induce, promote, and/or enhance a therapeutic response in the patient which comprises the potentiation of NK cell activity. Where administered separately, the antibody, fragment, or derivative and the additional therapeutic agent are desirably administered under conditions (e.g., with respect to timing, number of doses, etc.) that result in a detectable combined therapeutic benefit to the patient.

Further encompassed by the present invention are antibodies which are capable of specifically binding NK cells and/or KIR receptors in a non-human primate, preferably a monkey. Also encompassed are methods for evaluating the toxicity, dosage and/or activity or efficacy of antibodies of the invention which are candidate medicaments. In one aspect, the invention encompasses a method for determining a dose of an antibody that is toxic to an animal or target tissue by administering an antibody of the invention to an non-human primate recipient animal having NK cells, and assessing any toxic or deleterious or adverse effects of the agent on the animal, or preferably on a target tissue. In another aspect, the invention is a method for identifying an antibody that is toxic to an animal or target tissue by administering an antibody of the invention to an non-human primate recipient animal having NK cells, and assessing any toxic or deleterious or adverse effects of the agent on the animal, or preferably on a target tissue. In another aspect, the invention is a method for identifying an antibody that is efficacious as treatment of an infection, disease or tumor by administering an antibody of the invention to a non-human primate model of infection, disease or cancer, and identifying the antibody that ameliorates the infection, disease or cancer, or a symptom thereof. In one embodiment, said antibody of the invention is an antibody which (a) cross reacts with at least two inhibitory human KIR receptors at the surface of human NK cells, and (b) cross-reacts with NK cells or a KIR receptor of the non-human primate.

Further encompassed by the present invention is a method of detecting the presence of NK cells bearing an inhibitory KIR on their cell surface in a biological sample or a living organism, said method comprising the steps of:

a) contacting said biological sample or living organism with an antibody of the invention, wherein said antibody is conjugated or covalently bound to a detectable moiety; and b) detecting the presence of said antibody in said biological sample or living organism.

The invention also provides a method of purifying from a sample NK cells bearing an inhibitory KIR on their cell surface comprising the steps of:

a) contacting said sample with an antibody of the invention under conditions that allow said NK cells bearing an inhibitory KIR on their cell surface to bind to said antibody, wherein said antibody is conjugated or covalently bound to a solid support (e.g., a bead, a matrix, etc.); and b) eluting said bound NK cells from said antibody conjugated or covalently bound to a solid support.

Figure 10:
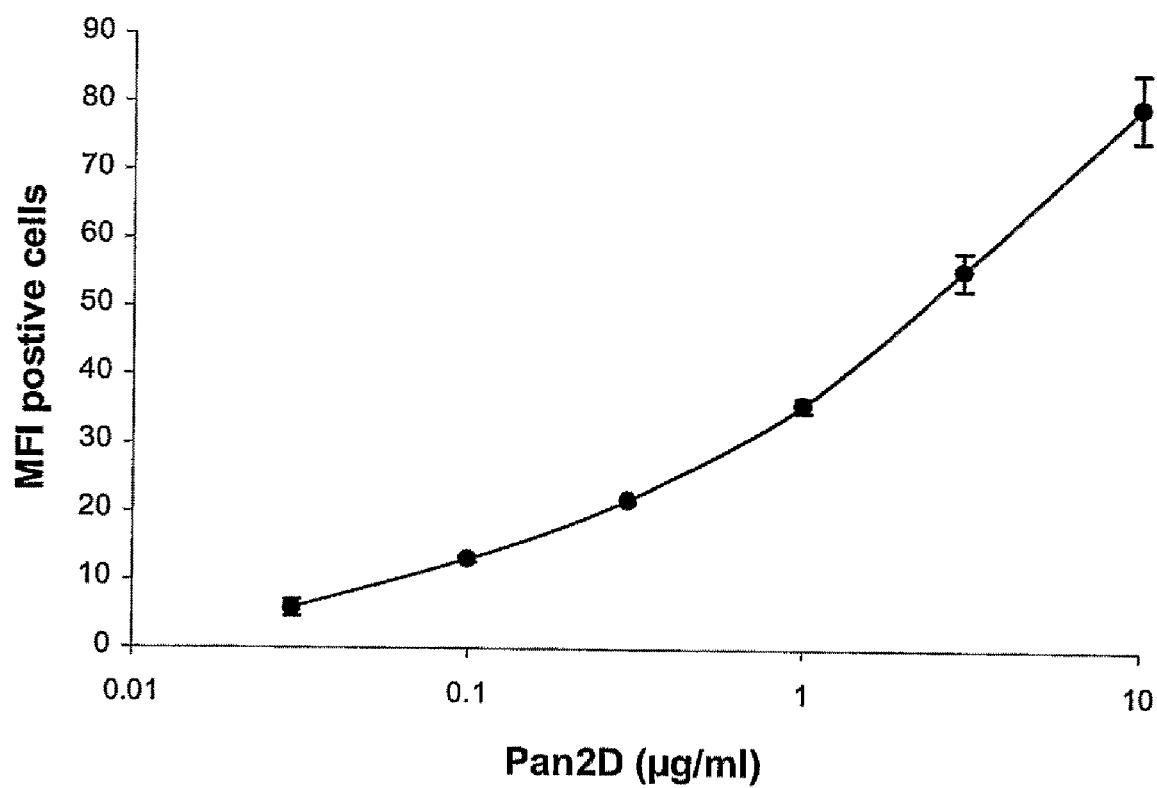
FIG. 10 depicts Pan2D (NKVSF1) mAb titration demonstrating binding of the mAb to cynomolgus NK cells. Cynomolgus NK cells (NK bulk day 16) were incubated with different amount of NKVSF1 (Pan2D) mAb followed by PE-conjugated goat F(ab')2 fragments anti-mouse IgG (H+L) antibodies. The percentage of positive cells was determined with an isotypic control (purified mouse IgG1). Samples were done in duplicate. Mean fluorescence intensity=MFI.

It has been found that antibody NKVSF1 (Pan2D) also binds to NK cells from cynomolgus monkeys, see FIG. 10.

The invention therefore provides an antibody, as well as fragments and derivatives thereof, wherein said antibody, fragment or derivative cross-reacts with at least two inhibitory human KIR receptors at the surface of human NK cells, and which furthermore binds to NK cells from cynomolgus monkeys. In one embodiment hereof, the antibody is not antibody NKVSF1, not A210, and/or not A802g. The invention also provides a method of testing the toxicity of an antibody, as well as fragments and derivatives thereof, wherein said antibody, fragment or derivative cross-reacts with at least two inhibitory human KIR receptors at the surface of human NK cells, wherein the method comprises testing the antibody in a cynomolgus monkey.

In a further aspect, the invention provides an antibody, antibody fragment, or derivative of either thereof, that comprises the light variable region or one or more light variable region CDRs of antibody 1-7F9 or 1-4F1. In still another aspect, the invention provides an antibody, antibody fragment, or derivative of either thereof that comprises a sequence that is highly similar to all or essentially all of the light chain variable region sequence of 1-7F9 or 1-4F1.

In a further aspect, the invention provides an antibody, antibody fragment, or derivative of either thereof, which comprises the heavy chain variable region or one or more heavy chain variable region CDRs of antibody 1-7F9 or 1-4F1. In still another aspect, the invention provides an antibody, antibody fragment, or derivative of either thereof that comprises a sequence that is highly similar to all or essentially all of the heavy chain variable region sequence of 1-7F9 or 1-4F1.

Antibodies

The present invention provides novel antibodies and fragments or derivatives thereof that bind common determinants conserved among human inhibitory KIR receptors, preferably including a determinant present on at least two different KIR2DL gene products, but not on KIR2DS4, and which cause potentiation of NK cells expressing at least one of those KIR receptors. The invention discloses, for the first time, that such cross-reacting and neutralizing antibodies can be produced, and effectively used in modulation of NK cell activity, which represents an unexpected result and opens an avenue towards novel and effective NK-based therapies, particularly in human subjects.

Within the context of this invention, a "common determinant" designates a determinant or epitope that is shared by several gene products of the human inhibitory KIR receptors. Preferably, the common determinant is shared by at least two members of the KIR2DL receptor group. More preferably, the determinant is shared by at least KIR2DL1 and KIR2DL2/3. Certain antibodies of this invention may, in addition to recognizing multiple gene products of the KIR2DL type, also recognize determinants present on other inhibitory KIRs, such as gene product of the KIR3DL receptor group; e.g., KIR3DL1 and/or KIR3DL2. The determinant or epitope may represent a peptide fragment or a conformational epitope shared by said members. In a more specific embodiment, the antibody of this invention specifically binds to substantially the same epitope recognized by monoclonal antibody DF200. This determinant is present on both KIR2DL1 and KIR2DL2/3. In another preferred embodiment, the antibody of this invention specifically binds to substantially the same epitope recognized by human mAb 1-7F9, or the epitope recognized by human mAb 1-4F1, said epitopes being present on KIR2DL1, -2 and -3, but not on KIR2DS4.

The term "antibodies," as used herein, refers to polyclonal and monoclonal antibodies, as well as to fragments and derivatives of said polyclonal and monoclonal antibodies unless otherwise stated or clearly contradicted by context. Depending on the type of constant domain in the heavy chains, full length antibodies typically are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention because they are the most common antibodies in the physiological situation and because they are most easily made in a laboratory setting. Typically, an "antibody" in the context of this invention refers to a monoclonal antibody, more preferably a "human" monoclonal antibody.

One embodiment of the invention provides a method of blocking the interaction of an inhibitory KIR and its corresponding HLA ligand in vivo, for therapeutic purposes that involve activation of endogenous NK cells. In such a setting, it may be advantageous to avoid depleting the NK cells, since, if depleted, the NK cells could not exert their therapeutically beneficial effects. Therefore, antibody isotypes such as IgG4 and IgG2 which exhibit little binding to Fc-receptors, and which do not activate the complement system, are typically preferred. The isotype of 1-7F9 is IgG4. IgG2 antibodies are also generally considered to be non-depleting, and may also be more stable molecules than IgG4 antibodies, thereby conferring a longer half-life in vivo. 1-4F1 is of the IgG2 isotype.

Antibody Production

The antibodies of this invention may be produced by a variety of techniques known in the art. Typically, they are produced by immunization of a non-human animal, preferably a mouse, with an immunogen comprising an inhibitory KIR polypeptide, preferably a KIR2DL polypeptide, more preferably a human KIR2DL polypeptide. The inhibitory KIR polypeptide may comprise the full length sequence of a human inhibitory KIR polypeptide, or a fragment or derivative thereof, typically an immunogenic fragment, i.e., a portion of the polypeptide comprising an epitope exposed on the surface of the cell expressing an inhibitory KIR receptor. Such fragments typically contain at least about 7 consecutive amino acids of the mature polypeptide sequence, even more preferably at least about 10 consecutive amino acids thereof. Fragments typically are essentially derived from the extracellular domain of the receptor. Even more preferred is a human KIR2DL polypeptide which includes at least one, more preferably both, extracellular Ig domains, of the full length KIRDL polypeptide and is capable of mimicking at least one conformational epitope present in a KIR2DL receptor. In other embodiments, said polypeptide comprises at least about 8 consecutive amino acids of an extracellular Ig domain of amino acid positions 1-224 of the KIR2DL1 polypeptide (amino acid numbering of according to Wagtmann et al., Immunity 1995; 2:439-449, which is incorporated by reference herein in its entirety, or according to the PROW internet website found at the World Wide Web (www) address ncbi.nlm.nih.gov/prow/guide/1326018082.htm).

In one embodiment, the immunogen comprises a wild-type human KIR2DL polypeptide in a lipid membrane, typically at the surface of a cell. In a specific embodiment, the immunogen comprises intact NK cells, particularly intact human NK cells. In another embodiment, the cells are lysed or otherwise treated so as to not be intact. The immunogen can be, for example, suspended or dissolved in a buffer, optionally with an adjuvant, such as complete Freund's adjuvant, prior to administration to a non-human mammal, such as a mouse, rabbit, goat, horse, dog, sheep, guinea pig, rat, hamster, etc.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988)). The immunogen is then suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, principles relevant to selection of the location and frequency of immunization sufficient to stimulate the production of antibodies are also well known in the art. In an exemplary immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with inhibitory KIR receptors.

In an alternate embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors (available from the Salk Institute Cell Distribution Center, San Diego, Calif. U.S.A.), or the X63 Ag8653 and SP-2 cell lines (available from the American Type Culture Collection, Rockville, Md. U.S.A.). The cell fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days. The hybridoma colonies are then assayed for the production of antibodies that cross-react with multiple inhibitory KIR receptor gene products. The assay is typically a calorimetric ELISA-type assay, although several other types of assays may be employed, including immunoprecipitation and radioimmunoassay, or FACS, Biacore, Scintillation-proximity assays (SPA), or other types of assays well known in the art. The wells containing antibodies of the desired specificity are examined to determine if one or more distinct hybridoma cell colonies are present. If more than one colony is present, the cells may be re-cloned and grown to ensure that only a single cell has given rise to the colony producing the desired antibody. Positive wells with a single apparent colony are typically re-cloned and re-assayed to insure that only one monoclonal antibody is being detected and produced.

In a preferred embodiment, the non-human animal used to produce antibodies according to applicable methods of the invention is a mammal, such as a rodent (e.g., mouse, rat, etc.), bovine, porcine, horse, rabbit, goat, sheep, etc. Also, the non-human mammal may be genetically modified or engineered to produce "human" antibodies, such as the Xenomouse™ (Abgenix) or HuMAb-Mouse™ (Medarex), as described below.

Antibodies also may be produced transgenically through the generation of a chordate (such as a mammal or bird) or a plant that is transgenic for the immunoglobulin heavy and light chain sequences of interest and production of the antibody in a recoverable form therefrom (see, e.g., Ma et al., Nature Rev. Genetics 4:794-805 (2003); Nolke et al., Expert Opin Biol Ther. 2003 October; 3(7):1153-62; Schillberg et al., Cell Mol Life Sci. 2003 March; 60(3):433-45; Tekoah et al., Arch Biochem Biophys. 2004 Jun. 15; 426(2):266-78; Fischer et al., Eur. J. of Biochem., 262(3):810 (1999); and US Patent Application 20030084482 regarding production of antibodies and antibody-like proteins in plants). In connection with the transgenic production in mammals, antibodies and other proteins can be produced in, and recovered from, the milk of goats, cows, or other mammals. See, e.g., U.S. Pat. Nos. 5,827,690, 5,756,687, 5,750,172, and 5,741,957. Antibodies also may be produced in the eggs of birds and recovered therefrom. See, e.g., Tini et al., Comp Biochem Physiol A Mol Integr Physiol. 2002 March; 131(3):569-74 and U.S. Pat. No. 4,550,019.

Antibodies may also be produced by selection of combinatorial libraries of immunoglobulins, as disclosed for instance in Ward et al., Nature, 341 (1989) p. 544.

According to another embodiment, the invention provides a hybridoma derived from a B cell from a non-human host, wherein said B-cell produces an antibody that binds a determinant present on at least two different human inhibitory KIR receptor gene products and said antibody is capable of neutralizing the inhibitory activity of said receptors. More preferably, the hybridoma of this aspect of the invention is not a hybridoma that produces the monoclonal antibody NKVSF1, not A210, and/or not A802g. The hybridoma according to this aspect of the invention can be created as described above by the fusion of splenocytes from the immunized non-human mammal with an immortal cell line. Hybridomas produced by this fusion can be screened for the presence of such a cross-reacting antibody as described elsewhere herein. Preferably, the hybridoma produces an antibody that recognizes a determinant present on at least two different KIR2DL gene products, and cause potentiation of NK cells expressing at least one of those KIR receptors. Even more preferably, the hybridoma produces an antibody that binds to substantially the same epitope or determinant as 1-7F9 and which potentiates NK cell activity, or which binds substantially the same epitope as 1-4F1. Most preferably, the hybridoma is hybridoma 1-7F9 which produces monoclonal antibody 1-7F9, or hybridoma 1-4F1 which produces monoclonal antibody 1-4F1.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) can be separated away from the cells, and the monoclonal antibody is purified. Purification is typically achieved by chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference), or by other known techniques such as electrophoresis or dialysis. The bound antibody is typically eluted from protein A/protein G columns by using low pH buffers (glycine or acetate buffers of pH 3.0 or less) with immediate neutralization of antibody-containing fractions. These fractions can be pooled, dialyzed, and concentrated as needed.

Human Antibodies

In one aspect, the invention provides human anti-KIR antibodies. "Human" antibodies are distinguishable from "humanized" antibodies (which are described separately below). Such "human" antibodies may include amino acid residues not encoded by human germ line immunoglobulin sequences (e.g., mutations introduced by random or site-specific mutagenesis in vitro or by somatic mutation in vivo), for example in the CDRs, such as in CDR3. However, the term "human antibody", as used herein, is intended to not include humanized antibodies or human/mouse chimera antibodies in which CDR sequences derived from the germ line of another mammalian species, such as a mouse, have been grafted onto human framework sequences.

Transgenic animals can and have been developed that harbour human Ig-genes and, upon immunization, produce a full repertoire of human antibodies in the absence of mouse immunoglobulin production. Such human Ig-transgenic mice can be employed to produce human antibodies. Such human antibodies can be generated in human Ig-transgenic animals (e.g., mice, rats, sheep, pigs, goats, cattle, horses, etc.) comprising human immunoglobulin loci and native immunoglobulin gene deletions, such as in a XenoMouse™ (Abgenix—Fremont, Calif., USA) (see, e.g., Green et al. Nature Genetics 7:13-21 (1994); Mendez et al. Nature Genetics 15:146-156 (1997); Green and Jakobovits J. Exp. Med. 188:483-495 (1998); European Patent No., EP 0 463 151 B1; International Patent Application Nos. WO 94/02602, WO 96/34096; WO 98/24893, WO 99/45031, WO 99/53049, and WO 00/037504; and U.S. Pat. Nos. 5,916,771, 5,939,598, 5,985,615, 5,998,209, 5,994,619, 6,075,181, 6,091,001, 6,114,598 and 6,130,364) or transgenic animals comprising a minilocus of human Ig-encoding genes such as the HuMab-Mouse™ (Medarex—Princeton, N.J., USA) (see, e.g., EP 0546073, EP0546073; U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, 5,643,763; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884). Splenocytes from such transgenic mice can be used to produce hybridomas that secrete human monoclonal antibodies according to well known techniques, as described herein. Similar techniques and principles are described in, e.g., Jakobovits et al., Proc. Natl. Acad. Sci. USA, 90:2551-255 (1993); Jakobovits et al., Nature, 362:255-258 (1993); and Bruggemann et al., Year in Immuno., 7:33 (1993)).

Further, human antibodies or antibodies from other species can be generated through display-type technologies, including, without limitation, phage display, retroviral display, ribosomal display, and other related techniques, using methods well known in the art, and the resulting molecules can be subjected to additional maturation methods, such as affinity maturation, as such techniques also are well known (see, e.g., (Hoogenboom et al., J. Mol. Biol. 227: 381 (1991) (phage display); Vaughan, et al., Nature Biotech 14:309 (1996) (phage display); Hanes and Plucthau PNAS USA 94:4937-4942 (1997) (ribosomal display), Parmley and Smith Gene 73:305-318 (1988) (phage display), Marks et al., J. Mol. Biol., 222: 581 (1991), Scott TIBS 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743). If display technologies are utilized to produce antibodies that are not human, such antibodies can be humanized, e.g., as described elsewhere herein.

Accordingly, as described herein, anti-KIR mAbs are promising agents for the treatment of cancer and viral infections and other diseases and disorders. Anti-KIR mAbs may be generated by various approaches, such as humanization of murine mAbs or by fusion of splenocytes from human Ig-transgenic mice (XenoMouse, or HuMab mice), by phage-display, or by immortalization of human Ab-producing B cells, or by other methods. In either case, the antibody can be produced by cell lines and purified in quantities suitable for formulation, packaging and injection into patients in need thereof.

Recombinant Production

Anti-KIR antibodies can also be prepared by recombinant expression in single cell organisms, such as yeast; or in bacterial cell cultures (such as in $E.\ coli$); or in eukaryotic cell culture (e.g., in a culture of a mammalian cells) using standard techniques.

Thus, according to an alternate embodiment, the DNA encoding heavy and light chains of a cross-reactive and neutralizing anti-KIR antibody, that binds a determinant present on at least two different human inhibitory KIRs, is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, or chimeric antibodies comprising the antigen recognition portion of the antibody. Preferably, the DNA used in this embodiment encodes an antibody that recognizes a determinant present on at least two different KIR2DL gene products, but not on KIR2DS3 or -4, and that cause potentiation of NK cells expressing at least one of those KIR2DL receptors. Even more preferably, the DNA encodes an antibody that binds to substantially the same epitope or determinant as 1-7F9 and which potentiates NK cell activity. Most preferably, that DNA encodes monoclonal antibody 1-7F9.

DNA encoding the monoclonal antibodies of the invention is readily isolated and sequenced using conventional procedures (e.g., by using oligonucleotide probes that are capable of binding specifically to genes encoding the heavy and light chains of murine or human antibodies). Once isolated, the DNA can be placed into expression vectors, which are then transfected into host cells such as $E.\ coli$ cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding fragments of the antibody is well known in the art (see, for example, Skerra et al., Curr. Opinion in Immunol., 5, pp. 256 (1993); and Pluckthun, Immunol. Revs. 130, pp. 151 (1992).

Additionally, recombinant production of antibodies from known variable heavy (VH) and variable light (VL) chains, and human constant regions has been described by, for example, Ruker et al. (Annals of the New York Academy of Sciences. 1991; 646:212-219), who reports the expression of a human monoclonal anti-HIV-1 antibody in CHO cells; Bianchi et al. (Biotechnology and Bioengineering. 2003; 84:439-444), who describes high-level expression of full-Length antibodies using trans-complementing expression vectors, No Soo Kim et al. (Biotechnol. Prog. 2001; 17:69-75), who describes key determinants in the occurrence of clonal variation in humanized antibody expression of CHO cells during dihydrofolate reductase mediated gene amplification; King et al. (Biochemical Journal. 1992; 281:317-323), who reports expression, purification and characterization of a mouse-human chimeric antibody and chimeric Fab' fragment; WO 2003064606 which describes isolated human monoclonal antibodies comprising a human heavy and a human light chain variable regions, both comprising FR1, CDR1, FR2, CDR2, FR3, CDR3 and FR4 sequences; and WO 2003040170 which describes chimeric or human monoclonal antibodies and antigen-binding portions that specifically binds to and activates human CD40.

The entire cDNA sequences encoding the constant regions of human IgG can be found in the following GenBank entries, each of which incorporated by reference in its entirety, accessed on Jan. 6, 2005:

Human IgG1 constant heavy chain region: GenBank accession #: J00228

Human IgG2 constant heavy chain region: GenBank accession #: J00230

Human IgG3 constant heavy chain region: GenBank accession #: X04646

Human IgG4 constant heavy chain region: GenBank accession #: K01316

Human kappa light chain constant region: GenBank accession #: J00241.

In an exemplary embodiment, to produce recombinant mAb production from 1-7F9 or 1-4F1 VH and VL sequences, the following protocol can be applied. Steps 1-3 describe retrieval of the VH and VL regions from a hybridoma or other cell producing 1-7F9 or 1-4F1. However, the cDNA encoding the 1-7F9 or 1-4F1 VH and VL sequences (or mutants or derivatives thereof), to be used in step 4, can also be prepared from the sequence information provided in FIG. 14 or 15, using well-established techniques for synthesizing cDNA fragments. Alternatively, the VH and VL fragments of 1-7F9 or 1-4F1, or mutants or derivatives thereof, may be cloned into any one of a number of expression vectors described in the scientific literature or commercially available expression vectors, containing a constant region of the desired Ig subclass, in order to express a full-length antibody. Additionally, VH and VL fragments of 1-7F9 or 1-4F1, or mutants or derivatives thereof can be cloned into vectors encoding truncated constant regions in order to express antibody fragments (e.g., Fab fragments). One example of a commercially available vector is pASK84, available from the ATCC (American Type Culture Collection, catalog number 87094).

(1) Isolation of Total RNA from Hybridoma Cells:

$4 \times 10^6$ hybridoma cells (such as 1-7F9 or 1-4F1) secreting antibodies against human KIR are used for isolation of total RNA using RNeasy Mini Kit from Qiagen, according to manufacturers instructions, and briefly outlined here: The cells are pelleted by centrifugation for 5 min at 1000 rpm and disrupted by addition of 350 μl RLT buffer containing 10 μl/ml mercaptoethanol. The lysate is transferred onto a QIAshredder column from Qiagen and centrifuged for 2 min at maximum speed. The flow-through is mixed with an equal volume of 70% ethanol. Up to 700 μl sample is applied per RNeasy spin column (Qiagen) and centrifuged at 14000 rpm, and the flow-through discarded. 700 μl RW1 buffer is applied per column which is centrifuged at 14000 rpm for 15 s to wash the column. The column is washed twice with 500 μl RPE buffer and centrifuged for 14000 rpm for 15 s. To dry the column it is centrifuged for additionally 2 min at 14000 rpm. The column is transferred to a new collection tube and the RNA is eluted with 50 μl of nuclease-free water and centrifuged for 1 min at 14000 rpm. The RNA concentration is measured by absorbance at OD=260 nm. The RNA is stored at −80° C. until needed.

(2) cDNA Synthesis:

1 μg RNA is used for first-strand cDNA synthesis using SMART RACE cDNA Amplification Kit from Clontech. For preparation of 5'-RACE-Ready cDNA, a reaction mixture is prepared containing RNA isolated as described above, the reverse-primer 5'-CDS primer back, and SMART II A oligo, and this mixture is incubated at 72° C. for about 2 min., and subsequently cooled on ice for about 2 min. before adding 1× First-Strand buffer, DTT (20 mM), dNTP (10 mM) and PowerScript Reverse Transcriptase. The reaction mixture is incubated at 42° C. for 1.5 hour and Tricine-EDTA buffer is added and incubated at 72° C. for 7 min. At this point samples can be stored at −20° C.

(3) PCR Amplification and Cloning of Human Variable Light (VL) and Human Variable Heavy (VH) Chains:

A PCR (Polymerase Chain Reaction) reaction mixture containing 1× Advantage HF 2 PCR buffer, dNTP (10 mM) and 1× Advantage HF 2 polymerase mix is established for separate amplification of variable regions of both VL and VH from cDNA made as above.

For amplification of VL the following primers are used:

```
UPM (Universal Primer Mix):
                                          (SEQ ID NO: 26)
5'-CTAATACGACTCACTATAGGGCAAGCAGTGGTATCAACGCAGAGT-
3'

(SEQ ID NO: 27)
5'-CTAATACGACTCACTATAGGG-3'

VK RACE2:
                                          (SEQ ID NO: 28)
5'-GCAGGCACACAACAGAGGCAGTTCCAGATTTC-3'
```

For amplification of VH the following primers are used:

```
UPM (Universal Primer Mix):
                                          (SEQ ID NO: 29)
5'-CTAATACGACTCACTATAGGGCAAGCAGTGGTATCAACGCAGAGT-
3'

(SEQ ID NO: 30)
5'-CTAATACGACTCACTATAGGG-3'

AB90RACE:
                                          (SEQ ID NO: 31)
5'-GTGCCAGGGGGAAGACCGATGGG-3'
```

Three rounds of PCR are conducted. Round 1: PCR is run for 5 cycles at 94° C. for 5 s and 72° C. for 3 min. Round 2: PCR is run for 5 cycles at 94° C. for 5 s, 70° C. for 10 s, and 72° C. for 1 min. Round 3: PCR is run for 28 cycles at 94° C. for 5 s, 68° C. for 10 s, and 72° C. for 1 min.

The PCR products are analyzed by electrophoresis on a 1% agarose gel and the DNA purified from the gel using QIAEX11 agarose gel extraction kit from Qiagen.

The purified PCR products are introduced into PCR4-TOPO vector using TOPO TA Cloning kit from Invitrogen and used for transformation of TOP10 competent cells.

A suitable amount of colonies are analyzed by colony PCR using Taq polymerase, 1× Taq polymerase buffer, dNTP (10 mM) and the following primers and PCR program:

```
M13forward primer:
5'-GTAAAACGACGGCCAG-3'        (SEQ ID NO: 32)

M13reverse primer:
5'-CAGGAAACAGCTATGAC-3'       (SEQ ID NO: 33)
```

PCR Program:

25 cycles are run at 94° C. for 30 s, 55° C. for 30 s, and 72° C. for 1 min.

Plasmid DNA from clones comprising VL and VH inserts, respectively, is extracted and sequenced using primer M13forward and M13reverse listed above. In the case of the human anti-KIR mAb 1-7F9, the sequences encoding the heavy and light chain variable regions are shown in FIG. 15.

(4) Subcloning of Antibody Genes into Mammalian Expression Vectors

Based on the sequence data for cDNAs encoding the heavy and light chain variable regions of the mAb, primers are designed for the amplification of the variable light (VL) and variable heavy (VH) chain genes, respectively. The variable regions are formatted by PCR to include a Kozak sequence, leader sequence and unique restriction enzyme sites. For the VL, this is achieved by designing 5' PCR primers to introduce a HindIII site, the Kozak sequence and to be homologous to the 5' end of the leader sequence of the variable light chain region. The 3' primer is homologous to the 3' end of the variable region and introduced a BsiWI site at the 3' boundary of the variable region. The VH region is generated in a similar fashion except that a NotI and a NheI site are introduced in the 5' and 3' end instead of HindIII and BsiWI, respectively.

The amplified gene products are each cloned into a eukaryotic expression vector containing the light and heavy chain constant regions, using standard techniques. The VL DNA fragments is digested with HindIII and BsiWI and ligated into a eukaryotic expression vector containing the beta-lactamase gene encoding resistance to ampicillin and an *E. coli* replication origin (pUC); the resulting plasmid is designated VLCL. The VH DNA fragments, is digested with NotI and NheI and introduced into the VLCL vector resulting from the introduction of VL fragment as described above. The resulting plasmid contains functional expression cassettes encoding both the heavy and light chains of the antibody on the same plasmid. The ligated plasmid is used to transform *E. coli*. Plasmid DNA is prepared from these ampicillin resistant bacterial populations and used for transfection into Chinese hamster Ovary cells, or other mammalian cell lines. Transfection and cell culture is done be standard methods, as described for example in "Molecular Cloning", Sambrook et al. The result is transfected cell lines that stably express and secrete the antibody molecule of interest, such as the 1-7F9 or 1-4F1 human anti-KIR mAb or a mAb comprising the VH and VL regions of 1-7F9 or 1-4F1, or another human anti-KIR mAb.

Variants of the antibody can easily be generated. For example, an antibody with the exact same specificity as 1-7F9 or 1-4F1 but of a different isotype than IgG4 or IgG2, respectively, can be obtained by sub-cloning the cDNA encoding VL and VH of 1-7F9 or 1-4F1 into plasmids containing cDNA encoding the kappa light chain constant regions and a heavy constant chain region selected from IgG1 or IgG2 or IgG3 or IgG4 constant heavy chain regions. Thus, an antibody as generated can possess any isotype and the antibody can then be isotype switched using conventional techniques in the art. Such techniques include the use of direct recombinant techniques (see, e.g., U.S. Pat. No. 4,816,397), cell-cell fusion techniques (see e.g., U.S. Pat. No. 5,916,771), and other suitable techniques known in the art. Accordingly, the effector function of antibodies provided by the invention may be "changed" with respect to the isotype of a parent antibody by isotype switching to, e.g., an IgG1, IgG2, IgG3, IgG4, IgD, IgA, IgE, or IgM antibody for various uses, including therapeutic ones.

Thus, in further aspects, the invention provides a hybridoma comprising: (a) a B cell from a mammalian host (typically a non-human mammalian host) that has been immunized with an antigen that comprises an epitope present on an inhibitory KIR polypeptide, fused to (b) an immortalized cell (e.g., a myeloma cell), wherein said hybridoma produces a monoclonal antibody that binds at least two different human inhibitory KIR receptors and is capable of at least substantially neutralizing KIR-mediated inhibition of NK cell cytotoxicity in a population of NK cells expressing said at least two different human inhibitory KIR receptors. In one embodiment, the mammalian host is a transgenic animal capable of producing human antibodies. Optionally, said hybridoma does not produce monoclonal antibody NKVSF1, not A210, and/or not A802g. In various embodiments, the antibody binds KIR2DL1 and KIR2DL2/3 receptors or a common determinant present on both KIR2DL1 and KIR2DL2/3. The hybridoma may produce an antibody that inhibits the binding of a HLA-C allele molecule having a Lys residue at position 80 to a human KIR2DL1 receptor, and the binding of a HLA-C allele molecule having an Asn residue at position 80 to human KIR2DL2/3 receptors. For example, the hybridoma may produce an antibody that binds to substantially the same epitope as monoclonal antibody 1-7F9 or 1-4F1 on either KIR2DL1 or KIR2DL2/3 or both KIR2DL1 and KIR2DL2/3.

The invention also provides methods of producing an antibody which cross-reacts with multiple KIR2DL gene products and which reduces or neutralizes the inhibitory activity of such KIRs, said method comprising the steps of:

(a) immunizing a non-human mammal with an immunogen comprising a KIR2DL polypeptide;

(b) preparing antibodies from said immunized mammal, wherein said antibodies bind said KIR2DL polypeptide, (c) selecting antibodies of (b) that cross-react with at least two different KIR2DL gene products, and (d) selecting antibodies of (c) that potentiate NK cells. In one embodiment, said non-human mammal is a transgenic animal engineered to express a human antibody repertoire (e.g., a non-human mammal comprising human immunoglobulin loci and native immunoglobulin gene deletions, such as a Xenomouse™ (Abgenix—Fremont, Calif., USA) or non-human mammal comprising a minilocus of human Ig-encoding genes, such as the HuMab-Mouse™ (Medarex—Princeton, N.J., USA)). Optionally, step a and b may be replaced by alternative methods for obtaining anti-KIR mAbs, including, without limitation, the use of phage-display or viral transduction of human B cells, or other methods known in the art. Optionally, the method further comprises selecting an antibody that binds to KIR in a primate, preferably a cynomolgus monkey, NK cell or KIR polypeptide. Optionally, the invention further comprises a method of evaluating an anti-KIR antibody, wherein an antibody produced according to the above method is administered to a primate, preferably a cynomolgus monkey, preferably wherein the monkey is observed for the presence or absence of an indication of toxicity of the antibody.

The invention also provides a method of producing an antibody that binds at least two different human inhibitory KIR receptor gene products, wherein the antibody is capable of neutralizing KIR-mediated inhibition of cytotoxicity (or potentiating NK cytotoxicity) by a population of NK cells expressing the at least two different human inhibitory KIR receptor gene products, the method comprising the steps of:

a) immunizing a non-human mammal with an immunogen comprising an inhibitory KIR polypeptide;

b) preparing antibodies from the immunized animal, wherein the antibodies bind the KIR polypeptide, c) selecting antibodies of (b) that cross-react with at least two different human inhibitory KIR receptor gene products, and selecting antibodies of (c) that capable of neutralizing KIR-mediated inhibition of NK cell cytotoxicity on a population of NK cells expressing the at least two different human inhibitory KIR receptor gene products, wherein the order of steps (c) and (d) is optionally reversed and any number of the steps are optionally repeated 1 or more times. The inhibitory KIR polypeptide used for immunization can, in one embodiment, be one or more KIR2DL polypeptide(s) and the antibodies selected in step (c) cross-react with at least KIR2DL1 and KIR2DL2/3. Preferably the antibody recognizes a common determinant present on at least two different KIR receptor gene products; most preferably the KIRs are KIR2DL1 and KIR2DL2/3. In one embodiment, step (c) comprises selecting antibodies which react with at least one KIR2DL and one KIR3DL receptor gene products. For example, the selected antibody could react with KIR2DL1 and KIR2DL2/3 as well as KIR3DL1 and/or KIR3DL2. Optionally, the method further comprises selecting an antibody that binds a primate, preferably a cynomolgus monkey, NK cell or KIR polypeptide. Optionally, the invention further comprises a method of evaluating an antibody, wherein an antibody produced according to the above method is administered to a primate, preferably a cynomolgus monkey, preferably wherein the monkey is observed for the presence or absence of an indication of toxicity of the antibody.

Optionally, in the above-described methods, the antibody selected in step c) or d) is not NKVSF1, not A210, and/or not A802g. Preferably, the antibody prepared in step (b) in the above methods is a monoclonal antibody. Preferably the antibody selected in step (c) in the above methods inhibits the binding of one or more HLA-C allotypes having a Lys residue at position 80 to a human KIR2DL1 receptor, and the binding of one or more HLA-C allotypes having an Asn residue at position 80 to human KIR2DL2/3 receptors. Preferably, the antibodies selected in step (d) in the above methods cause a potentiation in NK cytotoxicity, or a neutralization of KIR-mediated inhibition of NK cytotoxicity. Preferably, the antibody binds to substantially the same epitope as monoclonal antibody 1-7F9 on KIR2DL1 and/or KIR2DL2/3. Optionally the methods also or alternatively comprise the additional step of making fragments of the selected monoclonal antibodies, making derivatives of the selected monoclonal antibodies (e.g., by conjugation with a radionuclide, cytotoxic agent, reporter molecule, or the like), or making derivatives of antibody fragments produced from, or that comprise sequences that correspond to, the sequences of such monoclonal antibodies. In another aspect, a variant of such an antibody can be produced by preparing an antibody that comprises a variant amino acid sequence from the antibody obtained by the above-described methods by use of known genetic engineering methods (e.g., a sequence that is modified so as to change the binding properties of the antibody, increase or decrease the stability of the antibody, enhance purification of the antibody, enhance detection of the antibody, and/or change the immunological properties of the antibody with respect to a host to which it is to be administered).

The invention further provides a method of producing an antibody that binds at least two different human inhibitory KIR receptor gene products, wherein the antibody is capable of neutralizing KIR-mediated inhibition of NK cell cytotoxicity on (or potentiating NK cytotoxicity by) a population of NK cells expressing at least one of the different human inhibitory KIR receptor gene products, the method comprising the steps of:

(a) selecting, from a library or repertoire, a monoclonal antibody or an antibody fragment that cross-reacts with at least two different human inhibitory KIR2DL receptor gene products, and (b) selecting an antibody of (a) that is capable of neutralizing KIR-mediated inhibition of NK cell cytotoxicity in a population of NK cells expressing the at least two different human inhibitory KIR2DL receptor gene products. Preferably the antibody binds a common determinant present on KIR2DL1 and KIR2DL2/3. Optionally, the antibody selected in step (b) is not NKVSF1. Preferably, the antibody selected in step (b) inhibits the binding of a HLA-c allele molecule having a Lys residue at position 80 to a human KIR2DL1 receptor, and the binding of a HLA-C allele molecule having an Asn residue at position 80 to human KIR2DL2/3 receptors. Preferably, the antibody selected in step (b) causes a potentiation in NK cytotoxicity. Preferably, the antibody binds to substantially the same epitope as monoclonal antibody 1-7F9 on KIR2DL1 and/or KIR2DL2/3. Alternatively, the antibody binds substantially the same epitope as monoclonal antibody 1-4F1. Optionally the method comprises the additional step of making fragments of the selected monoclonal antibodies, making derivatives of the selected monoclonal antibodies, or making derivatives of selected monoclonal antibody fragments.

Additionally, the invention provides a method of producing an antibody that binds at least two different human inhibitory KIR receptor gene products, wherein the antibody is capable of neutralizing KIR-mediated inhibition of NK cell cytotoxicity in a population of NK cells expressing at least one of the two different human inhibitory KIR receptor gene products, the method comprising the steps of:

a) culturing a hybridoma of the invention under conditions permissive for the production of the monoclonal antibody; and b) separating the monoclonal antibody from the hybridoma cells. Optionally the method comprises the additional step of making fragments of the monoclonal antibody, making derivatives of the monoclonal antibody, or making derivatives of such monoclonal antibody fragments. Preferably the antibody binds a common determinant present on KIR2DL1 and KIR2DL2/3.

Also provided by the present invention is a method of producing an antibody that binds at least two different human inhibitory KIR receptor gene products, wherein the antibody is capable of neutralizing KIR-mediated inhibition of NK cell cytotoxicity in a population of NK cells expressing at least one of the two different human inhibitory KIR receptor gene products, the method comprising the steps of:

a) isolating from a hybridoma of the invention a nucleic acid encoding the monoclonal antibody;

b) optionally modifying the nucleic acid so as to obtain a modified nucleic acid that comprises a sequence that encodes a modified or derivatized antibody comprising an amino acid sequence that corresponds to a functional sequence of the monoclonal antibody or is substantially similar thereto (e.g., is at least about 65%, at least about 75%, at least about 85%, at least about 90%, at least about 95% (such as about 70-99%) identical to such a sequence) selected from a humanized antibody, a chimeric antibody, a single chain antibody, an immunoreactive fragment of an antibody, or a fusion protein comprising such an immunoreactive fragment;

c) inserting the nucleic acid or modified nucleic acid (or related nucleic acid coding for the same amino acid sequence) into an expression vector, wherein the encoded antibody or antibody fragment is capable of being expressed when the expression vector is present in a host cell grown under appropriate conditions;

d) transfecting a host cell with the expression vector, wherein the host cell does not otherwise produce immunoglobulin protein;

e) culturing the transfected host cell under conditions which cause the expression of the antibody or antibody fragment; and f) isolating the antibody or antibody fragment produced by the transfected host cell. Preferably the antibody binds a common determinant present on KIR2DL1 and KIR2DL2/3.
Antibody Screening and Selection Particular antibodies of this invention are able to reduce or neutralize the KIR-mediated inhibition of NK cell cytotoxicity; particularly inhibition mediated by KIR2DL receptors and more particularly at least both KIR2DL1- and KIR2DL2/3-mediated inhibition. These antibodies are thus "neutralizing", "blocking", or "inhibitory" antibodies, in the sense that they reduce, neutralize and/or block, at least partially and detectably, the inhibitory signaling pathway mediated by KIR receptors when these interact with MHC class I molecules. More importantly, this neutralization activity is displayed with respect to several types of inhibitory KIR receptors, preferably several KIR2DL receptor gene products, and more preferably at least both KIR2DL1 and KIR2DL2/3 so that these antibodies may be used in most or all human subjects with high efficacy. Neutralization of KIR-mediated inhibition of NK cell cytotoxicity can be assessed by various assays or tests, such as standard in vitro cellular cytotoxicity assays, as described herein.

Once an antibody that cross-reacts with multiple inhibitor KIR receptors is identified it can be tested for its ability to reduce or neutralize the inhibitory effect of those KIR receptors in intact NK cells. In a specific variant, the neutralizing activity can be illustrated by the capacity of said antibody to reconstitute lysis by KIR2DL-expressing NK cells of targets expressing HLA-C. In another specific embodiment, the neutralizing activity of the antibody is defined by the ability of the antibody to block or reduce the binding of HLA-C molecules to KIR2DL1 and KIR2DL3 (or the closely related KIR2DL2) receptors, further preferably as it is the capacity of the antibody to alter the binding of KIR2DL2/3 to a HLA-C molecule selected from Cw1, Cw3, Cw7, and Cw8 (or of another HLA-C molecule having an Asn residue at position 80), and/or the binding of KIR2DL1 to a HLA-C molecule selected from Cw2, Cw4, Cw5 and Cw6 (or of another HLA-C molecule having a Lys residue at position 80).

In another variant, the neutralizing activity of an antibody of this invention can be assessed in a cell-based cytotoxicity assay, as disclosed in the Examples provided herein.

In another variant, the neutralizing activity of an antibody of this invention can be assessed in a cytokine-release assay, wherein NK cells are incubated with the test antibody and a target cell line expressing one HLA-C allele recognized by a KIR molecule of the NK population, to stimulate NK cell cytokine production (for example IFN-γ and/or GM-CSF production). In an exemplary protocol, IFN-γ production from PBMC is assessed by cell surface and intracytoplasmic staining and analysis by flow cytometry after about 4 days in culture. Briefly, Brefeldin A (Sigma Aldrich) can be added at a final concentration of about 5 μg/ml for the least about 4 hours of culture. The cells can then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-production from polyclonal activated NK cells can be measured in supernatants using ELISA (GM-CSF: DuoSet Elisa, R&D Systems, Minneapolis, Minn.; IFN-γ: OptE1A set, Pharmingen).

Antibodies of this invention may partially (i.e., reduce) or fully neutralize the KIR-mediated inhibition of NK cell cytotoxicity. For example, preferred antibodies of this invention are able to induce or augment the lysis of HLA-matched, or HLA-compatible, or autologous target cell populations, i.e., cell populations that would not be effectively lysed by NK cells in the absence of said antibody. Accordingly, the antibodies of this invention may also be defined as facilitating NK cell activity in vivo, and/or in vitro.

In a specific embodiment, the antibody binds substantially the same epitope as monoclonal antibody DF200 (produced by hybridoma DF200), 1-7F9, or 1-4F1. Such antibodies can be referred to herein as "DF200 like antibodies", "1-7F9-like antibodies", and "1-4F1-like antibodies", respectively. In a further preferred embodiment, the antibody is a monoclonal antibody. More preferred "DF200 like antibodies" of this invention are antibodies other than the monoclonal antibody NKVSF1. Most preferred is monoclonal antibody 1-7F9 or 1-4F1, and antibodies comprising the VH and/or VL regions of 1-7F9 or 1-4F1.

The identification of one or more antibodies that bind(s) to substantially or essentially the same epitope as the monoclonal antibodies described herein can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (DF200, for example) is mixed with the test antibody and then applied to a sample containing either or both KIR2DL1 and/or KIR2DL2/3, each of which is known to be bound by DF200. Protocols based upon ELISAs, radioimmunoassays, Western blotting, and the use of BIACORE analysis (as described, for example, in the Examples section herein) are suitable for use in such simple competition studies.

In certain embodiments, one would pre-mix the control antibody (1-7F9 or 1-4F1, for example) with varying amounts of the test antibody (e.g., in ratios of about 1:1, 1:2, 1:10 or about 1:100) for a period of time prior to applying to the KIR antigen sample. In other embodiments, the control and varying amounts of test antibody can simply be added separately and admixed during exposure to the KIR antigen sample. As long as one can distinguish bound from free antibodies (e.g., by using separation or washing techniques to eliminate unbound antibodies) and control antibody from the test antibody (e.g., by using species specific or isotype specific secondary antibodies or by specifically labelling the control antibody with a detectable label) one will be able to determine if the test antibody reduce the binding of the control antibody to the different KIR2DL antigens, indicating that the test antibody recognizes substantially the same epitope as 1-7F9. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of 1-7F9 or 1-4F1 to both of KIR2DL1 and KIR2DL2/3 antigens by at least about 50%, such as at least about 60%, or more preferably at least about 70% (e.g., about 65-100%), at any ratio of 1-7F9:test antibody or 1-4F1:test antibody between about 1:1 or 1:10 and about 1:100 is considered to be an antibody that binds to substantially the same epitope or determinant as 1-7F9 or 1-4F1, respectively. Preferably, such test antibody will reduce the binding of 1-7F9 to at least one other, preferably each of the KIR2DL antigens preferably at least about 50%, at least about 60%, at least about 80% or at least about 90% (e.g., about 95%) of the binding of 1-7F9 or 1-4F1 observed in the absence of the test antibody. Of course, such methods can be adapted to identify and/or evaluate antibodies that compete with other antibodies and/or KIR antigens.

Competition can also or alternatively be assessed by, for example, a flow cytometry test. In such a test, cells bearing a given KIR can be incubated first with a control antibody (1-7F9 or 1-4F1, for example), and then with the test antibody labeled with a fluorochrome or biotin. The antibody is said to compete with control antibody if the binding obtained upon preincubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIA-CORE chip (or other media suitable for surface plasmon resonance analysis). The binding of a control antibody (e.g., 1-7F9 or 1-4F1) to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody (such as 1-7F9 or 1-4F1) to both of KIR2DL1 and KIR2DL2/3 antigens by at least about 20% or more, at least about 40%, at least about 50%, at least about 70%, or more, can be considered to be an antibody that binds to substantially the same epitope or determinant as the control antibody (e.g., 1-7F9 or 1-4F1). Preferably, such test antibody will reduce the binding of the control antibody (e.g., 1-7F9 or 1-4F1) to each of the KIR2DL antigens by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

While described in the context of 1-7F9 or 1-4F1 for the purposes of exemplification, it will be appreciated that the above-described screening assays can also be used to identify antibodies that compete with one or more of NKVSF1, DF200, EB6, GL183, and other antibodies, antibody fragments, and antibody derivatives according to the invention.

Upon immunization and production of antibodies in a vertebrate or cell, particular selection steps may be performed to isolate antibodies as claimed. In this regard, in a specific embodiment, the invention also relates to methods of producing such antibodies, comprising:

(a) immunizing a non-human mammal with an immunogen comprising an inhibitory KIR polypeptide;

(b) preparing antibodies from said immunized animal, wherein said antibodies bind said KIR polypeptide, (c) selecting antibodies of (b) that cross-react with at least two different inhibitory KIR gene products, and (d) selecting antibodies of (c) that are capable of neutralizing KIR-mediated inhibition of NK cell cytotoxicity on a population of NK cells expressing at least one of said two different human inhibitory KIR receptor gene products.

In certain embodiments, an additional step is performed between steps (c) and (d) above, to select anti-KIR mAbs that do not react with KIR2DS4.

The selection of an antibody that cross-reacts with at least two different inhibitory KIR gene products may be achieved by screening the antibody against two or more different inhibitory KIR antigens. In a more preferred embodiment, the antibodies prepared in step (b) are monoclonal antibodies. Thus, the term "preparing antibodies from said immunized animal," as used herein, includes obtaining B-cells from an immunized animal and using those B cells to produce a hybridoma that expresses antibodies, as well as obtaining antibodies directly from the serum of an immunized animal. In another preferred embodiment, the antibodies selected in step (c) are those that cross-react with at least KIR2DL1 and KIR2DL2/3.

In yet another preferred embodiment, the antibodies selected in step (d) cause at least about 10% more specific lysis mediated by NK cells displaying at least one KIR recognized by the antibody, and preferably at least about 40% more specific lysis, at least about 50% higher specific lysis, or more preferably at least about 70% increased specific lysis (e.g., about 60-100% increased specific lysis), as measured in a standard chromium release assay towards a target cell expressing cognate HLA class I molecule, compared to the specific lysis in the absence of an anti-KIR mAb. Alternatively, the antibodies selected in step (d) when used in a chromium-release assay employing an NK cell clone expressing one or several inhibitory KIRs and a target cells expressing at least one HLA allele that is recognized by one of the KIRs on the NK clone, the level of cytotoxicity obtained with the antibody should be at least about 20%, preferably at least about 30%, or more of the specific cytotoxicity obtained with the same concentration of DF200 or with a blocking anti-MHC class I antibody, at the same effector:target cell ratio.

The order of steps (c) and (d) of the immediately above-described method can be changed. Optionally, the method also or alternatively may further comprise additional steps of making fragments of the monoclonal antibody or derivatives of the monoclonal antibody or such fragments, e.g., as described elsewhere herein.

In another variant, the invention provides a method for obtaining an antibody that comprises:

(a) selecting, from a library or repertoire, a monoclonal antibody, a fragment of a monoclonal antibody, or a derivative of either thereof that cross-reacts with at least two different human inhibitory KIR2DL receptor gene products, and (b) selecting an antibody, fragment, or derivative of (a) that is capable of neutralizing KIR-mediated inhibition of NK cell cytotoxicity on a population of NK cells expressing said at least two different human inhibitory KIR2DL receptor gene products.

The repertoire may be any (recombinant) repertoire of antibodies or fragments thereof, optionally displayed by any suitable structure (e.g., phage, bacteria, synthetic complex, etc.). Selection of inhibitory antibodies may be performed as disclosed above and further illustrated in the examples.

Computer modelling of the extra-cellular domains of KIR2DL1, -2 and -3 (KIR2DL1-3), based on their published crystal-structures (Maenaka et al. Structure with Folding and design 1999; 7:391-398; Fan et al., Nature immunology 2001; 2:452-460; Boyington et al. Nature, 2000; 405:537-543), revealed the involvement of certain regions or KIR2DL1, -2 and -3 in the interaction between these KIR and the anti-KIR2DL cross-reactive murine monoclonal antibodies DF200 and NKVSF1. Thus, in one embodiment, the present invention provides antibodies that exclusively bind to KIR2DL1 within a region defined by the amino acid residues (105, 106, 107, 108, 109, 110, 111, 127, 129, 130, 131, 132, 133, 134, 135, 152, 153, 154, 155, 156, 157, 158, 159, 160, 161, 162, 163, 181, and 192). In another embodiment the invention provides antibodies that bind to KIR2DL1 and KIR 2DL2/3 without interacting with amino acid residues outside the region defined by the residues (105, 106, 107, 108, 109, 110, 111, 127, 129, 130, 131, 132, 133, 134, 135, 152, 153, 154, 155, 156, 157, 158, 159, 160, 161, 162, 163, 181, and 192).

In another embodiment, the invention provides antibodies that bind to KIR2DL1 and which does not bind to a mutant of KIR2DL1 in which R131 (i.e., the Arg residue at position 131 of the KIR2DL1 mutant) is (i.e., is substituted with) an Ala residue.

In another embodiment, the invention provides antibodies that bind to KIR2DL1 and which does not bind to a mutant of KIR2DL1 in which R157 is Ala.

In another embodiment, the invention provides antibodies that bind to KIR2DL1 and which does not bind to a mutant of KIR2DL1 in which R158 is Ala.

In another embodiment, the invention provides antibodies that bind to KIR2DL1 residues 131, 157, and 158.

In another embodiment, the invention provides antibodies that bind to KIR2DS3(R131W), but not to wild type KIR2DS3.

In a particular embodiment, the antibodies exclusively bind to KIR2DL1 within a region defined by the amino acid residues L38, R41, M44, F45, N46, D47, T48, L49, R50, I52, F64, D72, Y80, P87, and Y88 (in which the letters designate amino acids in single-letter code, and the number is the position of that residue in KIR2DL1 (SEQ ID NO:23), using the numbering system described in Wagtmann et al., Immunity 1995; 2:439-449). These residues have been identified as the 1-7F9 KIR2DL1 epitope (see Example 11).

In another embodiment, the antibodies bind to an antigenic epitope in a KIR2DL1 sequence consisting of the fragment L38 to Y88 of SEQ ID NO:23. In yet another embodiment, the antibodies bind to an antigenic epitope in a KIR2DL1 sequence comprising the fragment L38 to Y88 of SEQ ID NO:23.

In another embodiment, the invention provides antibodies that bind to KIR2DL1 and KIR 2DL2/3 without interacting with amino acid residues outside the region defined by the residues L38, R41, M44, F45, N46, D47, T48, L49, R50, I52, F64, D72, Y80, P87, and Y88.

In another embodiment, the antibodies bind to KIR2DL1 within a region comprising at least 10%, 20%, 30%, 40%, 50%, 60%, 70%, 80%, 90% or more of the amino acid residues L38, R41, M44, F45, N46, D47, T48, L49, R50, I52, F64, D72, Y80, P87, and Y88. In a particular embodiment, the KIR2DL1 epitope for the antibodies comprises the amino acid residues M44 and F45 (see Examples 9 and 11).

In another embodiment, the antibodies bind to KIR2DL1 within a region comprising at least 1, 2, 4, 6, 8, 10, or 12 or all of the amino acid residues L38, R41, M44, F45, N46, D47, T48, L49, R50, I52, F64, D72, Y80, P87, and Y88. In a particular embodiment, the region comprises amino acid residues M44 and F45, and optionally at least 1, 2, 4, 6, 8, 10, or all of L38, R41, N46, D47, T48, L49, R50, I52, F64, D72, Y80, P87, and Y88 (see Examples 9 and 11). In another particular embodiment, the region comprises at least amino acid residues M44, F45, and D72, which are in the KIR2DL1 region where the 1-7F9 epitope and the HLA-C binding sites overlap.

In another embodiment, the invention provides antibodies that bind to KIR2DL1, KIR2DL2/3, and KIR2DS4.

In another embodiment, the invention provides antibodies that bind to both KIR2DL1 and KIR2DL2/3, but not to KIR2DS4.

In another embodiment, the invention provides antibodies that bind to both KIR2DL1 and KIR2DL2/3, but not to KIR2DS3 or to KIR2DS4.

Determination of whether an antibody, antibody fragment, or antibody derivative binds within one of the epitope regions defined above can be carried out in ways known to the person skilled in the art. See, for example, Examples 9 and 11. In another example of such mapping/characterization methods, an epitope region for an anti-KIR antibody may be determined by epitope "foot-printing" using chemical modification of the exposed amines/carboxyls in the KIR2DL1 or KIR2DL2/3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44): 149-67; Huang et al, Journal of Molecular Biology, Vol. 281 (1) pp. 61-67 (1998); and Saito and Patterson, Methods. 1996 June; 9(3):516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR antibody can subsequently be identified by comparison of samples subjected to trypsin digestion and samples incubated with antibody and then subjected to digestion by e.g. trypsin (thereby revealing a foot print for the antibody). Other enzymes like chymotrypsin, pepsin, etc., also or alternatively can be used in a similar epitope characterization methods. Moreover, enzymatic digestion can provide a quick method for analyzing whether a potential antigenic determinant sequence is within a region of the KIR2DL1 in the context of a KIR-binding polypeptide. If the polypeptide is not surface exposed, it is most likely not relevant in terms of immunogenicity/antigenicity. See, e.g., Manca, Ann Ist Super Sanita. 1991; 27(1):15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant resuction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

Antibody Fragments and Derivatives

Fragments and derivatives of antibodies of this invention (which are encompassed by the terms "antibody" and "antibodies" as used in this application, unless otherwise stated or clearly contradicted by context), preferably a 1-7F9- or 1-4F1-like antibody, can be produced by techniques that are known in the art. "Immunoreactive fragments" comprise a portion of the intact antibody, generally the antigen binding site or variable region. Examples of antibody fragments include "kappa bodies" (see, e.g., Ill et al., Protein Eng 10: 949-57 (1997)) and "janusins" (described further elsewhere herein). Fab, Fab', Fab'-SH, $F(ab)_2$, F(ab')2, dAb (Ward et al., (1989) Nature 341:544-546); consisting essentially of a VH domain), Fd (consisting essentially of the VH and CH1 domains), and Fv (consisting essentially of the VL and VH domains) fragments; diabodies; kappa bodies; and janusins. For example, antibody fragments include a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. For instance, Fab or F(ab')2 fragments may be produced by protease digestion of the isolated antibodies, according to conventional techniques.

It will be appreciated that immunoreactive fragments can be modified using known methods, for example to slow clearance in vivo and obtain a more desirable pharmacokinetic profile. For example, the fragment may be modified with polyethylene glycol (PEG) or polyoxyethylated polyols. Methods for coupling and site-specifically conjugating PEG to a Fab' fragment are described in, for example, Leong et al, Cytokine 16(3):106-119 (2001) and Delgado et al, Br. J. Cancer 73(2):175-182 (1996), the disclosures of which are incorporated herein by reference.

In a particular aspect, the invention provides antibodies, antibody fragments, and antibody derivatives comprising the light and/or heavy chain variable region sequence of 1-7F9 or 1-4F1 as set forth in FIG. 14. In another aspect, the invention provides antibodies, antibody fragments, and derivatives thereof that comprise one or more of the light and/or heavy chain variable region CDRs of 1-7F9 or 1-4F1 as set forth in FIG. 15 or described above. Functional variants/analogs of such sequences can be generated by making suitable substitutions, additions, and/or deletions in these disclosed amino acid sequences using standard techniques, which may be aided by the comparison of the sequences. From superimposition of crystal structures of the 1-7F9/KIR2DL1 complex and the and the KIR2DL1/MHC class I complex (Fan et al., Nat. Immunol. 2001; 2: 452-460), PDB-code 1IM9, it can be concluded that a scFv derivative of 1-7F9 will be able to block MHC class I binding to KIR2DL1. Also the single L-chain of 1-7F9 or the single VL domain of 1-7F9 alone, when bound to KIR2DL1, would block MHC class I binding.

Functional variants/analogs of such sequences can be generated by making suitable substitutions, additions, and/or deletions in these disclosed amino acid sequences using standard techniques, which may be aided by the comparison of the sequences. In another aspect, positions where a residue is present in a sequence of one of these antibodies, but not another, may be suitable for deletions, substitutions, and/or insertions.

Alternatively, the DNA of a encoding an antibody of this invention, such as a 1-7F9- or 1-4F1-like antibody, may be modified so as to encode for a fragment of this invention. The modified DNA is then inserted into an expression vector and used to transform or transfect an appropriate cell, which then expresses the desired fragment, as described elsewhere herein.

In an alternate embodiment, the DNA of a hybridoma producing a murine antibody of this invention, such as a DF200-like antibody, can be modified prior to insertion into an expression vector, for example, by substituting the coding sequence for human heavy- and light-chain constant domains in place of the homologous non-human sequences (as described by e.g., Morrison et al., Proc. Natl. Acad. Sci.

U.S.A., 81, pp. 6851 (1984)). In another embodiment, the variable regions encoding the antibody of this invention may be joined, by recombinant DNA engineering, to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a DF-200-like antibody is humanized. "Humanized" forms of antibodies according to this invention are specific chimeric immunoglobulins, immunoglobulin chains or fragments thereof (such as Fv, Fab, Fab', F(ab')2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al., Nature, 332, pp. 323 (1988); and Presta, Curr. Op. Struct. Biol., 2, pp. 593 (1992).

Methods for humanizing the antibodies of this invention are well known in the art. Generally, a humanized antibody according to the present invention has one or more amino acid residues introduced into it from the original antibody. These murine or other non-human amino acid residues are often referred to as "import" residues, which are typically taken from an "import" variable domain. Humanization can be essentially performed following the method of Winter and co-workers (Jones et al., Nature, 321, pp. 522 (1986); Riechmann et al., Nature, 332, pp. 323 (1988); Verhoeyen et al., Science, 239, pp. 1534 (1988)). Accordingly, such "humanized" antibodies are chimeric antibodies (Cabilly et al., U.S. Pat. No. 4,816,567), wherein substantially less than an intact human variable domain has been substituted by the corresponding sequence from the original murine antibody. In practice, humanized antibodies according to this invention are typically human antibodies in which some CDR residues and possibly some FR residues are substituted by residues from analogous sites in the original murine antibody.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol., 151, pp. 2296 (1993); Chothia and Lesk, J. Mol. Biol., 196, pp. 901 (1987)). Another method uses a particular framework from the consensus sequence of all human antibodies of a particular subgroup of light or heavy chains. The same framework can be used for several different humanized antibodies (Carter et al., Proc. Natl. Acad. Sci. U.S.A., 89, pp. 4285 (1992); Presta et al., J. Immunol., 51, pp. 1993)).

It is further important that antibodies be humanized with retention of high affinity for multiple inhibitory KIR receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

As described above, a method of making human monoclonal antibodies is to use a XenoMouse® (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

The antibodies of the present invention, preferably a 1-7F9- or 1-4F1-like antibody, may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. U.S.A., 81, pp. 6851 (1984)).

Other derivatives within the scope of this invention include functionalized antibodies, i.e., antibodies that are conjugated or covalently bound to a toxin, such as ricin, diphtheria toxin, abrin and *Pseudomonas exotoxin*, or a therapeutic radionuclide such as, e.g., $^{90}Y$ or $^{131}I$; to a detectable moiety, such as a fluorescent moiety, a diagnostic radioisotope or an imaging agent; or to a solid support, such as agarose beads or the like. Methods for conjugation or covalent bonding of these other agents to antibodies are well known in the art.

Conjugation to a toxin is useful for targeted killing of NK cells displaying one of the cross-reacting KIR receptors on its cell surface. Once the antibody of the invention binds to the cell surface of such cells, it is internalized and the toxin is released inside of the cell, selectively killing that cell. Such use is an alternate embodiment of the present invention.

Conjugation to a detectable moiety is useful when the antibody of this invention is used for diagnostic purposes. Such purposes include, but are not limited to, assaying biological samples for the presence of the NK cells bearing the cross-reacting KIR on their cell surface and detecting the presence of NK cells bearing the cross-reacting KIR in a living organism. Such assay and detection methods are also alternate embodiments of the present invention.

Conjugation of an antibody of this invention to a solid support is useful as a tool for affinity purification of NK cells bearing the cross-reacting KIR on their cell surface from a source, such as a biological fluid. This method of purification is another alternate embodiment of the present invention, as is the resulting purified population of NK cells.

Pharmaceutical Compositions and Applications

The invention also provides pharmaceutical compositions that comprise a human or humanized antibody, or fragments and derivatives thereof, wherein said antibody, fragment or derivative cross-reacts with at least two inhibitory KIR receptors at the surface of NK cells, reduces or neutralizes their inhibitory signals and potentiates the activity of those cells, in any suitable vehicle in an amount effective to detectably potentiate NK cell cytotoxicity in a patient or in a biological sample comprising NK cells. The pharmaceutical compositions comprising a human or humanized anti-KIR mAb, optionally together with another active agent, for use according to the present invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. The compositions may appear in conventional forms, for example, capsules, tablets, aerosols, solutions or suspensions, or as freeze-dried powder.

Accordingly, one object of the present invention is to provide a pharmaceutical formulation comprising a human or humanized antibody, or fragments or derivatives thereof, which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. In one embodiment of the invention the pharmaceutical formulation is an aqueous formulation, i.e., a formulation comprising water. Such formulation is typically a solution or a suspension. In a further embodiment of the invention the pharmaceutical formulation is an aqueous solution. As used herein, the term "aqueous formulation" is a formulation comprising at least 50% w/w water. Likewise, the term "aqueous solution" is a solution comprising at least 50% w/w water, and the term "aqueous suspension" a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g., freeze-dried or spray-dried) ready for use without any prior dissolution.

In a further aspect, the invention relates to a pharmaceutical formulation comprising an aqueous solution of an antibody as described herein, and a buffer, wherein said the antibody is present in a concentration from 1 mg/ml or above, and wherein said formulation has a pH from about 2.0 to about 10.0.

In another embodiment, the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation also comprises a pharmaceutically acceptable preservative. In another embodiment, the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In one embodiment, the preservative is present in a concentration from 0.1 mg/ml to 20 mg/ml. In another embodiment, the preservative is present in a concentration from 0.1 mg/ml to 5 mg/ml. In yet another embodiment, the preservative is present in a concentration from 5 mg/ml to 10 mg/ml. In still another embodiment, the preservative is present in a concentration from 10 mg/ml to 20 mg/ml. Each one of the specific preservatives listed constitutes an alternative embodiment of the invention. While the use of a preservative in pharmaceutical compositions is well-known to the skilled person; for convenience, reference is made to Remington: The Science and Practice of Pharmacy, 19th edition, 1995.

In a further embodiment, the formulation also comprises an isotonic agent. In one embodiment, the isotonic agent is selected from the group consisting of a salt (e.g., sodium chloride), a sugar, a sugar alcohol, an amino sugar, an amino acid (e.g., L-glycine, L-histidine, arginine, lysine, isoleucine, aspartic acid, tryptophan, threonine), an alditol (e.g., glycerol (glycerine), 1,2-propanediol (propyleneglycol), 1,3-propanediol, 1,3-butanediol), and polyethyleneglycol (e.g., PEG400), or mixtures thereof. Any suitable sugar can be used, including, but not limited to mono-, di-, or polysaccharides; and water-soluble glucans, such as, for example, fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In another embodiment, the isotonic agent is present in a concentration from 1 mg/ml to 50 mg/ml. In another embodiment, the isotonic agent is present in a concentration from 1 mg/ml to 7 mg/ml. In another embodiment, the isotonic agent is present in a concentration from 8 mg/ml to 24 mg/ml. In another embodiment, the isotonic agent is present in a concentration from 25 mg/ml to 50 mg/ml. Each one the specific isotonic agents listed above constitutes an alternative embodiment of the invention. While the use of an isotonic agent in pharmaceutical compositions is well-known to the skilled person; for convenience, reference is made to Remington: The Science and Practice of Pharmacy, 19th edition, 1995.

In a further embodiment, the formulation also comprises a chelating agent. In one embodiment, the chelating agent is selected from salts of ethylenediaminetetraacetic acid (EDTA), citric acid, and aspartic acid, and mixtures thereof. In another embodiment, the chelating agent is present in a concentration from 0.1 mg/ml to 5 mg/ml. In another embodiment, the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19th edition, 1995.

In a further embodiment, the formulation also comprises a stabilizer. While the use of a stabilizer in pharmaceutical compositions is well-known to the skilled person; for convenience, reference is made to Remington: The Science and Practice of Pharmacy, 19th edition, 1995.

Compositions of the invention may, for example, be stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may also comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment, the formulation also comprises a stabilizer selected from the group of high molecular weight polymers or low molecular compounds. In one embodiment, the stabilizer is selected from polyethylene glycol (e.g. PEG 3350), polyvinyl alcohol (PVA), polyvinylpyrrolidone, carboxy-/hydroxycellulose or derivates thereof (e.g., HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment, the formulation also comprises a surfactant. In one embodiment, the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, N-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propane-sulfonate, cationic surfactants (quaternary ammonium bases) (e.g. cetyl-trimethylammonium bromide, cetylpyridinium chloride), non-ionic surfactants (e.g. dodecyl β-D-glucopyranoside), poloxamines (e.g., Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

While the use of a surfactant in pharmaceutical compositions is well-known to the skilled person; for convenience, reference is made to Remington: The Science and Practice of Pharmacy, 19th edition, 1995.

In a further embodiment, the formulation also comprises protease inhibitors such as EDTA (ethylenediamine tetraacetic acid) and benzamidineHCl, although other commercially available and suitable protease inhibitors may also be used. The use of a protease inhibitor is particular useful in pharmaceutical compositions comprising zymogens of proteases in order to inhibit autocatalysis.

Other ingredients may also be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients preferably do not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the antibody, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the antibody, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the antibody in the form of a nasal or pulmonal spray. As another option, the pharmaceutical compositions containing the antibody of the invention can also be adapted to transdermal administration, e.g. by needle-free injection or from a patch, optionally an iontophoretic patch, or transmucosal, e.g. buccal, administration.

The antibody can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit. Rev Ther Drug Carr Sys 14(4) (1997) 395-453).

Based on standardised testing methodology, the aerodynamic diameter (da) of a particle is defined as the geometric equivalent diameter of a reference standard spherical particle of unit density (1 g/cm3). In the simplest case, for spherical particles, da is related to a reference diameter (d) as a function of the square root of the density ratio as described by:

$$d_a = \sqrt{\frac{\rho}{\rho_a}} d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the antibody may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person.

Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the antibody is stable for more than 6 weeks of usage and for more than 3 years of storage.

In another embodiment of the invention the pharmaceutical formulation comprising the antibody is stable for more than 4 weeks of usage and for more than 3 years of storage.

In a further embodiment of the invention the pharmaceutical formulation comprising the antibody is stable for more than 4 weeks of usage and for more than two years of storage.

In an even further embodiment of the invention the pharmaceutical formulation comprising the antibody is stable for more than 2 weeks of usage and for more than two years of storage.

Thus, as described above, pharmaceutically acceptable carriers that may be used in these compositions include, but are not limited to, ion exchangers; alumina; aluminium stearate; lecithin; serum proteins such as human serum albumin; buffer substances such as phosphates and glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyethylene glycol; sodium carboxymethylcellulose; polyacrylates; waxes; polyethylene-polyoxypropylene-block polymers; polyethylene glycol; and wool fat.

The compositions of this invention may be employed in a method of potentiating the activity of NK cells in a patient or a biological sample. This method comprises the step of contacting said composition with said patient or biological sample. Such method will be useful for both diagnostic and therapeutic purposes.

For use in conjunction with a biological sample, the antibody composition can be administered by simply mixing with or applying directly to the sample, depending upon the nature of the sample (fluid or solid). The biological sample may be contacted directly with the antibody in any suitable device (plate, pouch, flask, etc.). For use in conjunction with a patient, the composition must be formulated for administration to the patient.

As described above, the compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Several monoclonal antibodies have been shown to be efficient in clinical situations, such as Rituxan (Rituximab), Herceptin (Trastuzumab) or Xolair (Omalizumab), and similar administration regimens (i.e., formulations and/or doses and/or administration protocols) may be used with the antibodies of this invention. Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 10 mg/m2 and 500 mg/m2. However, it will be appreciated that these schedules are exemplary and that an optimal schedule and regimen can be adapted taking into account the affinity and tolerability of the particular antibody in the pharmaceutical composition that must be determined in clinical trials. Quantities and schedule of injection of an antibody in a pharmaceutical composition of this invention that saturate NK cells for 24 hours, 48 hours 72 hours or a week or a month will be determined considering the affinity of the antibody and its pharmacokinetic parameters in humans and non-human mammals.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), other antibodies and fragments of other antibodies.

In an alternate embodiment, an antibody that binds a common determinant present on at least two different human inhibitory KIR receptor gene products, wherein said antibody is capable of neutralizing KIR-mediated inhibition of NK cell cytotoxicity on NK cells expressing at least one of said two different human inhibitory KIR receptors of this invention, may be incorporated into liposomes ("immunoliposomes"), alone or together with another substance for targeted delivery to a tumor, or the site of an infection, in a human or other non-human mammal. Such other substances include nucleic acids for the delivery of genes for gene therapy or for the delivery of antisense RNA, RNAi or siRNA for suppressing a gene in an NK cell, or toxins or drugs for the targeted killing of NK cells.

For example, a number of therapeutic agents are available for the treatment of cancers. The antibody compositions and methods of the present invention may be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the activity of the antibody in a pharmaceutical composition of this invention, its combination with the present invention is contemplated.

In connection with solid tumor treatment, the pharmaceutical compositions of the present invention may be used in combination with classical approaches, such as surgery, radiotherapy, chemotherapy, and the like. The invention therefore provides combined therapies in which a pharmaceutical composition of this invention is used simultaneously with, before, or after surgery or radiation treatment; or is administered to patients with, before, or after conventional chemotherapeutic, radiotherapeutic or anti-angiogenic agents, or targeted immunotoxins or coaguligands.

When one or more agents are used in combination with an antibody-containing composition of this invention in a therapeutic regimen, there is no requirement for the combined results to be additive of the effects observed when each treatment is conducted separately. Although at least additive effects are generally desirable, any increased anti-cancer effect above one of the single therapies would be of benefit. Also, there is no particular requirement for the combined treatment to exhibit synergistic effects, although this is possible and advantageous.

To practice combined anti-cancer therapy, one would simply administer to a patient an antibody composition of this invention in combination with another anti-cancer agent in a manner effective to result in their combined anti-cancer actions within the animal. The agents would therefore be provided in amounts effective and for periods of time effective to result in their combined presence within the tumor vasculature and their combined actions in the tumor environment. To achieve this goal, an antibody composition of this invention and anti-cancer agents may be administered to the patient simultaneously, either in a single combined composition, or as two distinct compositions using the same or different administration routes.

Alternatively, the administration of an antibody composition of this invention may precede, or follow, the anti-cancer agent treatment by, e.g., intervals ranging from minutes to weeks and months. One would ensure that the anti-cancer agent and an antibody in the antibody composition of this invention exert an advantageously combined effect on the cancer. As an example, mAbs of the present invention may be administered to patients with Non-Hodgkin's Lymphoma (NHL). Such patients are typically treated with a combination of Rituximab and a combination of chemotherapy agents known as CHOP. Accordingly, anti-KIR antibodies of this invention may be used to treat NHL patients who are undergoing treatment with Rituximab and CHOP, by combining the administration of all the agents in a treatment schedule where the agents are given on the same day, or on different days, with a longer treatment-period.

Other anti-cancer agents may be given prior to, at the same time as, or following administration of an anti-KIR antibody composition of this invention. However, when immunoconjugates of an antibody are used in the antibody composition of this invention, various anti-cancer agents may be simultaneously or subsequently administered.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administration of the anti-cancer agent or anti-cancer treatment and the administration of an antibody composition of this invention. This might be advantageous in circumstances where the anti-cancer treatment was intended to substantially destroy the tumor, such as surgery or chemotherapy, and administration of an antibody composition of this invention was intended to prevent micrometastasis or tumor re-growth.

It also is envisioned that more than one administration of either an anti-KIR antibody-based composition of this invention or the anti-cancer agent will be utilized. These agents may be administered interchangeably, on alternate days or weeks; or a cycle of treatment with an anti-KIR antibody composition of this invention, followed by a cycle of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within cancer cells is contemplated, such as gamma-irradiation, X-rays, UV-irradiation, microwaves and even electronic emissions and the like. The directed delivery of radioisotopes to cancer cells is also contemplated, and this may be used in connection with a targeting antibody or other targeting means.

In other aspects, immunomodulatory compounds or regimens may be administered in combination with or as part of the antibody compositions of the present invention. Preferred examples of immunomodulatory compounds include cytokines. Various cytokines may be employed in such combined approaches. Examples of cytokines useful in the combinations contemplated by this invention include IL-1 alpha IL-1 beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma. Cytokines used in the combination treatment or compositions of this invention are administered according to standard regimens, consistent with clinical indications such as the condition of the patient and relative toxicity of the cytokine. Other immunomodulatory compounds that may be administered in combination with, or as part of, the antibody compositions of the present invention include antibodies that bind specifically to other inhibitory receptors on lymphocytes, including without limitation antibodies such as anti-CTLA4 antibodies, or anti-CD94/NKG2A antibodies (see, for example, U.S. published patent application 20030095965). Variants and derivatives of these molecules that are known in the art also or alternatively can be used in such methods, and incorporated into compositions of the invention, as appropriate.

In certain embodiments, the cross-reacting, blocking, and/or inhibitory anti-KIR antibody-comprising therapeutic compositions of the present invention may be administered in combination with or may further comprise a chemotherapeutic or hormonal therapy agent. A variety of hormonal therapy and chemotherapeutic agents may be used in the combined treatment methods disclosed herein. Chemotherapeutic agents contemplated as exemplary include, but are not limited to, alkylating agents, antimetabolites, cytotoxic antibiotics, vinca alkaloids, for example adriamycin, dactinomycin, mitomycin, caminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof.

Hormonal agents include, but are not limited to, for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol.

As will be understood by those of ordinary skill in the art, the appropriate doses of chemotherapeutic agents will approximate those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m2 for 5 days every three weeks for a total of three courses. Cisplatin is not absorbed orally and must therefore be delivered via injection intravenously, subcutaneously, intratumorally or intraperitoneally.

Further useful chemotherapeutic agents include compounds that interfere with DNA replication, mitosis and chromosomal segregation, and agents that disrupt the synthesis and fidelity of polynucleotide precursors. A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. The skilled artisan is directed to "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

The present cross-reacting, blocking, and/or inhibitory anti-KIR antibody compositions of this invention may be used in combination with any one or more anti-angiogenic therapies or may further comprise anti-angiogenic agents. Examples of such agents include neutralizing antibodies, antisense RNA, siRNA, RNAi, RNA aptamers and ribozymes each directed against VEGF or VEGF receptors (U.S. Pat. No. 6,524,583, the disclosure of which is incorporated herein by reference). Variants of VEGF with antagonistic properties may also be employed, as described in WO 98/16551, specifically incorporated herein by reference. Further exemplary anti-angiogenic agents that are useful in connection with combined therapy are listed in Table D of U.S. Pat. No. 6,524,583, the disclosure of which agents and indications are specifically incorporated herein by reference.

The anti-KIR antibody compositions of this invention may also be advantageously used in combination with methods to induce apoptosis or may comprise apoptotic agents. For example, a number of oncogenes have been identified that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650, 491; and 5,539,094; each incorporated herein by reference) and family members including Bcl-x1, Mcl-1, Bak, A1, and A20. Overexpression of bcl-2 was first discovered in T cell lymphomas. The oncogene bcl-2 functions by binding and inactivating Bax, a protein in the apoptotic pathway. Inhibition of bcl-2 function prevents inactivation of Bax, and allows the apoptotic pathway to proceed. Inhibition of this class of oncogenes, e.g., using antisense nucleotide sequences, RNAi, siRNA or small molecule chemical compounds, is contemplated for use in the present invention to give enhancement of apoptosis (U.S. Pat. Nos. 5,650,491; 5,539,094; and 5,583, 034; each incorporated herein by reference).

The anti-KIR antibody compositions of this invention may also comprise or be used in combination with molecules that comprise a targeting portion, e.g., antibody, ligand, or conjugate thereof, directed to a specific marker on a target cell ("targeting agent"), for example a target tumor cell. Generally speaking, targeting agents for use in these additional aspects of the invention will preferably recognize accessible tumor antigens that are preferentially, or specifically, expressed in the tumor site. The targeting agents will generally bind to a surface-expressed, surface-accessible or surface-localized component of a tumor cell. The targeting agents will also preferably exhibit properties of high affinity; and will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "not exert significant side effects," as used herein, refers to the fact that a targeting agent, when administered in vivo, will produce only negligible or clinically manageable side effects, such as those normally encountered during chemotherapy.

In the treatment of tumors, an antibody composition of this invention may additionally comprise or may be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

In another embodiment, two or more antibodies of this invention recognizing different epitopes or determinants, including NKVSF1, DF200, 1-4F1 and/or 1-7F9, may be combined in a single composition so as to reduce or neutralize the inhibitory effects of as many KIR gene products as possible. Compositions comprising combinations of cross-reactive inhibitory KIR antibodies of this invention, or fragments or derivatives thereof, will allow even wider utility because there likely exists a small percentage of the human population that may lack each of the inhibitory KIR gene products recognized by a single cross-reacting antibody. Similarly, an antibody composition of this invention may further comprise one or more antibodies that recognize single inhibitory KIR subtypes. Such combinations would again provide wider utility in a therapeutic setting. Accordingly, an antibody of this invention can be combined with another anti-KIR antibody binding to one or more of, e.g., KIR2DL1, KIR2DLK2, KIR2DL3, KIR3DL1, KIR3DL2, and KIR3DL3.

The invention also provides a method of potentiating NK cell activity in a patient in need thereof, comprising the step of administering a composition according to this invention to said patient. The method is more specifically directed at increasing NK cell activity in patients having a disease in which increased NK cell activity is beneficial, which involves, affects or is caused by cells susceptible to lysis by NK cells, or which is caused or characterized by insufficient NK cell activity, such as a cancer, another proliferative disorder, an infectious disease or an immune disorder. More specifically, the methods of the present invention are utilized for the treatment of a variety of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Other preferred disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. The cross-reacting inhibitory KIR antibody of this invention can be used to treat or prevent infectious diseases, including preferably any infections caused by viruses, bacteria, protozoa, molds or fungi. Such viral infectious organisms include, but are not limited to, hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, cytomegalovirus, echinovirus, arbovirus, hantavirus, coxsackie virus, mumps virus, measles virus, rubella virus, polio virus, Ebola-virus, and human immunodeficiency virus type 1 or type 2 (HIV-1, HIV-2).

Bacterial infections that can be treated according to this invention include, but are not limited to, infections caused by the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponerna; Camplyobacter, Pseudomonas* including *Raeruginosa; Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. fickettsfi, Chlamydia* including *C. psittaci* and *C. trachornatis; Mycobacterium* including *M. tuberculosis, M. intracellulare, M. folluiturn, M. laprae, M. avium, M. bovis, M. africanum, M. kansasii, M. intracellulare,* and *M. lepraernurium*; and *Nocardia*.

Protozoa infections that may be treated according to this invention include, but are not limited to, infections caused by *leishmania, kokzidioa,* and *trypanosoma*. A complete list of infectious diseases can be found on the website of the National Center for Infectious Disease (NCID) at the Center for Disease Control (CDC) (World Wide Web (www) at cdc.gov/ncidod/diseases/), which list is incorporated herein by reference. All of said diseases are candidates for treatment using the cross-reacting inhibitory KIR antibodies of the invention.

Such methods of treating various infectious diseases may employ the antibody composition of this invention, either alone or in combination with other treatments and/or therapeutic agents known for treating such diseases, including anti-viral agents, anti-fungal agents, antibacterial agents, antibiotics, anti-parasitic agents and anti-protozoal agents. When these methods involve additional treatments with additional therapeutic agents, those agents may be administered together with the antibodies of this invention as either a single dosage form or as separate, multiple dosage forms. When administered as a separate dosage form, the additional agent may be administered prior to, simultaneously with, of following administration of the antibody of this invention.

Further aspects and advantages of this invention will be disclosed in the following experimental section, which should be regarded as illustrative and not limiting the scope of this application.

EXAMPLES

Example 1

Purification of PBLs and Generation of Polyclonal or Clonal NK Cell Lines

PBLs were derived from healthy donors by Ficoll-Hypaque gradients and depletion of plastic adherent cells. To obtain enriched NK cells, PBLs were incubated with anti-CD3, anti-CD4 and anti-HLA-DR mAbs for 30 minutes at 4° C., followed by incubation with goat anti-mouse magnetic beads (Dynal) (30 minutes at 4° C.) and immunomagnetic selection by methods known in the art (Pende et al., J Exp Med 1999; 190:1505-1516). CD3$^-$, CD4$^-$, DR$^-$ cells were cultivated on irradiated feeder cells and 100 U/ml Interleukin 2 (Proleukin, Chiron Corporation) and 1.5 ng/ml Phytohemagglutinin A (Gibco BRL) to obtain polyclonal NK cell populations. NK cells were cloned by limiting dilution and clones of NK cells were characterized by flow cytometry for expression of cell surface receptors.

The mAbs used were JT3A (IgG2a, anti-CD3), EB6 and GL183 (IgG1, anti-KIR2DL1 and KIR2DL3, respectively), XA-141 (IgM, anti-KIR2DL1 with the same specificity as EB6), anti-CD4 (HP2.6), and anti-DR (D1.12, IgG2a). Instead of JT3A, HP2.6, and DR1.12, other commercially available mAbs of the same specificities can be used. EB6 and GL183 are commercially available (Beckman Coulter Inc., Fullerton, Calif.). XA-141 is not commercially available, but mAb EB6 can equally well be used for control reconstitution of lysis, as shown in the examples and Figures herein, as described by Moretta et al., J Exp Med 1993; 178:597-604.

Cells were stained with the appropriate antibodies (30 nms at 4° C.) followed by PE- or FITC-conjugated polyclonal anti-mouse antibodies (Southern Biotechnology Associates Inc). Samples were analyzed by cytofluorometric analysis (flow cytometry) on a FACScan apparatus (Becton Dickinson, Mountain View, Calif.).

The following NK cell clones were used in this study. CP11, CN5 and CN505 are KIR2DL1 positive clones and are stained by EB6 (IgG1, anti-KIR2DL1) or XA-141 (IgM, anti KIR2DL1 with same specificity as compared to EB6 antibodies). CN12 and CP502 are KIR2DL3-expressing NK clones and are stained by GL183 antibody (IgG1, anti-KIR2DL2/3).

The cytolytic activity of NK clones was assessed by a standard 4-hour 51Cr-release assay in which effector NK cells were tested for their ability to kill target cells expressing HLA-Cw3 or -Cw4, HLA positive cell lines known for their sensitivity to NK cell lysis. All the targets were used at 5000 cells per well in microtitration 96-well plates and the effector: target ratio is indicated in the Figures (usually 4 effectors per target cells). The cytolytic assay was performed with or without hybridoma supernatant of the indicated monoclonal antibodies at a ½ (1:1) dilution. The procedure was essentially the same as described in Moretta et al., J Exp Med 1993; 178: 597-604.

Example 2

Generation of New mAbs mAbs were generated by immunizing 5 week old Balb/C mice with activated polyclonal or monoclonal human NK cell lines as described in (Moretta et al., J Exp Med 1990; 172: 1589-1598). After different cell fusions, the mAbs were first selected for their ability to cross-react with EB6- and GL183-positive NK cell lines and clones. Positive monoclonal antibodies were further screened for their ability to reconstitute lysis by EB6-positive or GL183-positive NK clones of Cw4 or Cw3 positive targets, respectively.

Cell staining was carried out as follows. Cells were stained with a panel of antibodies (1 µg/ml or 50 µl supernatant, 30 nms at 4° C.) followed by PE-conjugated goat F(ab')2 fragments anti-mouse IgG (H+L) or PE-conjugated goat F(ab')2 fragment anti-human IgG (Fc gamma) antibodies (Beckman Coulter). Cytofluorometric analysis was performed on an Epics XL.MCL apparatus (Beckman Coulter).

One of the monoclonal antibodies, the DF200 mAb, was found to react with various members of the KIR family including KIR2DL1, and KIR2DL2/3. Both KIR2DL1-positive and KIR2DL2/3-positive NK cells were stained brightly with DF200 mAb (FIG. 1).

NK clones expressing one or another (or even both) of these HLA class I-specific inhibitory receptors were used as effectors cells against target cells expressing one or more HLA-C alleles. Cytotoxicity assays were carried out as follows. The cytolytic activity of YTS-KIR2DL1 or YTS-Eco (KIR-negative) cell lines was assessed by a standard 4 hours Cr-51 release assay. The target cells were HLA-Cw4-positive or -negative B-EBV cell lines, or HLA-Cw4-transfected 721.221 cells. All targets were used at 3000 cells per well in microtitration plate. The effector/target ratio is indicated in the figures. The cytolytic assay was performed with or without the indicated full length or F(ab')2 fragments of monoclonal mouse or human antibodies. As expected, KIR2DL1-positive (KIR2DL1$^+$) NK clones displayed little if any cytolytic activity against target cells expressing HLA-Cw4 and KIR2DL3+ NK clones displayed little or no activity on Cw3 positive targets. However, in the presence of DF200 mAb (used to mask their KIR2DL receptors) NK clones became unable to recognize their HLA-C ligands and displayed strong cytolytic activity against Cw3- or Cw4-expressing targets (examples of results are shown in FIGS. 2-6).

Figure 2:
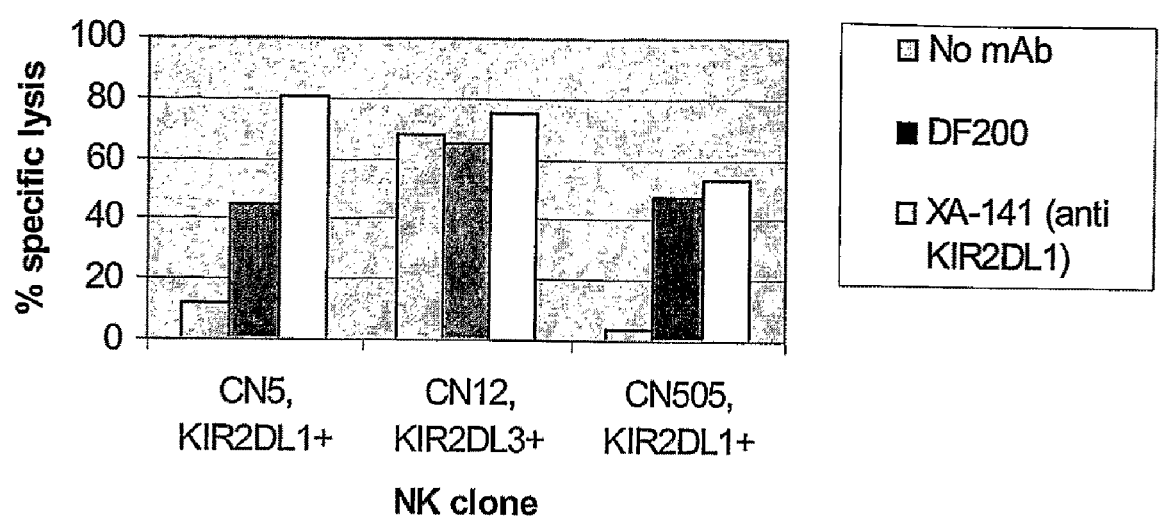
FIG. 2 depicts the murine monoclonal antibody DF200 neutralizing the KIR2DL1-mediated inhibition of NK cell cytotoxicity against Cw4-expressing target cells, showing the reconstitution of lysis with the anti-KIR mAb on CIR-Cw4 target at effector/target (E/T) ratios of 4/1.

For example, the C1R cell line (CW4+ EBV cell line, ATCC No. CRL-1993), which expresses HLA-Cw4 (but no group 1 HLA-C allotypes) was not killed by KIR2DL1-positive NK clones (CN5/CN505), but the inhibition could be efficiently reversed by the use of either DF200 or a conventional anti KIR2DL1 mAb. On the other hand, NK clones expressing the KIR2DL2/3$^+$ KIR2DL1$^-$ phenotype (CN12) efficiently killed C1R cells and this killing was unaffected by the DF200 mAb (FIG. 2). Similar results are obtained with KIR2DL2- or KIR2DL3-positive NK clones on Cw3-positive targets.

Figure 3:
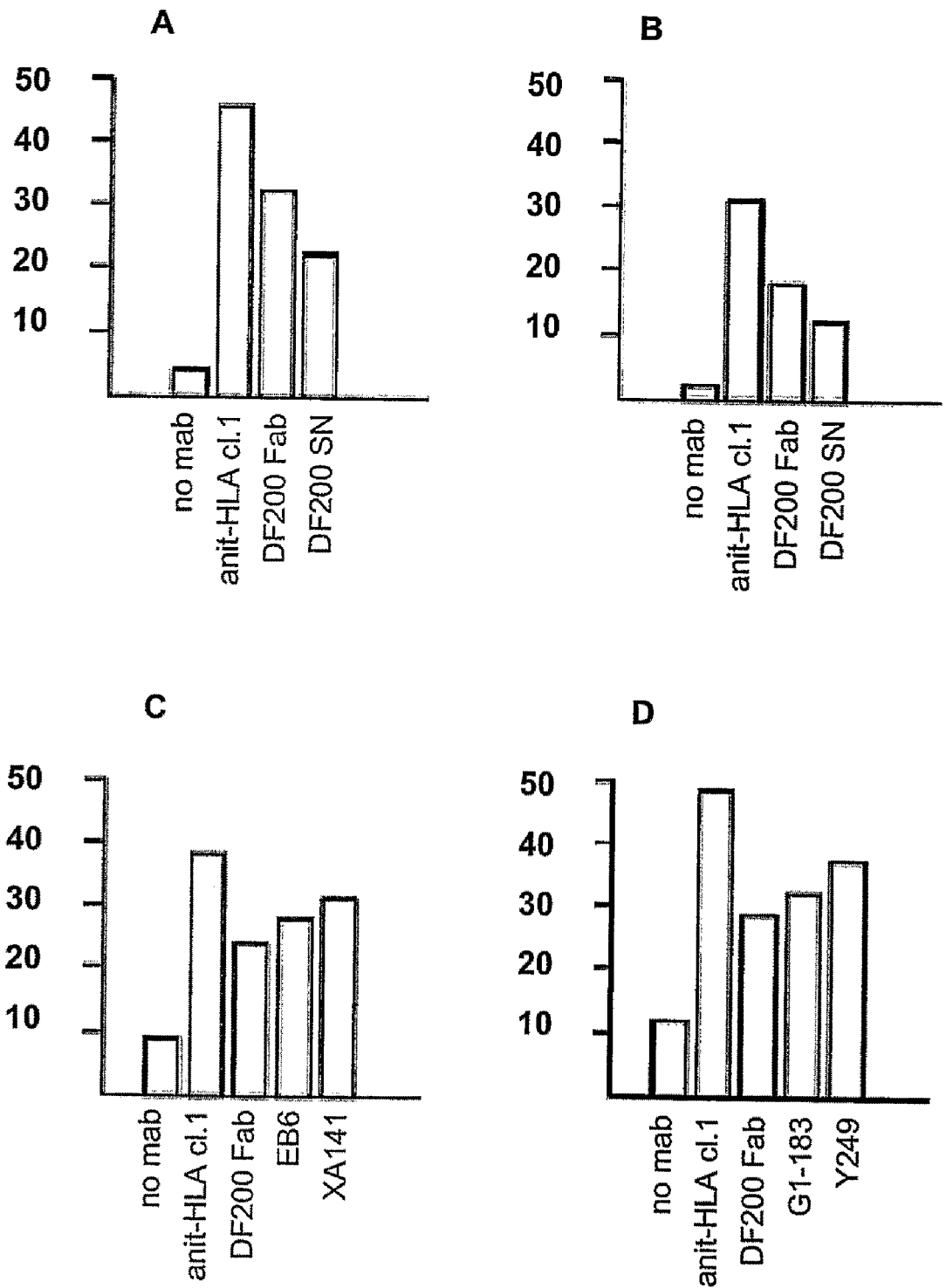
FIG. 3 depicts the murine monoclonal antibody DF200, a Fab fragment of DF200, and conventional murine antibodies specific for either KIR2DL1 (mAbs EB6 and XA-141) or KIR2DL2/3 (mAbs GL183 and Y249) neutralizing the KIR2DL1-mediated inhibition of cytotoxicity against Cw4-positive target cells, and the KIR2DL2/3-mediated inhibition of NK cell cytotoxicity against Cw3-positive target cells. (A) and (C) KIR2DL1+, target cells 721.221-Cw4+. (B) KIR2DL2+, target cells 721.221-Cw3+. (D) KIR2DL3+, target cells 721.221-Cw3+.
Figure 7:
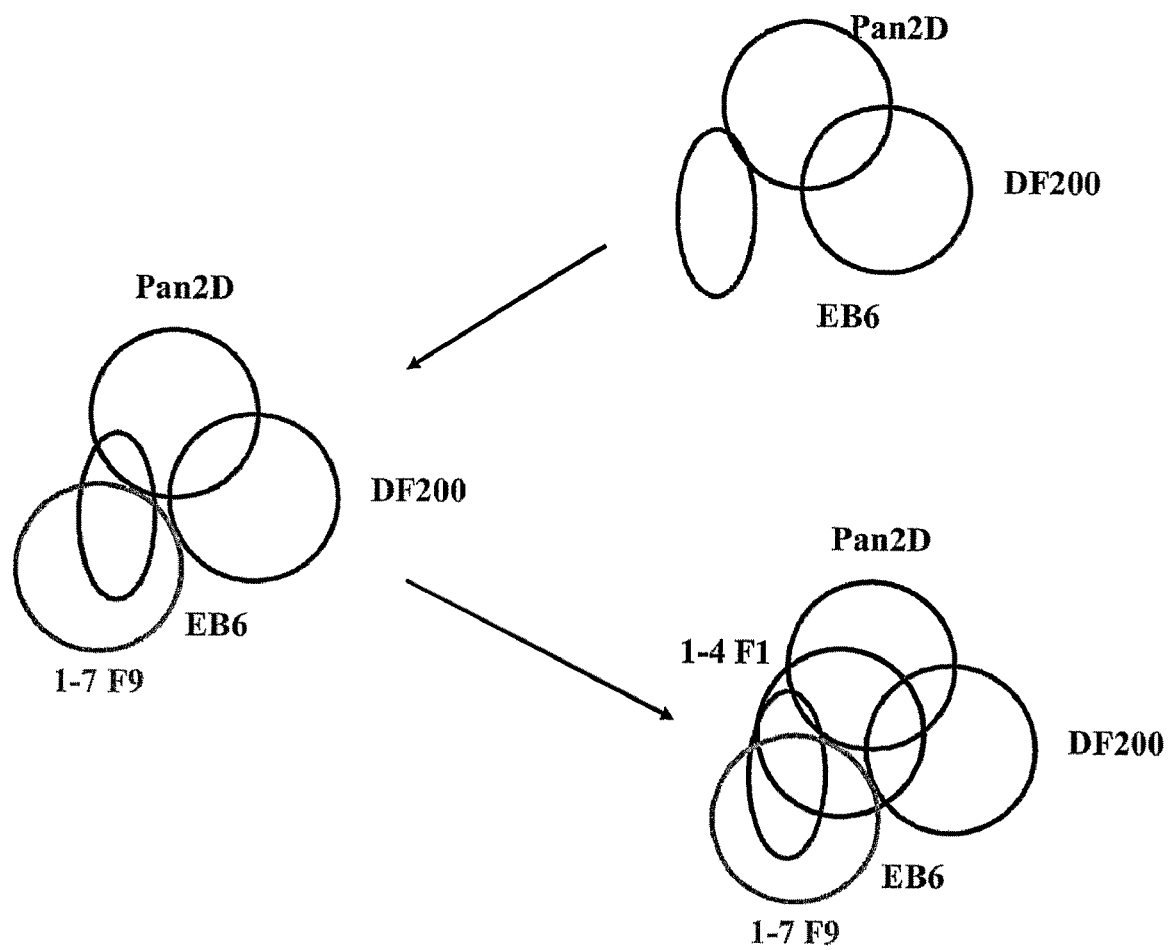
FIG. 7 depicts an epitope map showing results of competitive binding experiments obtained by surface plasmon resonance (BIAcore®) analysis with anti-KIR antibodies to KIR2DL1, where overlapping circles designate overlap among the mAbs in binding to KIR2DL1. Results show that 1-7F9 is competitive with EB6 and 1-4F1, but not with NKVSF1 (Pan2D) and DF200, on KIR2DL1. Antibody 1-4F1 in turn is competitive with EB6, DF200, NKVSF1 (Pan2D), and 1-7F9. Antibody NKVSF1 (Pan2D) competes with DF200, 1-4F1, and EB6, but not 1-7F9, on KIR2DL1. DF200 competes with NKVSF1 (Pan2D), 1-4F1, and EB6, but not 1-7F9, on KIR2DL1.

Similarly, the Cw4+ 221 EBV cell line was not killed by KIR2DL1+ transfected NK cells, but the inhibition could be efficiently reversed by the use of the DF200 mAb, a Fab fragment of DF200, or the a conventional anti-KIR2DL1 mAbs EB6 or XA141. Also, a Cw3-positive 721.221-transfectant was not killed by KIR2DL2$^+$ NK cells, but this inhibition could be reversed by the use of either DF200 or a DF200 Fab fragment. Finally, the Cw3+ 721.221-transfectant was not killed by KIR2DL3$^+$ NK cells, but this inhibition could be reversed by the use of either a DF200 Fab fragment or the conventional anti-KIR2DL3 mAb GL183 or Y249. The results are shown in FIG. 3.

F(ab')2 fragments were also tested for their ability to reconstitute lysis of Cw4 positive targets. F(ab')2 fragments of the DF200 and EB6 Abs were both able to reverse inhibition of lysis by KIR2DL1-transfected NK cells of the Cw4 transfected 221 cell line and the Cw4+ TUBO EBV cell line. Results are shown in FIG. 4.

Example 3

Biacore Analysis of DF200 mAb/KIR2DL1 and DF200 mAb/KIR2DL3 Interactions

Production and purification of recombinant proteins. The KIR2DL1 and KIR2DL3 recombinant proteins were produced in *E. coli*. cDNA encoding the entire extracellular domain of KIR2DL1 (SEQ ID NO:23) and KIR2DL3 (SEQ ID NO:25) were amplified by PCR from pCDM8 clone 47.11 vector (Biassoni et al, Eur J Immunol. 1993; 23:1083-7) and RSV.5(gpt)183 clone 6 vector (Wagtmann et al, Immunity 1995; 2:439-49 and 1995; 3:801-809) respectively, using the following primers:

(SEQ ID NO: 13)
Sense:
5'-GGAATTCCAGGAGGAATTTAAAATGCATGAGGGAGTCCACAG-3'

Anti-sense:
(SEQ ID NO: 14)
5'- CGGGATCCCAGGTGTCTGGGGTTACC -3'

They were cloned into the pML1 expression vector in frame with a sequence encoding a biotinylation signal (Saulquin et al, J Exp Med. 2003; 197:933-8).

Protein expression was performed in the BL21(DE3) bacterial strain (Invitrogen). Transfected bacteria were grown to OD600=0.6 at 37° C. in medium supplemented with ampicillin (100 µg/ml) and expression was induced with 1 mM IPTG.

Proteins were recovered from inclusion bodies under denaturing conditions (8 M urea). Refolding of the recombinant proteins was performed in 20 mM Tris, pH 7.8, NaCl 150 mM buffer containing L-arginine (400 mM, Sigma) and β-mercaptoethanol (1 mM), at room temperature, by decreasing the urea concentration in a six step dialysis (4, 3, 2, 1 0.5 and 0 M urea, respectively). Reduced and oxidized glutathione (5 mM and 0.5 mM respectively, Sigma) were added during the 0.5 and 0 M urea dialysis steps. Finally, the proteins were dialyzed extensively against 10 mM Tris, pH 7.5, NaCl 150 mM buffer. Soluble, refolded proteins were concentrated and then purified on a Superdex 200 size-exclusion column (Pharmacia; AKTA system).

Surface plasmon resonance measurements were performed on a Biacore apparatus (Biacore). In all Biacore experiments HBS buffer supplemented with 0.05% surfactant P20 served as running buffer.

Protein immobilisation. Recombinant KIR2DL1 and KIR2DL3 proteins produced as described above were immobilized covalently to carboxyl groups in the dextran layer on a Sensor Chip CM5 (Biacore). The sensor chip surface was activated with EDC/NHS (N-ethyl-N'-(3-dimethylaminopropyl)carbodiimidehydrochloride and N-hydroxysuccinimide, Biacore). Proteins, in coupling buffer (10 mM acetate, pH 4.5) were injected. Deactivation of the remaining activated groups was performed using 100 mM ethanolamine pH 8 (Biacore).

Affinity measurements. For kinetic measurements, various concentrations of the soluble antibody (1×10-7 to 4×10-10 M) were applied onto the immobilized sample. Measurements were performed at a 20 µl/min continuous flow rate. For each cycle, the surface of the sensor chip was regenerated by 5 µl injection of 10 mM NaOH pH 11. The BIAlogue Kinetics Evaluation program (BIAevaluation 3.1, Biacore) was used for data analysis. The soluble analyte (40 µl at various concentrations) was injected at a flow rate of 20 µl/min in HBS buffer, on dextran layers containing 500 or 540 reflectance units (RU), and 1000 or 700 RU of KIR2DL1 and KIR2DL3, respectively. Data are representative of 6 independent experiments. The results are shown in Table 1, below.

TABLE 1

BIAcore analysis of DF200 mAb binding to immobilized KIR2DL1 and KIR2DL3. $K_D$: Dissociation constant.

| Protein | $K_D (10^{-9} M)$ |
|---|---|
| KIR2DL1 | 10.9 +/− 3.8 |
| KIR2DL3 | 2.0 +/− 1.9 |

Example 4

Generation of New Human Anti-KIR mAbs

Human monoclonal anti-KIR mAbs were generated by immunizing transgenic mice, engineered to express a human antibody repertoire, with recombinant, soluble KIR proteins. After different cell fusions to establish hybridomas, mAbs were first selected for their ability to cross-react with immobilized KIR2DL1 and KIR2DL3 protein (produced as described in Example 3, above). Several human monoclonal antibodies, including 1-7F9, 1-4F1, 1-6F5 and 1-6F1, were found to be cross-reactive with KIR2DL1 and KIR2DL2/3.

Positive monoclonal antibodies were further screened for their ability to reconstitute lysis by KIR2DL1-positive NK transfectants against Cw4-positive target cells. The NK cells expressing the HLA class I-specific inhibitory receptors were used as effectors cells against target cells expressing one or more HLA-C alleles (FIGS. 5 and 6). Cytotoxicity assays were carried out as described above. The effector/target ratio is indicated in the figure legends, and antibodies were used at either 10 µg/ml or 30 µg/ml.

As expected, KIR2DL1+ NK cells displayed little if any cytolytic activity against target cells expressing HLA-Cw4. However, in the presence of 1-7F9 mAb, NK cells became unable to recognize their HLA-C (i.e., were no longer inhibited by HLA-C molecules), and now displayed strong cytolytic activity against the Cw4-positive targets. For example, the two cell lines tested (the HLA-Cw4 transfected 721.221 and the CW4+ EBV cell lines) were not killed by KIR2DL1+ NK cells, but the inhibition could be efficiently reversed by the use of either mAb 1-7F9 or the conventional anti-KIR2DL1 mAb EB6. The murine mAbs DF200 and Pan2D (NKVSF1) were compared to the human mAb 1-7F9 and in all experiments 1-7F9 was more potent than any of the other mAbs tested in terms of inducing cytotoxicity by the NK cells. Antibodies 1-4F1, 1-6F5 and 1-6F1 on the other hand were not able to reconstitute cell lysis by NK cells against Cw4-positive targets.

Example 5

Biacore Competitive Binding Analysis of Murine and Human Anti-KIR Antibodies

Epitope mapping analysis was performed according to a previously described method (Gauthier et al., Journal of Immunology 1999; 162:41-50; Saunal and van Regenmortel, Journal of Immunology 1995; 183:33-41) on immobilized KIR2DL1 (900 RU), KIR 2DL3 (2000 RU) and KIR2DS1 (1000 RU) with mouse anti-KIR 2D antibodies DF200, NKVSF1 (Pan2D), gl183 and EB6, and human anti-KIR2D antibodies 1-4F1, 1-6F1, 1-6F5 and 1-7F9.

All experiments were done at a flow rate of 5 µl/min in HBS buffer with 2 min injection of the different antibodies at 15 µg/ml. For each pair of antibodies, competitive binding analysis was performed in two steps. In the first step the first monoclonal antibody (mAb) was injected on KIR2D target protein followed by the second mAb (without removing the first mAb) and second mAb RU value (RU2) was monitored. In the second step the second mAb was injected first, directly on nude KIR2D protein, and mAb RU value (RU1) was monitored. Percent inhibition of second mAb binding to KIR2D protein by first mab was calculated by: 100*(1−RU2/RU1).

Results are shown in Tables 2, 3 and 4, where the antibodies designated "first antibody" are listed on vertical column and the 'second antibody' are listed on the horizontal column. For each antibody combination tested, the values for direct binding level (RU) of the antibodies to the chip are listed in the table, where direct binding of the second antibody to the KIR2D chip is listed in the upper portion of the field and the value for binding of the second antibody to the KIR2D chip when the first antibody is present is listed in the lower portion of the field. Listed in the right of each field is the percentage inhibition of second antibody binding. Table 2 shows binding on a KIR2DL1 chip, Table 3 shows binding of antibodies to a KIR2DL3 chip, and Table 4 shows binding of antibodies to a KIR2DS1 chip.

Figure 8:
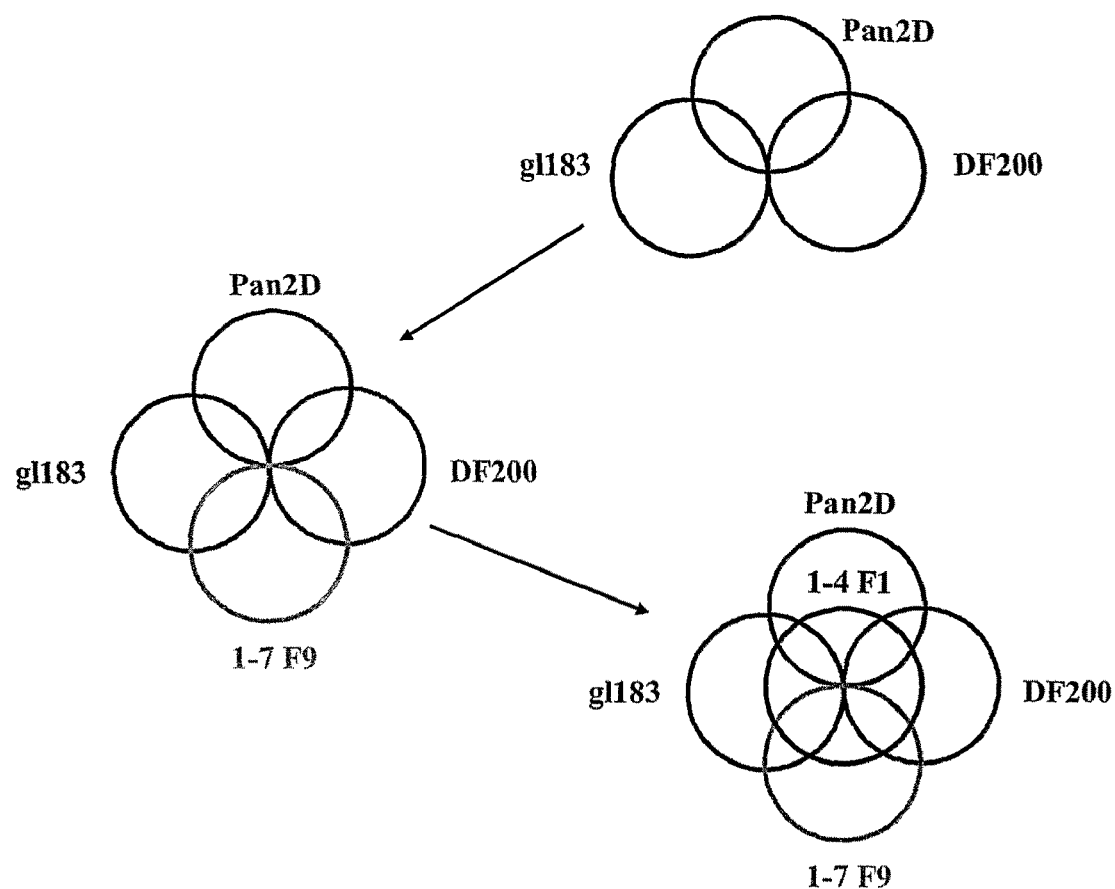
FIG. 8 depicts an epitope map showing results of competitive binding experiments obtained by BIAcore® analysis with anti-KIR antibodies to KIR2DL3, where overlapping circles designate overlap in binding to KIR2DL3. Results show that 1-4F1 is competitive with NKVSF1 (Pan2D), DF200, gl83, and 1-7F9 on KIR2DL3. 1-7F9 is competitive with DF200, gl83, and 1-4F1, but not with NKVSF1 (Pan2D), on KIR2DL3. NKVSF1 (Pan2D) competes with DF200, 1-4F1, and GL183, but not 1-7F9, on KIR2DL3. DF200 competes with NKVSF1 (Pan2D), 1-4F1, and 1-7F9, but not with GL183, on KIR2DL3.
Figure 9:
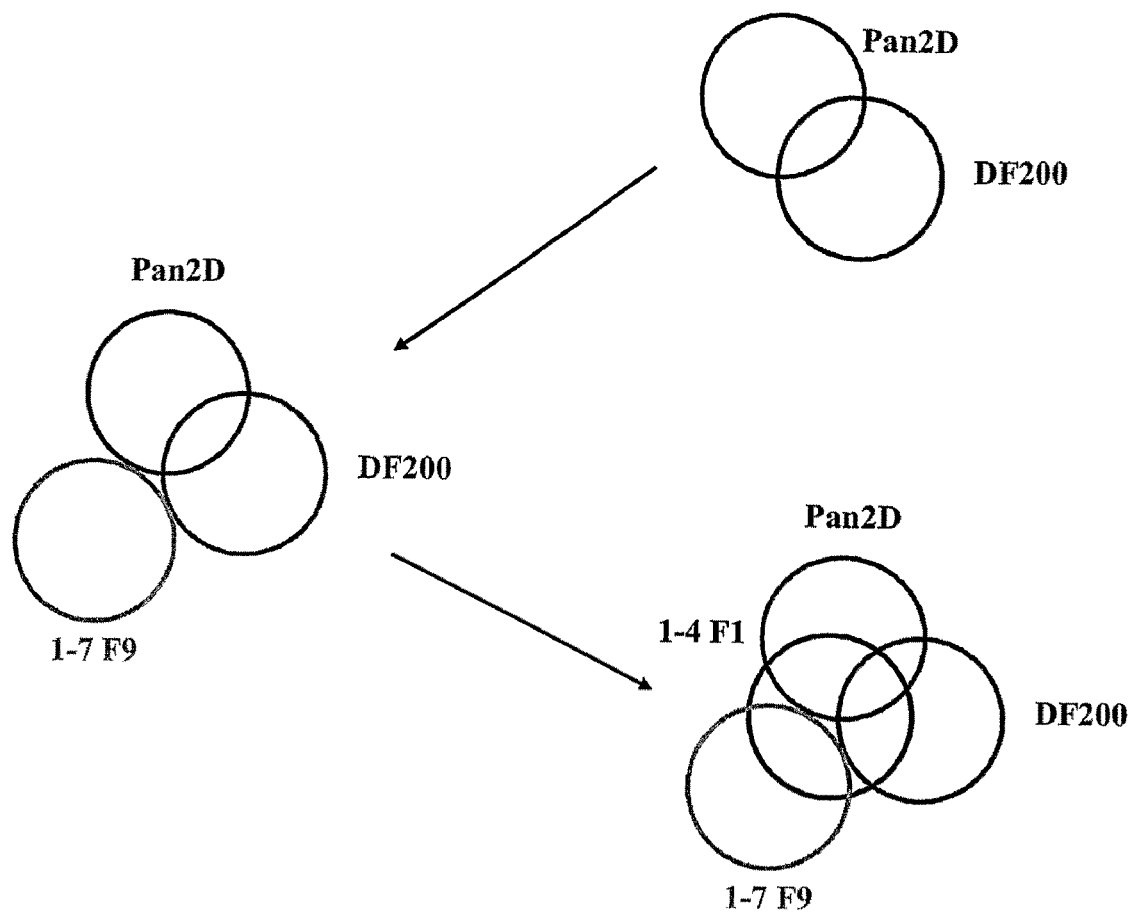
FIG. 9 depicts an epitope map showing results of competitive binding experiments obtained by BIAcore® analysis with anti-KIR antibodies to KIR2DS1, where overlapping circles designate overlap in binding to KIR2DS1. Results show that antibody 1-4F1 is competitive with NKVSF1 (Pan2D), DF200, and 1-7F9 on KIR2DS1. Antibody 1-7F9 is competitive with 1-4F1, but not competitive with DF200 and NKVSF1 (Pan2D) on KIR2DS1. NKVSF1 competes with DF200 and 1-4F1, but not with 1-7F9, on KIR2DS1. DF200 competes with NKVSF1 and 1-4F1, but not with 1-7F9, on KIR2DS1.

Competitive binding of murine antibodies DF200, NKVSF1 and EB6, and human antibodies 1-4F1, 1-7F9 and 1-6F1 to immobilized KIR2DL1, KIR2DL2/3 and KIR2DS1 was assessed. Epitope mapping (FIG. 7) from experiments with anti-KIR antibodies' binding to KIR2DL1 showed that (a) antibody 1-7F9 is competitive with EB6 and 1-4F1, but not with NKVSF1 and DF200; (b) antibody 1-4F1 in turn is competitive with EB6, DF200, NKVSF1 and 1-7 F9; (c) NKVSF1 competes with DF200, 1-4F1 and EB6, but not 1-7F9; and (d) DF200 competes with NKVSF1, 1-4F1 and EB6, but not 1-7F9. Epitope mapping (FIG. 8) from experiments with anti-KIR antibodies' binding to KIR2DL3 showed that (a) 1-4F1 is competitive with NKVSF1, DF200, gl183 and 1-7F9; (b) 1-7F9 is competitive with DF200, gl183 and 1-4F1, but not with NKVSF1; (c) NKVSF1 competes with DF200, 1-4F1 and GL183, but not 1-7F9; and (d) DF200 competes with NKVSF1, 1-4F1 and 1-7F9, but not with GL183. Epitope mapping (FIG. 9) from experiments with anti-KIR antibodies' binding to KIR2DS1 showed that (a) 1-4F1 is competitive with NKVSF1, DF200 and 1-7F9; (b) 1-7F9 is competitive with 1-4F1 but not competitive with DF200 and NKVSF1; (c) NKVSF1 competes with DF200 and 1-4F1, but not 1-7F9; and (d) DF200 competes with NKVSF1 and 1-4F1, but not with 1-7F9.

Example 6

Anti-KIR mAb Titration with Cynomolgus NK Cells

Anti-KIR antibody NKVSF1 was tested for its ability to bind to NK cells from cynomolgus monkeys.

TABLE 2

KIR2DL1 epitope mapping using competitive binding between first and second antibodies (ND = not determined).

| First Ab (below) | Second Ab | | | | | | |
|---|---|---|---|---|---|---|---|
| | DF200 | Pan2D | EB6 | 1-4F1 | 1-7F9 | 1-6F1 | 1-6F5 |
| DF200 | | 80% | 90% | 490/40 92% | 480/350 27% | 540/460 15% | 400/340 15% |
| Pan2D | 90% | | 90% | 900/50 95% | 860/840 2% | 750/660 12% | 600/520 13% |
| EB6 | 60% | 40% | | 460/200 57% | 370/190 48% | 490/170 65% | 260/200 23% Nd |
| 1-4F1 | | | | | | | |
| 1-7F9 | 600/545 10% | 545/534 2% | 460/180 60% | 360/16 95% | | 330/300 9% | Nd |
| 1-6F1 | 350/310 11% | 475/440 7% | 260/320 18% | 360/275 23% | 490/440 10% | | Nd |
| 1-6F5 | 350/290 17% | 475/440 7% | Nd | 360/300 17% | Nd | 290/170 40% | |

TABLE 3

KIR2DL3 epitope mapping using competitive binding between first and second antibodies (ND = not determined)

| First Ab (below) | Second Ab | | | | | | |
|---|---|---|---|---|---|---|---|
| | DF200 | Pan2D | GI183 | 1-4F1 | 1-7F9 | 1-6F1 | 1-6F5 |
| DF200 | | 75% | 20% | 1270/320 75% | 520/200 62% | 550/460 16% | 440/420 4% |
| Pan2D | 95% | | 85% | 2250/730 68% | 880/750 15% | 840/770 8% | 560/460 18% |
| gI183 | 8% | 40% | | 1300/330 75% | 670/160 76% | 530/430 18% | Nd |
| 1-4F1 | 1140/210 82% | 2400/890 63% | 1240/330 73% | | 1050/140 87% | | |
| 1-7F9 | 770/450 42% | 870/830 5% | 800/200 75% | 1000/270 63% | | | |
| 1-6F1 | 790/760 4% | 990/1090 0% | 620/570 8% | | | | |
| 1-6F5 | 800/760 5% | 990/950 4% | Nd | | | | |

TABLE 4

KIR2DS1 epitope mapping using competitive binding between first and second antibodies (ND = not determined)

| First Ab (below) | Second Ab | | | |
|---|---|---|---|---|
| | DF200 | Pan2D | 1-4F1 | 1-7F9 |
| DF200 | | 70% | 660/80 87% | 975/825 15% |
| Pan2D | 100% | | 650/−8 100% | 920/500 45% |
| 1-7F9 | 900/1090 17% | 1350/1200 11% | 660/23 96% | |

Purification of monkey PBMC and generation of polyclonal NK cell bulk. Cynomolgus Macaque PBMC were prepared from Sodium citrate CPT tube (Becton Dickinson). NK cells purification was performed by negative depletion (Macaque NK cell enrichment kit, Stem Cell Technology). NK cells were cultivated on irradiated human feeder cells with 300 U/ml Interleukin 2 (Proleukin, Chiron Corporation) and 1 ng/ml Phytohemagglutinin A (Invitrogen, Gibco) to obtain polyclonal NK cell populations.

Pan2D mAb titration with cynomolgus NK cells. Cynomolgus NK cells (NK bulk day 16) were incubated with different amount of Pan2D mAb followed by PE-conjugated goat F(ab')2 fragments anti-mouse IgG (H+L) antibodies. The percentage of positive cells was determined with an isotypic control (purified mouse IgG1). Samples were done in duplicate. Mean fluorescence intensity=MFI.

Binding of the antibody to monkey NK cells is shown in FIG. 10.

Example 7

Screening of Human Anti-KIR mAbs

Human monoclonal anti-KIR Abs were generated by immunizing transgenic mice engineered to express a human antibody repertoire with recombinant KIR protein, as described in Example 4. To generate cross-reactive anti-KIR antibodies, animals were sequentially immunized with different KIRs, either in soluble form as described in Example 3, or expressed at the surface of cells.

Next, after different cell fusions, the mAbs were first selected for their ability to cross-react with immobilized KIR2DL1 and KIR2DL3 protein, by ELISA, using standard methods. Several human monoclonal antibodies, including 1-7F9, 1-4F1, 1-6F5 and 1-6F1, were found to react with all of KIR2DL1, KIR2DL2 and KIR2DL3, by ELISA. The mAbs that reacted with both KIR2DL1 and KIR2DL2/3 were designated "KIR2DL-crossreactive mAbs."

Figure 16:
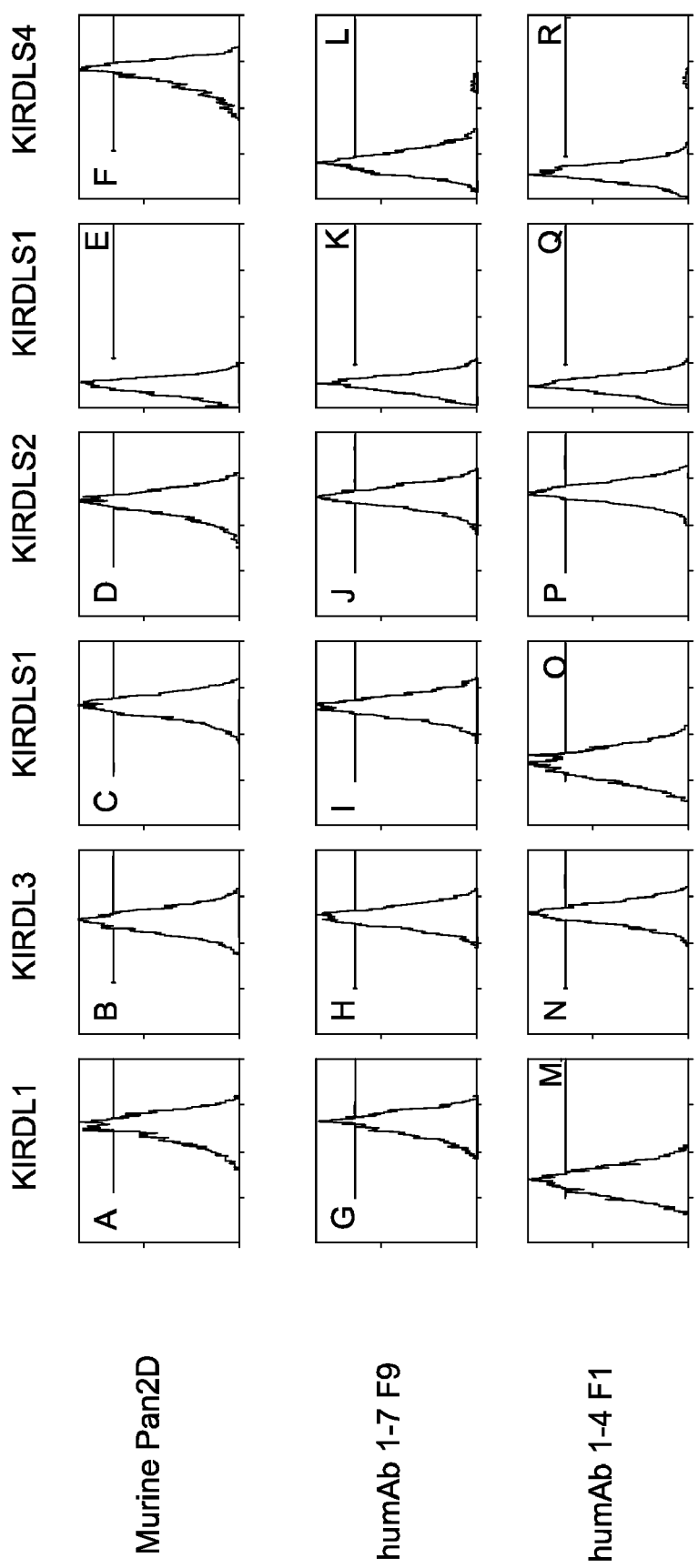
FIG. 16 depicts flow cytometry data, showing binding of the murine antibody, Pan2D (NKVSF1) and the human mAbs 1-7F9 and 1-4F1 to cells transfected with KIR2DL1, KIR2DL3, KIR2DS1, KIR2DS2, KIR2DS3 or KIR2DS4, as indicated (purified antibody: 1 µg/ml). (A)-(R) NKVSF1 (pan2D), 1-7F9, and 1-4F1 all bind to KIR2DL1, KIR2DL3, KIR2DS1, and KIR2DS2. Neither antibody binds to KIR2DS3. NKVSF1, but not 1-7F9 or 1-4F1, binds to KIR2DS4.

The KIR2DL cross-reactive mAbs were then tested for their ability to react with KIR at the surface of cells by flow cytometry. Briefly, the binding of the human anti-KIR mAbs was tested by incubating them with various cell lines stably over-expressing KIRs (e.g., YTS-2DL1, BWZ-KIR2DL2 and BWZ-KIR2DS4) or not expressing KIRs (e.g., YTS and BWZ). Briefly, cells were incubated with various concentrations (typically 0-50 µg/ml) of human anti-KIR mAb1-7F9 in DMEM-medium containing 2% FCS. After incubation, cells were washed and incubated with APC-conjugated secondary antibodies specific for human IgG. All incubations and washing steps were performed at 0-4° C. Subsequently, cells were washed, resuspended in PBS, and analyzed by flow cytometry on a FACScalibur or a FACScanto (both from Beckton Dickinson). A typical example is shown in FIG. 16. For example, 1-7F9 and 1-4F1 were found to not bind to cells transfected with KIR2DS4, whereas NKVSF1 (Pan2D) did (FIG. 16).

Next, the ability of the human anti-KIR mAbs to block the interaction between KIR and its HLA-C ligand was tested by 1) biochemical, direct binding experiments and 2) functional reconstitution of lysis assays.

Figure 17:
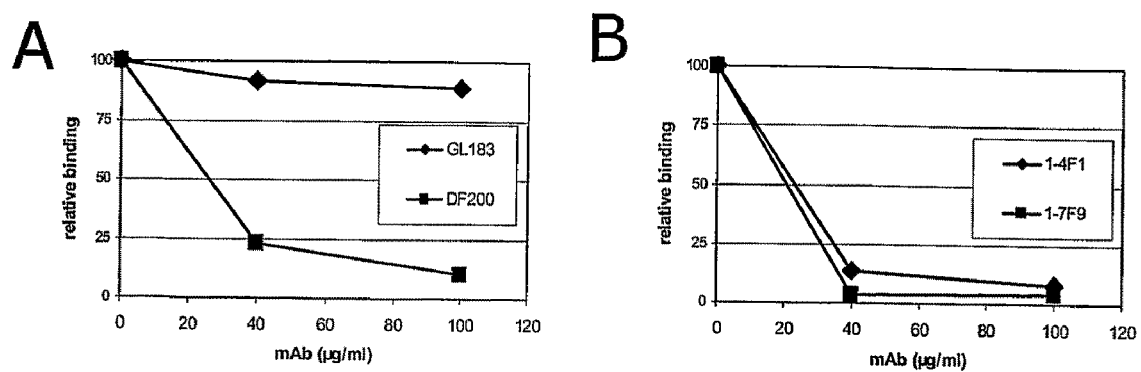
FIG. 17 depicts FACS analysis results. (A) Antibody-mediated neutralization of binding of soluble KIR-Fc to HLA-Cw4 on cells, detected by flow cytometry (FACS). FACS-measurement of KIR2DL1-mFc binding to LCL721.221-Cw4 cells, after pre-incubation with various concentrations of the cross-reactive mAb DF200, or the KIR2DL2/3-specific mAb GL183. DF200, but not GL183, reduces binding of KIR2DL1 to HLA-Cw4. Measurements are plotted as a percentage of KIR2DL1-hFc-binding in the absence of inhibitory antibodies. (B) FACS-measurement of KIR2DL1-mFc binding to LCL721.221-Cw4 cells, after pre-incubation with various concentrations of 1-1F4 and 1-7F9. Measurements are plotted as a percentage of KIR2DL1-mFc-binding in the absence of inhibitory antibodies.

In the biochemical binding assay, the capacity of human anti-KIR mAbs, including 1-7F9, to block the interaction between HLA-C and KIR-molecules was assessed by competing the binding of soluble, recombinant KIR-Fc fusion proteins to cells expressing HLA-C. The KIR-Fc proteins were produced as described (Wagtmann et al., Immunity 1995; 3(6):801-9), except that the human Fc was replaced with murine IgG1 Fc. Soluble KIR-Fc binds to cells expressing the specific HLA-C allotypes that are recognized by KIR2DL1, and this binding can be visualized by flow-cytometry using a secondary fluorochrome-conjugated Ab specific for the murine Fc part of the KIR-Fc protein. For example, KIR2DL1-Fc binds to cells transfected with HLA-Cw*0402 (LCL 721.221-Cw4 transfectants) (Litwin et al., J Exp Med. 1993; 178:1321-36) but not to untransfected LCL 721.221 cells (see FIG. 11A). To test whether anti-KIR mAbs could prevent this interaction between KIR2DL1-Fc and HLA-Cw4, the KIR2DL1-FC proteins were pre-incubated with increasing concentrations of anti-KIR mAbs, and then added to LCL 721.221-Cw4 cells, incubated at 4° C., washed, incubated with an APC-conjugated anti-murine IgG1 Fc, washed, and analyzed by flow cytometry on a FACScalibur, or a FACScanto (Beckton Dickinson), by standard methods. Some murine anti-KIR mAbs, such as DF200, and some human anti-KIR mAbs, namely 1-7F9 and 1-4F1, prevented the binding of KIR2DL1-Fc to the cells expressing HLA-Cw4, showing that these mAbs block the interaction between KIR2DL1 and HLA-Cw4. As an example, FIG. 17A shows that DF200 prevents binding of KIR2DL1-Fc to cells expressing HLA-Cw4. FIG. 17B shows that the 1-7F9 mAbs prevented KIR2DL1 from binding to HLA-Cw4. In parallel, the anti-KIR mAbs were tested for their ability to prevent the binding of KIR2DL2 to HLA-Cw3. Antibodies that prevented the binding of KIR2DL-Fc to HLA-C-expressing cells in a dose-dependent fashion, as exemplified in FIG. 17, were designated "blocking mAbs" and were further tested in functional cytotoxicity assays, as follows.

The therapeutic utility of the human anti-KIR mAbs is linked to their ability to induce KIR-expressing NK cells to kill tumor cells, by preventing inhibitory signaling via KIR. Therefore, it was important to assess whether human KIR2DL cross-reactive and blocking mAbs were able to induce lysis of target cells expressing HLA-C by NK cells expressing KIR2DL. For this purpose, the following experiments were performed:

In $^{51}$Cr-release cytotoxicity assays, KIR2DL1-expressing YTS cells (YTS-2DL1) can kill LCL 721.221-Cw3, but not LCL 721.221-Cw4 cells (FIG. 18A). In contrast, YTS effector-cells that lack KIRs (YTS) kill both cell-lines efficiently. Thus, YTS-2DL1 effector cells cannot kill LCL 721.221-Cw4 cells due to HLA-Cw4-induced inhibitory signaling via KIR2DL1. When YTS-2DL1 cells were pre-incubated with 1-7F9 in $^{51}$Cr-release cytotoxicity assays, LCL 721.221-Cw4 cells were killed in a 1-7F9 concentration-dependent fashion (FIG. 18B). 3-1F13, a human cross-reactive anti-KIR mAb that binds KIR2DL1 with high affinity, but that can not prevent the interaction between KIR2DL1 and HLA-Cw4, can not induce killing of LCL 721.221-Cw4 cells by YTS-2DL1 cells. Thus, 1-7F9 induces NK-mediated killing of target cells by preventing KIR-HLA-C interactions between NK- and target-cells.

Example 8

Affinity Measurements of 1-7F9

The affinity of 1-7F9 for binding to KIR2DL1 and KIR2DL3 was measured by Biacore analysis, using soluble recombinant KIR proteins produced as described in Example 3. The Biacore experiments were performed as described in Example 3, except that the antibody used was the human mAb 1-7F9.

The results of these affinity determinations of binding by 1-7F9 to KIR2DL1 and -3 are shown in Table 5.

TABLE 5

BIAcore analysis of 1-7F9 mAb binding to immobilized KIR2DL1 and KIR2DL3. $K_D$: Dissociation constant.

| Protein | $K_D$ ($10^{-9}$ M) |
|---|---|
| KIR2DL1 | 0.43 |
| KIR2DL3 | 0.025 |

Example 9

Epitope Mapping of 1-7F9 onto KIR2DL1

Epitope mapping of a given monoclonal antibody onto a given antigen can be obtained by in silico methods when suitable X-ray structures/homology models exist of both the antibody and the antigen by performing protein-protein docking.

A homology-model of an antibody can be obtained by aligning the sequence of the Light and Heavy Chain, respectively, with a selection of antibodies for which a 3D structure exists. The length of the 6 Complementarity Determining Regions (CDRs) can be calculated and the best template selected from antibodies with the same CDR lengths. Using standard techniques a homology model can be build from the selected template.

In the protein-protein docking approach, recently reviewed (Schneidman-Duhovny et al., Curr Med Chem 2004; 11:91-107), the two surfaces are represented by features on surfaces. Features include hydrogen bonding capabilities, charges and hydrophobicity. In a grid based method, space is divided into cubes and each cube is given a value according to its position relative to the surface (interior, surface, exterior) and assigned the relevant feature set. Brute force matching of the surfaces by a scoring function can now be employed by searching the entire 3 translational and 3 rotational degrees of freedom. Translations are handled by Fast Fourier Transform and rotation is treated as individual calculations within a standard discretization of rotational space. From the top scoring complexes the results can be filtered and scored, by a range of methods, e.g., shape complementarity, Van der Waals interactions, hydrophobicity, electrostatics, desolvation, hydrogen bonding, atomic contact energy, residue-residue pairing statistics and hydrophilic group pairing. The top-scoring complexes can be evaluated in detail and interacting residues and thereby the epitope can be identified.

Methods and Analysis

Residue and domain nomenclature for the KIRs were according to Fan et al. (Nature 1997; 389:96-100), so that Domain1 comprised residues 6-101 and Domain 2 comprised amino acids residues 105-200).

A homology-model of 1-7F9 was constructed using 1OM3 as a template. The 1OM3 structure, generated by Calarese et al (Science 2003; 300:2065, et seq.), was retrieved from the PDB (Protein Data Bank, at World Wide Web (WWW) address rcsb.org/pdb/; 1OM3 VL sequence: SEQ ID NO:34; 1OM3 VH sequence: SEQ ID NO:35). Kabat Numbering and CDR assignment were used. The overall alignment was good and the CDR lengths were identical, so the homology model would be accurate enough to be used in a protein-protein docking experiment.

From the protein-protein docking of the 1-7F9 antibody homology model onto the KIR2DL1 structure, 1 NKR.pdb 2000 solutions were obtained. They were filtered for their closeness to D183 (atoms <6 Å from CD) and R131 (atoms <12 Å from CZ) and 133 resulting solutions were analyzed in detail.

The highest scoring complex formed was analyzed and a possible interaction between R131 (KIR) and D100C (Heavy chain) was identified and restrained. A new rotamer for F181 was selected and the energy was minimized. This model predicted that the antibody interacted with the following residues on KIR2DL1 (SEQ ID NO:23): S20 (Hyd, CB) (HydAcceptor, OG), E21 (Hyd, CB, CG), M44 (Hyd, SD, CE), F45 (Hyd, CD1, CD1, CZ, CE2), R68 (HydDonor, NH2), T70 (Hyd, CB, CG2), Q71 (Hyd, CG), L104 (Hyd, CB, CG, CD1, CD2), Y105 (Hyd, CG, CD2, CE2), R131 (ion, NH2) (HydDonor, NH2), S133 (Hyd, CA, CB) (HydDonor/Acceptor, OG), Y134 (Hyd, CD1, CE1), F181 (Hyd, CB, CG, CD1, CD2, CE1, CE2, CZ), and D183 (Hyd, CB).

Example 10

Biacore Competitive Binding Analysis of Murine and Human Anti-KIR Antibodies

Competitive binding of 1-7F9, Pan2D (NKVSF1), and DF200 was evaluated according to the same method described in Example 5.

Results are shown in Tables 6 and 7, where the antibodies designated "first antibody" are listed on vertical column and the 'second antibody' are listed on the horizontal column. For each antibody combination tested, the percentage inhibition of second antibody binding is listed. Where the percentages of inhibition for a certain antibody pair were above 40%, regardless of which antibody was used as first antibody, the antibodies were considered competitive. Table 6 shows binding on a KIR2DL1 chip, and Table 7 shows binding of antibodies to a KIR2DL3 chip.

Briefly, for KIR2DL1 binding, the results show that DF200 and Pan2D are competitive, whereas 1-7F9 is not competitive with either one of DF200 or Pan2D. For KIR2DL3 binding, DF200 and Pan2D were competitive, whereas 1-7F9 was not competitive with Pan2D, but was competitive with DF200.

TABLE 6

KIR2DL1 competitive binding between first and second antibodies.

| First antibody | Second antibody | | |
|---|---|---|---|
| (below) | 1-7F9 | Pan2D | DF200 |
| 1-7F9 | 98% | 4% | 15% |
| Pan2D | 17% | 92% | 90% |
| DF200 | 17% | 85% | 80% |

TABLE 7

KIR2DL1 competitive binding between first and second antibodies.

| First antibody | Second antibody | | |
|---|---|---|---|
| (below) | | | |
| First mAb | 1-7F9 | Pan2D | DF200 |
| 1-7F9 | 95% | 4% | 60% |
| Pan2D | 0% | 95% | 95% |
| DF200 | 80% | 50% | 85% |

Example 11

Crystal Structure of KIR2DL1 in Complex with HuKIR1-7F9-Fab'

Figure 19:
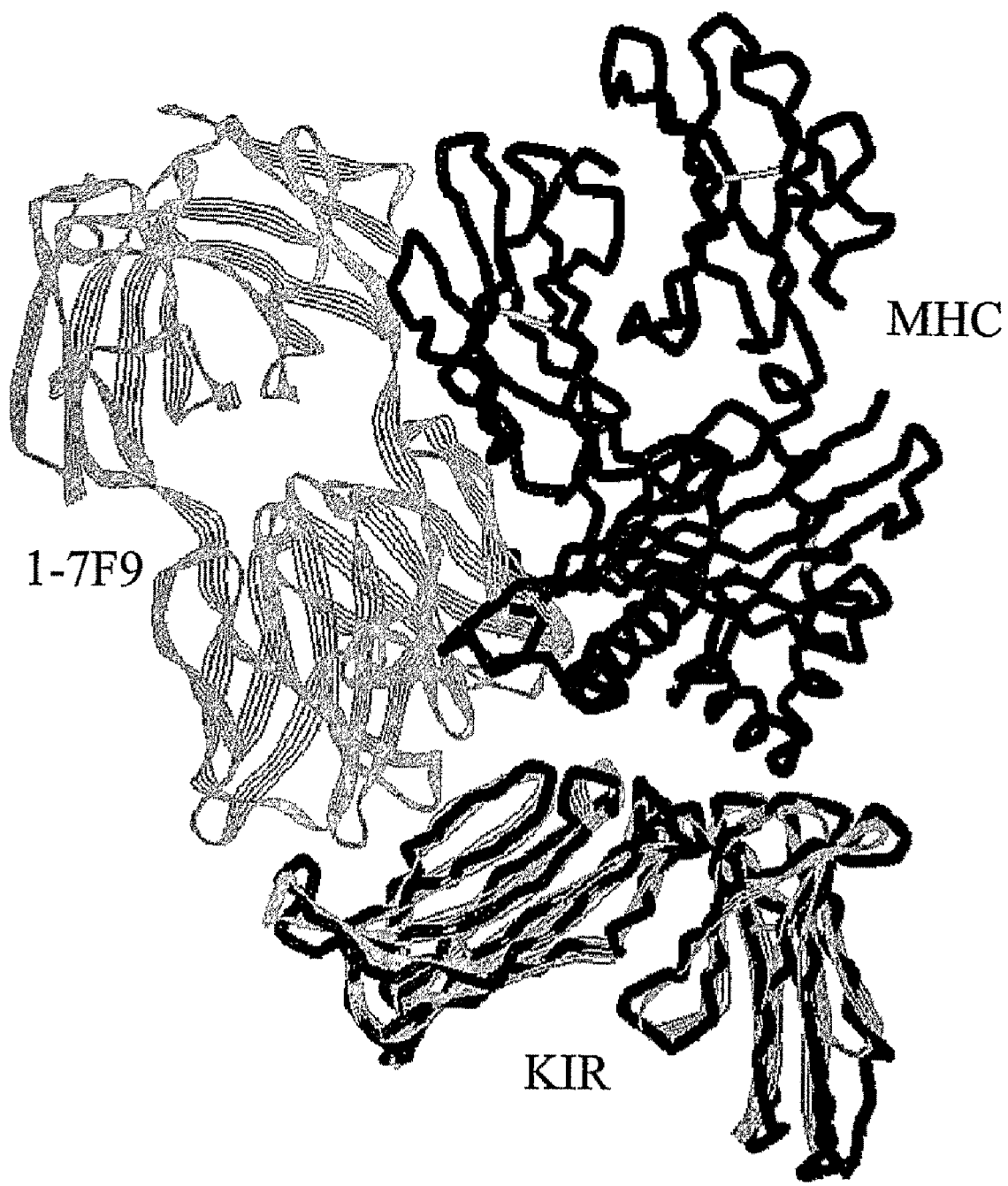
FIG. 19 depicts a superposition of two crystal complex structures; the KIR2DL1/1-7F9 Fab' and the KIR2DL1/MHC class I, PDB-code 1IM9 (Fan et al., Nat. Immunol. 2001; 2:452-460), using the $C_\alpha$-atoms of the common KIR molecule (labeled 'KIR') as template. KIR2DL1/1-7F9 Fab' is indicated in grey line ribbon style while KIR2DL1/MHC class I in a dark tube style. 1-7F9 Fab' is labeled '1-7F9' while MHC class I is labeled 'MHC'. An overlap between the MHC and the Fab' is seen in the superposition, demonstrating the ability of 1-7F9 Fab' to obstruct MHC class I binding to the KIR2DL1 receptor. See Example 11.

The crystal structure of KIR2DL1 in complex with the Fab' fragment of 1-7F9 was solved and refined to 2.35 Å resolution with X-ray crystallography. The results confirmed that the antibody, when bound to KIR2DL1, will be able to block binding to an MHC Class I molecule (FIG. 19).

Materials and Methods

Extracellular KIR2DL1 (amino acid 1-223 of SEQ ID NO:23, with residue 16 being arginine (R) and residue 114 being leucine (L), and including an additional N-terminal methionine (M) residue) and HuKIR1-7F9 Fab' (with the light chain sequence of SEQ ID NO:36 and heavy chain sequence of residues 1-221 of SEQ ID NO:37) were mixed, with a slight excess of KIR2DL1, and the complex was purified on a gel-filtration column. The complex was then concentrated to about 13.5 mg/ml. Crystals were grown with the hanging drop-technique in 10% PEG6000 and 500 mM citrate buffer with a pH of 4.2. Crystals were flash frozen in liquid $N_2$ and crystallographic data to 2.35 Å resolution were collected at 100 K using the beam-line BL711I, MAX-lab, Lund, Sweden. Data were integrated by the XDS program (Kabsch, J. Appl. Crystallogr. 1993; 26:795-800). For structure determination molecular replacement, using the MOLREP program of the CCP4 suite (Bailey, Acta Crystallogr. Sect. D-Biol. Crystallogr. 1994; 50:760-763) and the PDB-deposited structures 1RZJ (the Fab part1) and 1NKR (KIR), were used. Phase improvements were made with the ARP/WARP program (Lamzin and Wilson, Acta Crystallogr. Sect. D-Biol. Crystallogr. 1993; 49:129-147) and manual modifications to the X-ray derived structure model were made with the QUANTA program (available from Accelrys Inc., San Diego, Calif., USA). Refinement was carried out in the REFMAC5 computer program of the CCP4 suite. Water molecules were added by the ARP/WARP program. The model comprised residues 6-114 and 124-200 of KIR2DL1, 1-212 of the 1-7F9 light chain and 1-136 together with 143-224 of the 1-7F9 heavy chain. In addition, 330 water molecules were placed. R- and R-free for the model were 0.191 and 0.253, respectively.

Results

The contacts were identified by the CONTACT computer program of the CCP4 suite using a cut-off distance of 4.0 Å between the Fab' and KIR2DL1 molecules. The resulting KIR2DL1 epitope for human 1-7F9 was found to comprise the following residues of KIR2DL1 (SEQ ID NO:23): L38, R41, M44, F45, N46, D47, T48, L49, R50, I52, F64, D72, Y80, P87, and Y88 (Tables 8 and 9). Residues of 1-7F9 involved in interactions with KIR2DL1 included S28, V29, S30, Y32, S92, N93, and W94 of the 1-7F9 variable light (VL) chain (SEQ ID NO:15, Table 8), and T28, F29, S30, F31, I54, F55, E74, S77, G102, S103, Y105, Y106, D107, and Y108 of the variable heavy (VH) chain (SEQ ID NO:17). The KIR2DL1 epitope, and the residues involved in hydrogen-binding, are also indicated in the amino-acid sequence of KIR2DL1 in FIG. 20. The isotropic displacement factors (also called "temperature factors" or "B-values") obtained from the coordinate refinement showed relatively lower values for the N-terminal domain of KIR2DL1 and the variable domains of the 1-7F9 antibody Fab' fragment, all domains directly involved in the intermolecular binding. This showed that the binding forces between the two molecules in the complex of the crystal were strong and stable, also supporting that the crystal structure depicted a stable KIR2DL1/1-7F9 Fab' complex.

The 1-7F9 Fab' molecule bound to the KIR2DL1 molecule on one side of the C'CFGA' β-sheet of domain D1 but, in addition, touched also one E β-strand residue side-chain of the same domain. Connections to loop residues of the D1 domain are also important for binding (for topology naming conventions, see Fan et al., Nature 1997; 389:96-100). More specifically, connections are made to the following topological parts of KIR2DL1; β-strand C (amino acids L38 and R41), the loop between β-strands C and C', L2 (M44, F45 and N46), β-strand C' (D47, T48, L49, R50 and I52), β-strand E (F64), the loop between the E and F β-strands, L3 (D72), β-stand F (Y80) and the loop between the F and G β-strands (P87 and Y88).

While the HLA-Cw4 molecule binds both to the D1 and D2 domain of the KIR2DL1 molecule (Fan et al. Nat. Immunol. 2001; 2: 452-460) the 1-7F9 antibody binds to the KIR2DL1 D1 domain only. There is, however, a spatial overlap between a bound 1-7F9 and a bound HLA-Cw4 molecule, large enough for the 1-7F9 antibody to successfully displace HLA-Cw4. Using the published structure of KIR2DL1 in complex with HLA-Cw4 (PDB accession code 1IM9) contact residues between KIR2DL1 and HLA-Cw4 can be calculated with the CONTACT program. In a calculation using a distance cut-off of 4.0 Å it can be seen that three KIR2DL1 residues involved in contacts with HLA-Cw4 residues are common to contact residues in the 1-7F9/KIR2DL1 complex (Table 8 and 9). Those three KIR2DL1 residues are M44, F45 and D72.

Without being limited to any specific theory, the crystallographic results also indicated that 1-7F9 does not bind the activating NK receptor KIR2DS4 because of amino acids N47 and V72 in the extracellular portion of the KIR2DS4 sequence (SEQ ID NO:38).

TABLE 8

KIR2DL1 - 1-7F9 Fab' VL chain interactions. A cut-off of 4.0 Å was used. The contacts were identified by the CONTACT computer program of the CCP4 suite.

| KIR2DL1 Atoms | | | 1-7F9 Fab' VL Atoms | | | Distance (Å) |
|---|---|---|---|---|---|---|
| Arg | 41A | NH2 | Tyr | 32L | OH | 2.73*** |
| Met | 44A | O | Asn | 93L | CG | 3.65 |
| | | | Asn | 93L | OD1 | 3.54* |
| | | | Asn | 93L | ND2 | 2.96*** |
| Phe | 45A | CA | Asn | 93L | OD1 | 3.50 |
| Phe | 45A | CB | Tyr | 32L | CE1 | 3.59 |
| Phe | 45A | CG | Tyr | 32L | CE1 | 3.93 |
| Phe | 45A | CE1 | Ser | 30L | CB | 3.82 |
| Phe | 45A | CZ | Ser | 28L | O | 3.77 |
| | | | Ser | 30L | CB | 3.74 |
| | | | Ser | 28L | OG | 3.89 |
| | | | Ser | 30L | N | 3.78 |
| Phe | 45A | CE2 | Ser | 28L | O | 3.76 |
| | | | Val | 29L | O | 3.98 |
| | | | Val | 29L | CA | 3.94 |
| | | | Ser | 30L | CB | 3.87 |
| | | | Val | 29L | C | 3.72 |
| | | | Ser | 30L | N | 3.89 |
| Phe | 45A | CD2 | Asn | 93L | ND2 | 3.75 |
| | | | Ser | 92L | CB | 3.85 |
| Phe | 45A | C | Asn | 93L | OD1 | 3.70 |
| Asn | 46A | N | Asn | 93L | OD1 | 2.92*** |
| Asn | 46A | CA | Asn | 93L | OD1 | 3.82 |
| Asn | 46A | CB | Asn | 93L | OD1 | 3.52 |
| | | | Trp | 94L | CH2 | 3.86 |
| | | | Trp | 94L | CZ2 | 3.52 |
| Asn | 46A | CG | Asn | 93L | OD1 | 3.31 |
| | | | Trp | 94L | CH2 | 3.41 |
| | | | Trp | 94L | CZ2 | 3.65 |
| Asn | 46A | OD1 | Trp | 94L | CH2 | 3.85 |
| Asn | 46A | ND2 | Asn | 93L | CB | 3.99 |
| | | | Asn | 93L | CG | 3.48 |
| | | | Asn | 93L | OD1 | 2.56*** |
| | | | Trp | 94L | CZ3 | 3.52 |
| | | | Trp | 94L | CH2 | 3.25 |
| | | | Trp | 94L | CZ2 | 3.76 |
| Asp | 47A | CB | Tyr | 32L | OH | 3.63 |
| Asp | 47A | CG | Tyr | 32L | OH | 3.74 |
| | | | Tyr | 32L | CE2 | 3.79 |
| Asp | 47A | OD2 | Tyr | 32L | CZ | 3.88 |
| | | | Tyr | 32L | OH | 3.34* |
| | | | Tyr | 32L | CE2 | 3.54 |
| Asp | 72A | CB | Ser | 30L | OG | 3.87 |
| Asp | 72A | CG | Ser | 30L | OG | 3.62 |
| Asp | 72A | OD2 | Ser | 30L | CB | 3.58 |
| | | | Ser | 30L | OG | 2.93*** |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

TABLE 9

KIR2DL1 - 1-7F9 Fab' VH chain interactions. A cut-off of 4.0 Å was used. The contacts were identified by the CONTACT computer program of the CCP4 suite.

| KIR2DL1 Atoms | | | 1-7F9 Fab' VH Atoms | | | Distance (Å) |
|---|---|---|---|---|---|---|
| Leu | 38A | CD1 | Ile | 54H | CD1 | 3.61 |
|  |  |  | Phe | 31H | CB | 3.64 |
| Leu | 38A | CD2 | Phe | 31H | CG | 3.70 |
|  |  |  | Phe | 31H | CD2 | 3.74 |
| Asp | 47A | CG | Ser | 103H | N | 3.73 |
|  |  |  | Ser | 103H | OG | 3.63 |
| Asp | 47A | OD1 | Gly | 102H | N | 3.99* |
|  |  |  | Gly | 102H | CA | 3.40 |
|  |  |  | Gly | 102H | C | 3.75 |
|  |  |  | Ser | 103H | N | 3.09*** |
|  |  |  | Ser | 103H | OG | 3.77* |
| Asp | 47A | OD2 | Ser | 103H | N | 3.73* |
|  |  |  | Ser | 103H | CB | 3.36 |
|  |  |  | Ser | 103H | OG | 2.77*** |
| Thr | 48A | C | Tyr | 108H | OH | 3.74 |
| Thr | 48A | O | Tyr | 108H | CZ | 3.68 |
|  |  |  | Tyr | 108H | OH | 2.90*** |
|  |  |  | Tyr | 108H | CE2 | 3.65 |
| Leu | 49A | CA | Tyr | 105H | O | 3.28 |
| Leu | 49A | CB | Tyr | 105H | O | 3.62 |
| Leu | 49A | CD2 | Tyr | 105H | O | 3.67 |
|  |  |  | Tyr | 105H | CB | 3.71 |
|  |  |  | Tyr | 105H | CD1 | 3.76 |
|  |  |  | Ser | 103H | OG | 3.91 |
| Leu | 49A | C | Tyr | 105H | O | 3.59 |
| Arg | 50A | N | Tyr | 105H | C | 3.80 |
|  |  |  | Tyr | 105H | O | 2.94*** |
|  |  |  | Tyr | 106H | N | 3.87* |
|  |  |  | Tyr | 108H | CE2 | 3.81 |
| Arg | 50A | CA | Tyr | 105H | O | 3.97 |
| Arg | 50A | CB | Tyr | 106H | O | 3.88 |
|  |  |  | Tyr | 108H | CE2 | 3.80 |
| Arg | 50A | CG | Phe | 31H | CZ | 3.65 |
|  |  |  | Phe | 31H | CE2 | 3.90 |
|  |  |  | Tyr | 106H | O | 3.99 |
| Arg | 50A | CD | Phe | 31H | CZ | 3.32 |
|  |  |  | Phe | 31H | CE2 | 3.63 |
|  |  |  | Tyr | 106H | O | 3.71 |
| Arg | 50A | NE | Tyr | 106H | O | 2.88*** |
|  |  |  | Asp | 107H | C | 3.94 |
|  |  |  | Asp | 107H | O | 3.58* |
| Arg | 50A | CZ | Tyr | 106H | O | 3.70 |
|  |  |  | Asp | 107H | O | 3.74 |
| Arg | 50A | NH2 | Tyr | 106H | O | 3.61* |
|  |  |  | Asp | 107H | CB | 3.56 |
|  |  |  | Asp | 107H | O | 3.86* |
| Arg | 50A | C | Tyr | 106H | N | 3.86 |
| Arg | 50A | O | Tyr | 106H | O | 3.56* |
|  |  |  | Tyr | 105H | C | 3.68 |
|  |  |  | Tyr | 105H | O | 3.72* |
|  |  |  | Tyr | 106H | N | 2.86*** |
|  |  |  | Tyr | 106H | CA | 3.67 |
|  |  |  | Tyr | 106H | CB | 3.47 |
| Ile | 52A | CD1 | Tyr | 106H | CD1 | 3.93 |
|  |  |  | Tyr | 106H | CE1 | 3.68 |
| Phe | 64A | CD2 | Tyr | 105H | CE1 | 3.86 |
| Tyr | 80A | CZ | Phe | 55H | CE2 | 3.90 |
| Tyr | 80A | OH | Phe | 55H | CE2 | 3.87 |
| Pro | 87A | CB | Thr | 28H | OG1 | 3.46 |
| Pro | 87A | CG | Thr | 28H | OG1 | 3.66 |
| Pro | 87A | O | Ser | 30H | CA | 3.87 |
|  |  |  | Ser | 30H | C | 3.88 |
| Tyr | 88A | CB | Glu | 74H | CD | 3.39 |
|  |  |  | Glu | 74H | OE1 | 3.38 |
|  |  |  | Glu | 74H | OE2 | 3.40 |
| Tyr | 88A | CG | Glu | 74H | CG | 3.65 |
|  |  |  | Glu | 74H | CD | 3.37 |
|  |  |  | Glu | 74H | OE1 | 3.71 |
|  |  |  | Glu | 74H | OE2 | 3.55 |
| Tyr | 88A | CD1 | Glu | 74H | CB | 3.85 |
|  |  |  | Glu | 74H | CG | 3.72 |
|  |  |  | Glu | 74H | CD | 3.82 |
|  |  |  | Glu | 74H | OE1 | 3.97 |
| Tyr | 88A | CE1 | Glu | 74H | CB | 3.93 |
|  |  |  | Glu | 74H | CG | 3.91 |
|  |  |  | Glu | 74H | O | 3.84 |
|  |  |  | Ser | 77H | OG | 3.68 |
|  |  |  | Thr | 28H | CB | 3.97 |
| Tyr | 88A | CZ | Ser | 77H | OG | 3.51 |
|  |  |  | Ser | 30H | N | 3.87 |
|  |  |  | Thr | 28H | CB | 3.71 |
|  |  |  | Phe | 29H | N | 3.86 |
| Tyr | 88A | OH | Ser | 77H | CA | 3.73 |
|  |  |  | Ser | 77H | CB | 3.35 |
|  |  |  | Ser | 77H | OG | 2.49*** |
|  |  |  | Thr | 28H | CA | 3.88 |
|  |  |  | Thr | 28H | CB | 3.34 |
|  |  |  | Thr | 28H | C | 3.96 |
|  |  |  | Phe | 29H | N | 3.07*** |
|  |  |  | Phe | 29H | CA | 3.86 |
|  |  |  | Phe | 29H | CB | 3.67 |
|  |  |  | Phe | 29H | CD2 | 3.83 |
| Tyr | 88A | CE2 | Ser | 30H | N | 3.32 |
|  |  |  | Ser | 30H | O | 3.82 |
|  |  |  | Phe | 29H | C | 3.92 |
|  |  |  | Phe | 29H | CB | 3.89 |
| Tyr | 88A | CD2 | Glu | 74H | CG | 3.81 |
|  |  |  | Glu | 74H | CD | 3.77 |
|  |  |  | Glu | 74H | OE2 | 3.64 |
|  |  |  | Ser | 30H | N | 3.91 |
|  |  |  | Ser | 30H | O | 3.58 |
|  |  |  | Pro | 53H | CB | 3.83 |
| Tyr | 88A | C | Ile | 54H | CG2 | 3.93 |
| Tyr | 88A | O | Ile | 54H | CG2 | 3.75 |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

Example 12

Physical Stability of 1-7F9

The biophysical properties and stability of human antibody 1-7F9 were studied. The folding and secondary structure of the protein was studied by circular dichroism (CD) and the oligomerization and aggregation by dynamic light scattering (DLS). In order to mimic storage conditions for two years at 5° C. the protein was subjected to incubation at 37° C. with shaking for 14 days.

Materials and Methods

Sample preparation. 2 mg/ml 1-7F9 was prepared in (a) 50 mM Na-Phosphate, 0.001% Polysorbate 80 (Sigma, P8074), pH 7.0; (b) 50 mM Na-Phosphate, 0.001% Polysorbate 80, pH 7.0, 0.5 mM Sucrose; (c) 50 mM Citrate, 0.001% Polysorbate 80, pH 3.0; and d) 50 mM Tris, 0.001% Polysorbate 80, pH 8.5.

Circular dichroism (CD). CD measurements were performed at 25° C. with a protein concentration of 2.0 mg/ml on a Chirascan circular dichroism spectrometer (Applied Photophysics) equipped with a peltier element for temperature control. 1-7F9 samples were in cylindrical quartz cells with 0.1 mm path length. Buffer scans were recorded and subtracted for each sample spectra.

Dynamic light scattering (DLS). DLS was performed at 25° C. with a protein concentration of 2.0 mg/ml using a Dynapro 99 temperature controlled DLS instrument (Protein Solutions Inc.). Data analysis was performed using the Dynamics software supplied with the instrument.

Results

Whereas the molecular size did not change for the samples at pH 7.0 after 14 days incubation as evaluated by DLS, both the samples formulated at pH 3.0 and pH 8.5 aggregated heavily during a 14 day period.

The CD measurements showed characteristics of an all beta structure and revealed that the samples formulated at pH 7.0 maintained their secondary structure throughout the accelerated study, although there was a slight drop in the signal for the sample containing only Polysorbate 80 as excipient. This might be due to a weak precipitation of the sample since the overall form of the spectra is unchanged. The sample containing sucrose showed no such decrease over time. The CD measurements of the samples formulated at pH 3.0 and 8.5 showed a strong change in spectral characteristics over time, probably as a result of unfolding or other conformational changes, which could lead to non-functional 1-7F9 protein. The changes were observed immediately and were most significant at pH 3.0.

Overall, 1-7F9 maintained its physical properties and remained stable under stressed conditions (37° C. with shaking) at pH 7.0 with Polysorbate 80 and Sucrose as excipients.

Example 13

Affinity Determination (Monovalent Binding) of 1-7F9 and 1-4F1

The affinities of 1-7F9 and 1-4F1 in monovalent binding to KIR2DL1 and KIR2DL3 antigen, (as opposed to the bivalent binding affinity determinations in Examples 3 and 8), were determined by surface plasmon resonance technology, using a Biacore 3000.

Briefly, an anti-human IgG (Dako RAHIgG, # 0423) was used together with an HBS-EP buffer at a flow rate of 20 µL/min. Purified antibodies were diluted to 10 µg/mL. For each antibody, KIR2DL1 or KIR2DL3 and buffer was injected. The antigens were tested at concentrations of 2000, 500, 200, 50 og 20 nM. Flowrate was maintained at 20 µL/min. Regeneration of the surface was accomplished by a single 30 s injection of Glycine-HCl pH 1.8.

The results are displayed in Table 10. For the binding of 1-4F1 to KIR2DL1, there was a significant shift in baseline. Without being limited to any specific theory, this might represent a buffer effect caused by the matrix, or the binding reaction actually involving 2 steps, e.g., because of a conformational change of the antigen.

TABLE 10

Monovalent binding affinity of 1-7F9 and 1-4F1 to KIR2DL1 and KIR2DL3.

|  | $k_a$ (1/Ms) | $k_d$ (1/s) | $K_D$ (M) | Chi2 |
|---|---|---|---|---|
| 1-4F1/2DL1 | 8.33E+03 | 5.09E−15 | 6.11E−19 | 1.24 |
| 1-4F1/2DL1 *) | 2.68E+04 | 0.0132 | 4.95E−07 | 9.1 |
| 1-4F1/2DL3 | 4.16E+05 | 2.94E−03 | 7.05E−09 | 0.398 |
| 1-7F9/2DL1 | 1.51E+05 | 1.56E−03 | 1.03E−08 | 4.02 |
| 1-7F9/2DL3 | 1.51E+05 | 5.20E−04 | 3.45E−09 | 1.55 |

*) indicates fit with RI (response of matrix) fitted globally.

EXEMPLARY ASPECTS OF THE INVENTION

1. An antibody comprising a light chain variable region comprising an amino acid sequence at least 50% identical to SEQ ID NO:15 or SEQ ID NO:39, and/or a heavy chain variable region comprising an amino acid sequence at least 50% identical to SEQ ID NO:17 or SEQ ID NO:41.

2. An antibody comprising a light chain variable region comprising an amino acid sequence at least 80% identical to SEQ ID NO:15 or SEQ ID NO:39, and/or a heavy chain variable region comprising an amino acid sequence at least 80% identical to SEQ ID NO:17 or SEQ ID NO:41.

3. An antibody comprising a light chain variable region comprising an amino acid sequence at least 90% identical to SEQ ID NO:15 or SEQ ID NO:39, and/or a heavy chain variable region comprising an amino acid sequence at least 90% identical to SEQ ID NO:17 or SEQ ID NO:41.

4. An antibody comprising a light chain variable region comprising an amino acid sequence at least 95% identical to SEQ ID NO:15 or SEQ ID NO:39, and/or a heavy chain variable region comprising an amino acid sequence at least 95% identical to SEQ ID NO:17 or SEQ ID NO:41.

5. An antibody comprising a light chain variable region comprising an amino acid sequence at least 98% identical to SEQ ID NO:15 or SEQ ID NO:39, and/or a heavy chain variable region comprising an amino acid sequence at least 98% identical to SEQ ID NO:17 or SEQ ID NO:41.

6. The antibody of any of the preceding aspects, wherein the light chain variable region comprises at least one conservative amino acid substitution, each amino acid substitution being conservative as compared to the amino acid at the corresponding position in SEQ ID NO:15 or SEQ ID NO:39.

7. The antibody of any of the preceding aspects, wherein the heavy chain variable region comprises at least one conservative amino acid substitution, each amino acid substitution being conservative as compared to the amino acid at the corresponding position in SEQ ID NO:17 or SEQ ID NO:41.

8. The antibody of any of the preceding aspects, comprising at least one of
   (a) a light chain CDR1 amino acid sequence at least 90% identical to residues 24-34 of SEQ ID NO:15;
   (b) a light chain CDR2 amino acid sequence at least 90% identical to residues 50-56 of SEQ ID NO:15;
   (c) a light chain CDR3 amino acid sequence at least 90% identical to residues 89-97 of SEQ ID NO:15;
   (d) a heavy chain CDR1 amino acid sequence at least 90% identical to residues 31-35 of SEQ ID NO:17;
   (e) a heavy chain CDR2 amino acid sequence at least 90% identical to residues 50-65 of SEQ ID NO:17; and
   (f) a heavy chain CDR3 amino acid sequence at least 90% identical to residues 99-112 of SEQ ID NO:17.

9. The antibody of any of the preceding aspects, comprising at least one of
   (a) a light chain CDR1 amino acid sequence corresponding to residues 24-34 of SEQ ID NO:15;
   (b) a light chain CDR2 amino acid sequence corresponding to residues 50-56 of SEQ ID NO:15;
   (c) a light chain CDR3 amino acid sequence corresponding to residues 89-97 of SEQ ID NO:15.
   (d) a heavy chain CDR1 amino acid sequence corresponding to residues 31-35 of SEQ ID NO:17;
   (e) a heavy chain CDR2 amino acid sequence corresponding to residues 50-65 of SEQ ID NO:17; and
   (f) a heavy chain CDR3 amino acid sequence corresponding to residues 99-112 of SEQ ID NO:17.

10. The antibody of any of the preceding aspects, comprising at least one of
   (a) a light chain CDR1 amino acid sequence consisting essentially of residues 24-34 of SEQ ID NO:15;
   (b) a light chain CDR2 amino acid sequence consisting essentially of residues 50-56 of SEQ ID NO:15;

(c) a light chain CDR3 amino acid sequence consisting essentially of residues 89-97 of SEQ ID NO:15.
(d) a heavy chain CDR1 amino acid sequence consisting essentially of residues 31-35 of SEQ ID NO:17;
(e) a heavy chain CDR2 amino acid sequence consisting essentially of residues 50-65 of SEQ ID NO:17; and
(f) a heavy chain CDR3 amino acid sequence consisting essentially of residues 99-112 of SEQ ID NO:17.

11. The antibody of any of aspects 8-10, comprising at least 2 of (a) to (f).

12. The antibody of any of aspects 8-10, comprising at least 3 of (a) to (f).

13. The antibody of any of aspects 8-10, comprising at least 4 of (a) to (f).

14. The antibody of any of aspects 8-10, comprising at least 5 of (a) to (f).

15. The antibody of any of aspects 8-10, comprising all of (a) to (f).

16. The antibody of any of the preceding aspects, comprising a light chain variable region comprising the amino acid sequence of SEQ ID NO:15, and a heavy chain variable region comprising the amino acid sequence of SEQ ID NO:17.

17. The antibody of any of aspects 1-7, comprising at least one of
(g) a light chain CDR1 amino acid sequence at least 90% identical to residues 24-34 of SEQ ID NO:39;
(h) a light chain CDR2 amino acid sequence at least 90% identical to residues 50-56 of SEQ ID NO:39;
(i) a light chain CDR3 amino acid sequence at least 90% identical to residues 89-97 of SEQ ID NO:39;
(j) a heavy chain CDR1 amino acid sequence at least 90% identical to residues 31-35 of SEQ ID NO:41;
(k) a heavy chain CDR2 amino acid sequence at least 90% identical to residues 50-66 of SEQ ID NO:41; and
(l) a heavy chain CDR3 amino acid sequence at least 90% identical to residues 99-113 of SEQ ID NO:41.

18. The antibody of any aspects 1-7 and 17, comprising at least one of
(g) a light chain CDR1 amino acid sequence corresponding to residues 24-34 of SEQ ID NO:39;
(h) a light chain CDR2 amino acid sequence corresponding to residues 50-56 of SEQ ID NO:39;
(i) a light chain CDR3 amino acid sequence corresponding to residues 89-97 of SEQ ID NO:39;
(j) a heavy chain CDR1 amino acid sequence corresponding to residues 31-35 of SEQ ID NO:41;
(k) a heavy chain CDR2 amino acid sequence corresponding to residues 50-66 of SEQ ID NO:41; and
(l) a heavy chain CDR3 amino acid sequence corresponding to residues 99-113 of SEQ ID NO:41.

19. The antibody of any aspects 1-7 and 17-18, comprising at least one of
(g) a light chain CDR1 amino acid sequence consisting essentially of residues 24-34 of SEQ ID NO:39;
(h) a light chain CDR2 amino acid sequence consisting essentially of residues 50-56 of SEQ ID NO:39;
(i) a light chain CDR3 amino acid sequence consisting essentially of residues 89-97 of SEQ ID NO:39;
(j) a heavy chain CDR1 amino acid sequence consisting essentially of residues 31-35 of SEQ ID NO:41;
(k) a heavy chain CDR2 amino acid sequence consisting essentially of residues 50-66 of SEQ ID NO:41; and
(l) a heavy chain CDR3 amino acid sequence consisting essentially of residues 99-113 of SEQ ID NO:41.

20. The antibody of any of aspects 17-19, comprising at least 2 of (a) to (f).

21. The antibody of any of aspects 17-19, comprising at least 3 of (a) to (f).

22. The antibody of any of aspects 17-19, comprising at least 4 of (a) to (f).

23. The antibody of any of aspects 17-19, comprising at least 5 of (a) to (f).

24. The antibody of any of aspects 17-19, comprising all of (a) to (f).

25. The antibody of any of aspects 1-7 and 17-24, comprising a light chain variable region comprising the amino acid sequence of SEQ ID NO:39, and a heavy chain variable region comprising the amino acid sequence of SEQ ID NO:41.

26. The antibody of any of the preceding aspects, which antibody does not bind at least one of KIR2DS4 and KIR2DS3.

27. The antibody of any aspects 1-15 and 26, which antibody blocks KIR2DL1 and KIR2DL2/3 binding to an HLA-C class I molecule.

28. The antibody of any aspects 1-15 and 26-27, which potentiates the lytic activity of an NK cell against a human target cell expressing an HLA-C class I molecule.

29. The antibody of any of aspects 1-15 and 26-28 which antibody is more efficient than DF200 in potentiating the lytic activity of an NK cell against a human target cell expressing an HLA-C Class I molecule.

30. The antibody of any of aspects 1-15 and 26-28, which antibody is more efficient than NKVSF1 (Pan2D) in potentiating the lytic activity of an NK cell against a human target cell expressing an HLA-C Class I molecule.

31. The antibody of any of aspects 1-15 and 26-28, which antibody is more efficient than EB6 in potentiating the lytic activity of an NK cell against a human target cell expressing an HLA-C Class I molecule 32. The antibody of any of the preceding aspects, which is a human or humanized antibody.

33. The antibody of any of the preceding aspects, which is an IgG1, IgG2, IgG3, or IgG4 antibody.

34. The antibody of any of the preceding aspects, which is a human IgG4 antibody.

35. The antibody of any of aspects 1-34, which is a human IgG2 antibody.

36. A human IgG4 antibody comprising a light chain variable region comprising the amino acid sequence of SEQ ID NO:15, and a heavy chain variable region comprising the amino acid sequence of SEQ ID NO:17.

37. A human IgG2 antibody comprising a light chain variable region comprising the amino acid sequence of SEQ ID NO:39, and a heavy chain variable region comprising the amino acid sequence of SEQ ID NO:41.

38. An antibody that competes with 1-7F9 in the binding to KIR2DL1 or KIR2DL2/3, wherein the antibody is not 1-4F1, DF200, gl83, A210, A803(g), or EB6.

39. An antibody that competes with 1-4F1 in the binding to KIR2DL1 or KIR2DL2/3, wherein the antibody is not 1-7F9, DF200, gl183, A210, A803(g), or EB6.

40. The antibody of aspect 38, wherein the antibody is not 1-4F1.

41. The antibody of aspects 39, wherein the antibody is not 1-7F9

42. The antibody of any of aspects 38-39, wherein the antibody is not DF200.

43. The antibody of any of aspects 38-39, wherein the antibody is not gl183.

44. The antibody of any of aspects 38-39, wherein the antibody is not EB6.

45. The antibody of any of the preceding aspects, which has a $K_d$ to KIR2DL1 of no more than about 20 nM.
46. The antibody of any of the preceding aspects, which has a $K_d$ to KIR2DL1 of no more than 10.9 nM.
47. The antibody of any of the preceding aspects, which has a $K_d$ to KIR2DL1 of no more than 0.45 nM.
48. The antibody of any of the preceding aspects, which has a $K_d$ to KIR2DL3 of no more than about 20 nM.
49. The antibody of any of the preceding aspects, which has a $K_d$ to KIR2DL3 of no more than 2.0 nM.
50. The antibody of any of the preceding aspects, which has a $K_d$ to KIR2DL3 of no more than 0.025 nM.
51. The antibody of any of the preceding aspects, which is human.
52. A human or humanized antibody that competes with 1-7F9 in the binding to KIR2DL1.
53. A human or humanized antibody that competes with 1-4F1 in the binding to KIR2DL1.
54. A human or humanized antibody that competes with 1-7F9 in the binding to KIR2DL2.
55. A human or humanized antibody that competes with 1-4F1 in the binding to KIR2DL2.
56. A human or humanized antibody that competes with 1-7F9 in the binding to KIR2DL3.
57. A human or humanized antibody that competes with 1-4F1 in the binding to KIR2DL3.
58. A human or humanized antibody that competes with 1-7F9 in the binding to KIR2DL1 and KIR2DL2/3.
59. A human or humanized antibody that competes with 1-4F1 in the binding to KIR2DL1 and KIR2DL2/3.
60. The human or humanized antibody of any of aspects 52-59, which does not bind at least one of KIR2DS4 and KIR2DS3.
61. The human or humanized antibody of any of aspects 52-60, which blocks KIR2DL1 or KIR2DL2/3 binding to an HLA-C class I molecule.
62. The human or humanized antibody of any of aspects 52-47, which potentiates the lytic activity of an NK cell against a human target cell expressing an HLA-C class I molecule.
63. The human or humanized antibody of any of aspects 52-62, which antibody comprises a light chain variable region comprising an amino acid sequence at least 90% identical to SEQ ID NO:15, and a heavy chain variable region comprising an amino acid sequence at least 90% identical to SEQ ID NO:17, or a light chain variable region at least 90% identical to SEQ ID NO:39, and a heavy chain variable region comprising an amino acid sequence at least 90% identical to SEQ ID NO:41.
64. The human or humanized antibody of any of aspects 52-63, which is an IgG1, IgG2, IgG3, or IgG4 antibody.
65. The human or humanized antibody of aspect 64, which is an IgG4 antibody.
66. The human antibody of aspect 64, which is an IgG2 antibody.
67. A human or humanized antibody that binds to each one of KIR2DL1, -2, and -3, and which blocks KIR2DL1, -2, or -3 binding to an HLA-C class I molecule.
68. An antibody that interacts with residues M44 and F45 of KIR2DL1.
69. The antibody of aspect 68, which further interacts with one or more of KIR2DL1 residues L38, R41, N46, D47, T48, L49, R50, I52, F64, D72, Y80, P87, and Y88.
70. An antibody that binds to KIR2DL1 exclusively within a region defined by the amino acid residues L38, R41, M44, F45, N46, D47, T48, L49, R50, I52, F64, D72, Y80, P87, and Y88.
71. An antibody that binds to KIR2DL1 and KIR2DL2/3 without interacting with amino acid residues outside the region defined by the residues L38, R41, M44, F45, N46, D47, T48, L49, R50, I52, F64, D72, Y80, P87, and Y88.
72. The antibody of any of aspects 67-71, which is human antibody 1-7F9.
73. An antibody fragment or antibody derivative comprising at least one light chain CDR of the antibody of any of the preceding aspects.
74. An antibody fragment or antibody derivative comprising at least two light chain CDRs of the antibody of any of the preceding aspects.
75. An antibody fragment or antibody derivative comprising at least three light chain CDRs of the antibody of any of the preceding aspects.
76. An antibody fragment or antibody derivative comprising a VL region of the antibody of any of the preceding aspects.
77. An antibody fragment or antibody derivative comprising at least one heavy chain CDR of the antibody of any of the preceding aspects.
78. An antibody fragment or antibody derivative comprising at least two heavy chain CDRs of the antibody of any of the preceding aspects.
79. An antibody fragment or antibody derivative comprising at least three heavy chain CDRs of the antibody of any of the preceding aspects.
80. An antibody fragment or antibody derivative comprising a VH region of the antibody of any of the preceding aspects.
81. An antibody fragment or antibody derivative comprising all CDRs of the antibody of any of the preceding aspects.
82. An antibody fragment or antibody derivative comprising the VH and VL regions of the antibody of any of the preceding aspects.
83. A hybridoma producing the antibody of any of the preceding aspects.
84. A nucleic acid encoding the antibody or antibody fragment of any of aspects 1-82.
85. A vector comprising the nucleic acid of aspect 84.
86. A cell comprising the vector of aspect 85.
87. The cell of aspect 86, wherein the cell is selected from a simian COS cell, a CHO cell, and a human myeloma cell.
88. A method of producing an anti-KIR antibody or antibody fragment comprising culturing the cell of aspect 86 under conditions suitable for expression of the anti-KIR antibody, antibody fragment, respectively.
89. A method of producing a derivative of an anti-KIR antibody or anti-KIR antibody fragment comprising providing an anti-KIR antibody or antibody fragment and conjugating at least one derivative moiety thereto.
90. A method of treating a cancer in a subject, which method comprises administering to a subject suffering from cancer an effective amount of the antibody or antibody fragment or derivative of any of aspects 1-82.
91. The method of aspect 90, further comprising administering to the patient an agent selected from a chemotherapeutic, radiotherapeutic, anti-angiogenic, immunomodulatory, and hormonal agent.
92. A method of treating a disease or disorder caused by a virus in a subject, which method comprises administering to a subject suffering from disease or disorder caused by a virus an effective amount of the antibody or antibody fragment or derivative of any of aspects 1-82.
93. A use of the antibody or antibody fragment or derivative of any of aspects 1-82 in the preparation of a medicament for treating cancer.

94. A use of the antibody or antibody fragment or derivative of any of aspects 1-82 in the preparation of a medicament for treating a disease or disorder caused by a virus.
95. A composition comprising the antibody or antibody fragment or derivative of any of aspects 1-82, and a pharmaceutically acceptable carrier or excipient.
96. The composition of aspect 95, comprising Polysorbate 80.
97. The composition of aspect 95, comprising Sucrose.
98. The composition of aspect 95, comprising Polysorbate 80 and Sucrose.
99. The composition of any of aspects 95-98, further comprising an agent selected from a chemotherapeutic, radiotherapeutic, anti-angiogenic, immunomodulatory, and hormonal agent.
100. The composition of any of aspects 95-99, in which the antibody, antibody fragment, or antibody derivative is covalently conjugated to a tumor-targeting agent.
101. The composition of any of aspects 95-99, in which the antibody, antibody fragment, or antibody derivative is encapsulated in a liposome.
102. The composition of any of aspects 95-99, further comprising an antibody binding to a KIR, wherein the KIR is not KIR2DL1, KIR2DL2, KIR2DL3, KIR2DS1, or KIR2DS2.
103. A method of increasing the lytic activity of a cell selected from a lymphocyte and an NK cell comprising contacting the cell with the antibody, antibody fragment or derivative of any of aspects 1-82.
104. A method of reducing the interaction between a KIR expressed by a cell selected from a lymphocyte, T cell, and an NK cell, and an HLA-C class I molecule expressed by a target cell, the method comprising contacting the cell with the antibody or antibody fragment or derivative of any of aspects 1-82.
105. A method of neutralizing the inhibitory activity of a KIR expressed by an NK cell, the method comprising contacting the NK cell with the antibody or antibody fragment or derivative of any of aspects 1-82.
106. A human antibody that binds to each one of KIR2DL1, KIR2DL2, and KIR2DL3, which antibody blocks the binding of an HLA-Cw4 molecule to KIR2DL1, and the binding of an HLA-Cw3 molecule to at least one of KIR2DL2 or KIR2DL3.
107. The antibody or antibody fragment or derivative according to any of aspects 1-82, wherein the KIR2DL1 comprises the amino acid sequence of SEQ ID NO:23, the KIR2DL2 comprises the amino acid sequence of SEQ ID NO:24, and/or the KIR2DL3 comprises the amino acid sequence of SEQ ID NO:25.
108. A compound that binds to substantially the same KIR2DL1 epitope as the antibody, antibody fragment, or antibody derivative of any of aspects 1-82.
109. A compound that binds to essentially the same KIR2DL1 epitope as the antibody, antibody fragment, or antibody derivative of any of aspects 1-82.
110. An antibody or antibody derivative comprising a light chain comprising the sequence of SEQ ID NO:36.
111. An antibody or antibody derivative comprising a heavy chain comprising the sequence of SEQ ID NO:37.
112. An antibody or antibody derivative comprising the light chain of aspect 109 and the heavy chain of aspect 110.
113. An antibody consisting of a light chain comprising the sequence of SEQ ID NO:36 and a heavy chain consisting of the sequence of SEQ ID NO:37.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. An isolated human antibody that binds to each one of human KIR2DL1, human KIR2DL2, and human KIR2DL3, but which does not bind human KIR2DS4, said human antibody comprising:
 (a)(i) a heavy chain CDR1 amino acid sequence corresponding to residues 31-35 of SEQ ID NO:17;
 (a)(ii) a heavy chain CDR2 amino acid sequence corresponding to residues 50-65 of SEQ ID NO:17;
 (a)(iii) a heavy chain CDR3 amino acid sequence corresponding to residues 99-112 of SEQ ID NO:17;
 (a)(iv) a light chain CDR1 amino acid sequence corresponding to residues 24-34 of SEQ ID NO:15;
 (a)(v) a light chain CDR2 amino acid sequence corresponding to residues 50-56 of SEQ ID NO:15; and
 (a)(vi) a light chain CDR3 amino acid sequence corresponding to residues 89-97 or SEQ ID NO:15; or
 (b) a VL region comprising SEQ ID NO: 15 and a VH region comprising SEQ ID NO: 17.

2. The isolated human antibody of claim 1, which further does not bind to human KIR2DS3.

3. The isolated human antibody of claim 2, which antibody has a Kd for human KIR2DL3 of no more than about 0.025 nM.

4. The isolated human antibody of claim 1, which antibody blocks the binding of at least one of human KIR2DL1, human KIR2DL2, and human KIR2DL3 to a human HLA-C class I molecule.

5. The isolated human antibody of claim 1, which antibody blocks the binding of a human HLA-Cw4 molecule to human KIR2DL1 and the binding of a human HLA-Cw3 molecule to at least one of human KIR2DL2 or human KIR2DL3.

6. The isolated human antibody of claim 1, which antibody potentiates the lytic activity of an NK cell against a human target cell a human HLA-C class I molecule.

7. The isolated human antibody of claim 1, said antibody comprising:
 (a)(i) a heavy chain CDR1 amino acid sequence corresponding to residues 31-35 of SEQ ID NO:17;
 (a)(ii) a heavy chain CDR2 amino acid sequence corresponding to residues 50-65 of SEQ ID NO:17;
 (a)(iii) a heavy chain CDR3 amino acid sequence corresponding to residues 99-112 of SEQ ID NO:17;
 (a)(iv) a light chain CDR1 amino acid sequence corresponding to residues 24-34 of SEQ ED NO:15;
 (a)(v) a light chain CDR2 amino acid sequence corresponding to residues 50-56 of SEQ ID NO:15; and
 (a)(vi) a light chain CDR3 amino acid sequence corresponding to residues 89-97 of SEQ ID NO:15.

8. The isolated human antibody of claim 7, which antibody is an IgG4 antibody.

9. The isolated human antibody of claim 1, said antibody comprising a VL region comprising SEQ ID NO: 15 and a VH region comprising SEQ ID NO: 17.

10. The isolated human antibody of claim 1, which antibody has a dissociation constant (Kd) for human KIR2DL1 of no more than about 0.45 nM.

11. The isolated human antibody of claim 1, which antibody has a Kd for human KIR2DL3 of no more than about 0.025 nM.

12. The isolated human antibody of claim 1, which antibody is a monoclonal antibody.

13. The isolated human antibody of claim 12, which antibody is an IgG1, IgG2, IgG3, or IgG4 antibody.

14. The isolated human antibody of claim 13, which antibody is an IgG4 antibody.

15. The isolated human antibody of claim 1, which antibody is an IgG4 antibody.

16. A pharmaceutical composition comprising a human antibody of claim 1 in an amount effective to detectably potentiate NK cell cytotoxicity in a patient and a pharmaceutically acceptable carrier or excipient.

17. The pharmaceutical composition of claim 16, comprising Polysorbate 80, sucrose, or a combination thereof.

18. The composition of claim 16, wherein the antibody comprises:
 (a)(i) a heavy chain CDR1 amino acid sequence corresponding to residues 31-35 of SEQ ID NO:17;

(a)(ii) a heavy chain CDR2 amino acid sequence corresponding to residues 50-65 of SEQ ID NO:17:

(a)(ii) a heavy chain CDR3 amino acid sequence corresponding to residues 99-112 of SEQ JD NO: 17;

(a)(iv) a light chain CDR1 amino acid sequence corresponding to residues 24-34 of SEQ ID NO:15;

(a)(v) a light chain CDR2 amino acid sequence corresponding to residues 50-56 of SEQ ID NO:15; and (a)(vi) a light chain CDR3 amino acid sequence corresponding to residues 89-97 of SEQ JD NO:15.

19. The composition of claim 16, wherein the antibody comprises a VL region comprising SEQ ID NO: 15 and a VH region comprising SEQ ID NO: 17.

20. The composition of claim 16, wherein the antibody is an IgG4 antibody.

\* \* \* \* \*

SEQUENCE LISTING

<160> NUMBER OF SEQ ID NOS: 42

<210> SEQ ID NO 1
<211> LENGTH: 128
<212> TYPE: PRT
<213> ORGANISM: Mus musculus

<400> SEQUENCE: 1

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys Arg
        115                 120                 125

<210> SEQ ID NO 2
<211> LENGTH: 131
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ser
            20                  25                  30

Met Ser Ala Ser Leu Gly Glu Arg Val Thr Met Thr Cys Thr Ala Ser
        35                  40                  45

Ser Ser Val Ser Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys Arg
    130

<210> SEQ ID NO 3
<211> LENGTH: 11
<212> TYPE: PRT
<213> ORGANISM: Mus musculus

<400> SEQUENCE: 3

Lys Ala Ser Glu Asn Val Val Thr Tyr Val Ser

```
<210> SEQ ID NO 4
<211> LENGTH: 12
<212> TYPE: PRT
<213> ORGANISM: Mus musculus

<400> SEQUENCE: 4

Thr Ala Ser Ser Ser Val Ser Ser Ser Tyr Leu Tyr
1               5                   10

<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5

<210> SEQ ID NO 6
<211> LENGTH: 7
<212> TYPE: PRT
<213> ORGANISM: Mus musculus

<400> SEQUENCE: 6

Ser Thr Ser Asn Leu Ala Ser
1               5

<210> SEQ ID NO 7
<211> LENGTH: 9
<212> TYPE: PRT
<213> ORGANISM: Mus musculus

<400> SEQUENCE: 7

Gly Gln Gly Tyr Ser Tyr Pro Tyr Thr
1               5

<210> SEQ ID NO 8
<211> LENGTH: 9
<212> TYPE: PRT
<213> ORGANISM: Mus musculus

<400> SEQUENCE: 8

His Gln Tyr His Arg Ser Pro Pro Thr
1               5

<210> SEQ ID NO 9
<211> LENGTH: 140
<212> TYPE: PRT
<213> ORGANISM: Mus musculus

<400> SEQUENCE: 9

Met Ala Val Leu Gly Leu Leu Phe Cys Leu Val Thr Phe Pro Ser Cys
1               5                   10                  15

Val Leu Ser Gln Val Gln Leu Glu Gln Ser Gly Pro Gly Leu Val Gln
            20                  25                  30

Pro Ser Gln Ser Leu Ser Ile Thr Cys Thr Val Ser Gly Phe Ser Phe
        35                  40                  45

Thr Pro Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Ala
65                  70                  75                  80
```

```
Ala Phe Ile Ser Arg Leu Ser Ile Asn Lys Asp Asn Ser Lys Ser Gln
                85                  90                  95

Val Phe Phe Lys Met Asn Ser Leu Gln Val Asn Asp Thr Ala Ile Tyr
            100                 105                 110

Tyr Cys Ala Arg Asn Pro Arg Pro Gly Asn Tyr Pro Tyr Gly Met Asp
        115                 120                 125

Tyr Trp Gly Gln Gly Thr Ser Val Thr Val Ser Ser
130                 135                 140

<210> SEQ ID NO 10
<211> LENGTH: 10
<212> TYPE: PRT
<213> ORGANISM: Mus musculus

<400> SEQUENCE: 10

Gly Phe Ser Phe Thr Pro Tyr Gly Val His
1               5                   10

<210> SEQ ID NO 11
<211> LENGTH: 16
<212> TYPE: PRT
<213> ORGANISM: Mus musculus

<400> SEQUENCE: 11

Val Ile Trp Ser Gly Gly Asn Thr Asp Tyr Asn Ala Ala Phe Ile Ser
1               5                   10                  15

<210> SEQ ID NO 12
<211> LENGTH: 13
<212> TYPE: PRT
<213> ORGANISM: Mus musculus

<400> SEQUENCE: 12

Asn Pro Arg Pro Gly Asn Tyr Pro Tyr Gly Met Asp Tyr
1               5                   10

<210> SEQ ID NO 13
<211> LENGTH: 42
<212> TYPE: DNA
<213> ORGANISM: Artificial
<220> FEATURE:
<223> OTHER INFORMATION: Primer

<400> SEQUENCE: 13
ggaattccag gaggaattta aaatgcatga gggagtccac ag                          42

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
cgggatccca ggtgtctggg gttacc                                            26

<210> SEQ ID NO 15
<211> LENGTH: 109
<212> TYPE: PRT
<213> ORGANISM: Homo sapiens

<400> SEQUENCE: 15

Glu Ile Val Leu Thr Gln Ser Pro Val Thr Leu Ser Leu Ser Pro Gly
1               5                   10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105

<210> SEQ ID NO 16
<211> LENGTH: 327
<212> TYPE: DNA
<213> ORGANISM: Homo sapiens

<400> SEQUENCE: 16
gaaattgtgt tgacacagtc tccagtcacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ttgtcagcag cgtagcaact ggatgtacac ttttggccag     300
gggaccaagc tggagatcaa acgaact                                         327

<210> SEQ ID NO 17
<211> LENGTH: 123
<212> TYPE: PRT
<213> ORGANISM: Homo sapiens

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 18
<211> LENGTH: 369
<212> TYPE: DNA
<213> ORGANISM: Homo sapiens

<400> SEQUENCE: 18
caggtccagc tggtgcagtc tggggctgag gtgaagaagc ctgggtcctc ggtgaaggtc      60

```
tcctgcaagg cttctggagg caccttcagt ttctatgcta tcagctgggt gcgacaggcc    120
cctggacaag ggcttgagtg gatgggaggg ttcatcccta tctttggtgc agcaaactac    180
gcacagaagt tccagggcag agtcacgatt accgcggacg aatccacgag cacagcctac    240
atggaactga gcagcctgag atctgacgac acggccgtgt attactgtgc gagaatccct    300
agtgggagct actactacga ctacgatatg gacgtctggg gccaagggac cacggtcacc    360
gtctcctca                                                            369
```

<210> SEQ ID NO 19
<211> LENGTH: 121
<212> TYPE: PRT
<213> ORGANISM: Mus musculus

<400> SEQUENCE: 19

```
Gln Val Gln Leu Glu Gln Ser Gly Pro Gly Leu Val Gln Pro Ser Gln
1               5                   10                  15

Ser Leu Ser Ile Thr Cys Thr Val Ser Gly Phe Ser Phe Thr Pro Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Ala Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Val Asn Asp Thr Ala Ile Tyr Tyr Cys Ala
                85                  90                  95

Arg Asn Pro Arg Pro Gly Asn Tyr Pro Tyr Gly Met Asp Tyr Trp Gly
            100                 105                 110

Gln Gly Thr Ser Val Thr Val Ser Ser
        115                 120
```

<210> SEQ ID NO 20
<211> LENGTH: 121
<212> TYPE: PRT
<213> ORGANISM: Mus musculus

<400> SEQUENCE: 20

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Met Lys Gln Arg Pro Gly Gln Gly Leu Glu Trp Ile
        35                  40                  45

Gly Thr Ile Tyr Pro Gly Asn Ser Asp Thr Asn Tyr Asn Gln Lys Phe
    50                  55                  60

Lys Gly Lys Ala Lys Leu Thr Ala Val Thr Ser Thr Asn Thr Ala Tyr
65                  70                  75                  80

Met Glu Leu Ser Ser Leu Thr Asn Glu Asp Ser Ala Val Tyr Tyr Cys
                85                  90                  95

Ser Arg Pro Thr Thr Ala Thr Arg Ser Ser Ala Met Asp Tyr Trp Gly
            100                 105                 110

Gln Gly Thr Ser Val Thr Val Ser Ser
        115                 120
```

<210> SEQ ID NO 21
<211> LENGTH: 108
<212> TYPE: PRT

<213> ORGANISM: Mus musculus

<400> SEQUENCE: 21

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 22
<211> LENGTH: 109
<212> TYPE: PRT
<213> ORGANISM: Mus musculus

<400> SEQUENCE: 22

Gln Ile Val Leu Thr Gln Ser Pro Ala Ser Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys Arg
            100                 105

<210> SEQ ID NO 23
<211> LENGTH: 224
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Xaa is Pro or Leu
<220> FEATURE:
<221> NAME/KEY: MISC_FEATURE
<222> LOCATION: (16)..(16)
<223> OTHER INFORMATION: Xaa is Pro or Arg
<220> FEATURE:
<221> NAME/KEY: MISC_FEATURE
<222> LOCATION: (114)..(114)
<223> OTHER INFORMATION: Xaa is Pro or Leu

<400> SEQUENCE: 23

His Glu Gly Val His Arg Lys Pro Ser Leu Leu Ala His Pro Gly Xaa
1               5                   10                  15

Leu Val Lys Ser Glu Glu Thr Val Ile Leu Gln Cys Trp Ser Asp Val
            20                  25                  30

```
Met Phe Glu His Phe Leu Leu His Arg Glu Gly Met Phe Asn Asp Thr
            35                  40                  45

Leu Arg Leu Ile Gly Glu His His Asp Gly Val Ser Lys Ala Asn Phe
 50                      55                  60

Ser Ile Ser Arg Met Thr Gln Asp Leu Ala Gly Thr Tyr Arg Cys Tyr
 65                  70                  75                  80

Gly Ser Val Thr His Ser Pro Tyr Gln Val Ser Ala Pro Ser Asp Pro
                 85                  90                  95

Leu Asp Ile Val Ile Ile Gly Leu Tyr Glu Lys Pro Ser Leu Ser Ala
                100                 105                 110

Gln Xaa Gly Pro Thr Val Leu Ala Gly Glu Asn Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Leu Pro Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe His Asp Ser Pro Tyr Glu Trp Ser Lys Ser Ser
                180                 185                 190

Asp Pro Leu Leu Val Ser Val Thr Gly Asn Pro Ser Asn Ser Trp Pro
                195                 200                 205

Ser Pro Thr Glu Pro Ser Ser Lys Thr Gly Asn Pro Arg His Leu His
    210                 215                 220

<210> SEQ ID NO 24
<211> LENGTH: 224
<212> TYPE: PRT
<213> ORGANISM: Homo sapiens

<400> SEQUENCE: 24

His Glu Gly Val His Arg Lys Pro Ser Leu Leu Ala His Pro Gly Arg
  1               5                  10                  15

Leu Val Lys Ser Glu Glu Thr Val Ile Leu Gln Cys Trp Ser Asp Val
                 20                  25                  30

Arg Phe Glu His Phe Leu Leu His Arg Glu Gly Lys Phe Lys Asp Thr
            35                  40                  45

Leu His Leu Ile Gly Glu His His Asp Gly Val Ser Lys Ala Asn Phe
 50                      55                  60

Ser Ile Gly Pro Met Met Gln Asp Leu Ala Gly Thr Tyr Arg Cys Tyr
 65                  70                  75                  80

Gly Ser Val Thr His Ser Pro Tyr Gln Leu Ser Ala Pro Ser Asp Pro
                 85                  90                  95

Leu Asp Ile Val Ile Thr Gly Leu Tyr Glu Lys Pro Ser Leu Ser Ala
                100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Cys Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
                180                 185                 190
```

```
Asp Pro Leu Leu Val Ser Val Ile Gly Asn Pro Ser Asn Ser Trp Pro
        195                 200                 205

Ser Pro Thr Glu Pro Ser Ser Lys Thr Gly Asn Pro Arg His Leu His
    210                 215                 220

<210> SEQ ID NO 25
<211> LENGTH: 224
<212> TYPE: PRT
<213> ORGANISM: Homo sapiens

<400> SEQUENCE: 25

His Glu Gly Val His Arg Lys Pro Ser Leu Leu Ala His Pro Gly Pro
1               5                  10                  15

Leu Val Lys Ser Glu Glu Thr Val Ile Leu Gln Cys Trp Ser Asp Val
            20                  25                  30

Arg Phe Gln His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Thr Gly Asn Pro Ser Asn Ser Trp Pro
        195                 200                 205

Ser Pro Thr Glu Pro Ser Ser Glu Thr Gly Asn Pro Arg His Leu His
    210                 215                 220

<210> SEQ ID NO 26
<211> LENGTH: 45
<212> TYPE: DNA
<213> ORGANISM: Artificial
<220> FEATURE:
<223> OTHER INFORMATION: Primer

<400> SEQUENCE: 26
ctaatacgac tcactatagg gcaagcagtg gtatcaacgc agagt            45

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
ctaatacgac tcactatagg g                                      21
```

```
<210> SEQ ID NO 28
<211> LENGTH: 32
<212> TYPE: DNA
<213> ORGANISM: Artificial
<220> FEATURE:
<223> OTHER INFORMATION: Primer

<400> SEQUENCE: 28
gcaggcacac aacagaggca gttccagatt tc                              32

<210> SEQ ID NO 29
<211> LENGTH: 45
<212> TYPE: DNA
<213> ORGANISM: Artificial
<220> FEATURE:
<223> OTHER INFORMATION: Primer

<400> SEQUENCE: 29
ctaatacgac tcactatagg gcaagcagtg gtatcaacgc agagt                45

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
ctaatacgac tcactatagg g                                          21

<210> SEQ ID NO 31
<211> LENGTH: 23
<212> TYPE: DNA
<213> ORGANISM: Artificial
<220> FEATURE:
<223> OTHER INFORMATION: Primer

<400> SEQUENCE: 31
gtgccagggg gaagaccgat ggg                                        23

<210> SEQ ID NO 32
<211> LENGTH: 16
<212> TYPE: DNA
<213> ORGANISM: Artificial
<220> FEATURE:
<223> OTHER INFORMATION: Primer

<400> SEQUENCE: 32
gtaaaacgac ggccag                                                16

<210> SEQ ID NO 33
<211> LENGTH: 17
<212> TYPE: DNA
<213> ORGANISM: Artificial
<220> FEATURE:
<223> OTHER INFORMATION: Primer

<400> SEQUENCE: 33
caggaaacag ctatgac                                               17

<210> SEQ ID NO 34
<211> LENGTH: 108
<212> TYPE: PRT
<213> ORGANISM: Homo sapiens

<400> SEQUENCE: 34
```

-continued

Val Val Met Thr Gln Ser Pro Ser Thr Leu Ser Ala Ser Val Gly Asp
1               5                   10                  15

Thr Ile Thr Ile Thr Cys Arg Ala Ser Gln Ser Ile Glu Thr Trp Leu
                20                  25                  30

Ala Trp Tyr Gln Gln Lys Pro Gly Lys Ala Pro Lys Leu Leu Ile Tyr
        35                  40                  45

Lys Ala Ser Thr Leu Lys Thr Gly Val Pro Ser Arg Phe Ser Gly Ser
    50                  55                  60

Gly Ser Gly Thr Glu Phe Thr Leu Thr Ile Ser Gly Leu Gln Phe Asp
65                  70                  75                  80

Asp Phe Ala Thr Tyr His Cys Gln His Tyr Ala Gly Tyr Ser Ala Thr
                85                  90                  95

Phe Gly Gln Gly Thr Arg Val Glu Ile Lys Arg Thr
            100                 105

<210> SEQ ID NO 35
<211> LENGTH: 119
<212> TYPE: PRT
<213> ORGANISM: Homo sapiens

<400> SEQUENCE: 35

Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ser Ala His
                20                  25                  30

Thr Met Asn Trp Val Arg Arg Val Pro Gly Gly Gly Leu Glu Trp Val
            35                  40                  45

Ala Ser Ile Ser Thr Ser Ser Thr Tyr Arg Asp Tyr Ala Asp Ala Val
    50                  55                  60

Lys Gly Arg Phe Thr Val Ser Arg Asp Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110

Trp Gly Pro Gly Thr Val Val
            115

<210> SEQ ID NO 36
<211> LENGTH: 214
<212> TYPE: PRT
<213> ORGANISM: Homo sapiens

<400> SEQUENCE: 36

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala

Pro Ser Val Phe Ile Phe Pro Pro Ser Asp Glu Gln Leu Lys Ser Gly
            100                 105                 110

Thr Ala Ser Val Val Cys Leu Leu Asn Asn Phe Tyr Pro Arg Glu Ala
        115                 120                 125

Lys Val Gln Trp Lys Val Asp Asn Ala Leu Gln Ser Gly Asn Ser Gln
130                 135                 140

Glu Ser Val Thr Glu Gln Asp Ser Lys Asp Ser Thr Tyr Ser Leu Ser
    145                 150                 155                 160

Ser Thr Leu Thr Leu Ser Lys Ala Asp Tyr Glu Lys His Lys Val Tyr
                165                 170                 175

Ala Cys Glu Val Thr His Gln Gly Leu Ser Ser Pro Val Thr Lys Ser
            180                 185                 190

Phe Asn Arg Gly Glu Cys
        195

<210> SEQ ID NO 37
<211> LENGTH: 450
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu

```
                    260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
Gly Lys
    450

<210> SEQ ID NO 38
<211> LENGTH: 100
<212> TYPE: PRT
<213> ORGANISM: Homo sapiens

<400> SEQUENCE: 38

Gln Glu Gly Val His Arg Lys Pro Ser Phe Leu Ala Leu Pro Gly His
1               5                   10                  15
Leu Val Lys Ser Glu Glu Thr Val Ile Leu Gln Cys Trp Ser Asp Val
            20                  25                  30
Met Phe Glu His Phe Leu Leu His Arg Glu Gly Lys Phe Asn Asn Thr
        35                  40                  45
Leu His Leu Ile Gly Glu His His Asp Gly Val Ser Lys Ala Asn Phe
    50                  55                  60
Ser Ile Gly Pro Met Met Pro Val Leu Ala Gly Thr Tyr Arg Cys Tyr
65                  70                  75                  80
Gly Ser Val Pro His Ser Pro Tyr Gln Leu Ser Ala Pro Ser Asp Pro
                85                  90                  95
Leu Asp Met Val
            100

<210> SEQ ID NO 39
<211> LENGTH: 109
<212> TYPE: PRT
<213> ORGANISM: Homo sapiens
<220> FEATURE:
<221> NAME/KEY: MISC_FEATURE
<222> LOCATION: (1)..(109)
<223> OTHER INFORMATION: Xaa 3 is Q or R.  Xaa 4 is L or M.  Xaa 9 is S
      or F.  Xaa 24 is R or W.  Xaa 32 is A or Y.  Xaa 41 is G or A.
      Xaa 47 is L or F.  Xaa 50 is D or Y.  Xaa 55 is E or Q.  Xaa 71 is
      F or Y.  Xaa 74 is A or T.
```

-continued

```
<400> SEQUENCE: 39

Ala Ile Xaa Xaa Thr Gln Ser Pro Xaa Ser Leu Ser Ala Ser Val Gly
1               5                   10                  15

Asp Arg Val Thr Ile Thr Xaa Xaa Ala Ser Gln Gly Ile Ser Ser Xaa
            20                  25                  30

Leu Ala Trp Tyr Gln Gln Lys Pro Xaa Lys Ala Pro Lys Leu Xaa Ile
        35                  40                  45

Tyr Xaa Ala Ser Ser Leu Xaa Ser Gly Val Pro Ser Arg Phe Ser Gly
    50                  55                  60

Ser Gly Ser Gly Thr Asp Xaa Thr Leu Xaa Ile Ser Ser Leu Gln Pro
65              70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg Thr
            100                 105

<210> SEQ ID NO 40
<211> LENGTH: 327
<212> TYPE: DNA
<213> ORGANISM: Homo sapiens
<220> FEATURE:
<221> NAME/KEY: misc_feature
<222> LOCATION: (1)..(153)
<223> OTHER INFORMATION: n8 is a or g.  n10 is t or a.  n26 is c or t.
      n70 is c or t.  n75 is a or c.  n94 is g or t.  n95 is c or a.
      n114 is g or a.  n122 is g or c.  n123 is g or a.  n129 is t or c.
      n139 is c or t.  n141 is g or c.  n148 is g or t.  n153 is c or a.
<220> FEATURE:
<221> NAME/KEY: misc_feature
<222> LOCATION: (154)..(327)
<223> OTHER INFORMATION: n162 is g or a.  n163 is g or c.  n207 is a or
      g.  n212 is t or a.  n220 is g or a.

<400> SEQUENCE: 40
gccatccngn tgacccagtc tccatnctcc ctgtctgcat ctgtaggaga cagagtcacc      60
atcacttgcn gggcnagtca gggcattagc agtnnttag cctggtatca gcanaaacca     120
gnnaaagcnc ctaagctcnt natctatnat gcntccagtt tnnaaagtgg ggtcccatca    180
aggttcagcg gcagtggatc tgggacngat tncactctcn ccatcagcag cctgcagcct    240
gaagattttg caacttatta ctgtcaacag tattatagta ccccgctcac tttcggcgga   300
gggaccaagg tggagatcaa acgaact                                        327

<210> SEQ ID NO 41
<211> LENGTH: 124
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Asn Ser Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Ser Ala Asp Glu Ser Thr Arg Thr Val Tyr
65              70                  75                  80

Met Glu Leu Asn Ser Leu Arg Ser Glu Asp Thr Ala Val Tyr Tyr Cys
                85                  90                  95
```

```
Ala Arg Gly Tyr Tyr Asp Ile Phe Lys Asp Tyr Tyr Gly Met Asp
            100                 105                 110
Val Trp Gly Gln Gly Thr Thr Val Thr Val Ser Ser
        115                 120

<210> SEQ ID NO 42
<211> LENGTH: 372
<212> TYPE: DNA
<213> ORGANISM: Homo sapiens

<400> SEQUENCE: 42
caggtccagc tggtgcagtc tggggctgag gttaagaagc ctgggtcctc ggtgaaggtc      60
tcctgcaagg cttctggagg cacctccaac agctattcta ttaactgggt gcgacaggcc     120
cctggacaag gcttgagtg gatgggaggg atcatcccta tatttggtac agcaaactac     180
gcacagaagt tccagggcag agtcacgatt tccgcggacg aatccacgcg cacagtctac     240
atggagctga acagtctgag atctgaggat acggccgtgt attactgtgc gagaggatat     300
tacgatattt tcaaggacta ctattacggt atggacgtct ggggccaagg gaccacggtc     360
accgtctcct ca                                                        372
```